(12) United States Patent
Yura et al.

(10) Patent No.: US 6,911,443 B2
(45) Date of Patent: Jun. 28, 2005

(54) IMIDAZOPYRIMIDINE DERIVATIVES AND TRIAZOLOPYRIMIDINE DERIVATIVES

(75) Inventors: Takeshi Yura, Nara-ken (JP); Arnel B. Concepcion, Nara-ken (JP); Gyoonhee Han, Daejon (KR); Makiko Marumo, Nara-ken (JP); Hiroko Yoshino, Nara-ken (JP); Norihiro Kawamura, Nara-ken (JP); Toshio Kokubo, Nara-ken (JP); Hiroshi Komura, Nara-ken (JP); Yingfu Li, Nara-ken (JP); Timothy B. Lowinger, Wuppertal (DE); Muneto Mogi, Nara-ken (JP); Noriyuki Yamamoto, Nara-ken (JP); Nagahiro Yoshida, Kyoto (JP); Scott Miller, Longmont, CO (US); Margaret A. Popp, West Chester, OH (US); Aniko M. Redmann, Derby, CT (US); Martha E. Rodriguez, Longmont, CO (US); William J. Scott, Guilford, CT (US); Ming Wang, Milford, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/258,628

(22) PCT Filed: Apr. 17, 2001

(86) PCT No.: PCT/EP01/04357

§ 371 (c)(1),
(2), (4) Date: Feb. 14, 2003

(87) PCT Pub. No.: WO01/83485

PCT Pub. Date: Nov. 8, 2001

(65) Prior Publication Data

US 2004/0054179 A1 Mar. 18, 2004

(30) Foreign Application Priority Data

Apr. 28, 2000 (JP) ........................ 2000-128870

(51) Int. Cl.[7] ................... C07D 487/04; C07D 417/10; A61K 31/519; A61P 11/06
(52) U.S. Cl. ................. 514/233.2; 514/259.1; 514/259.5; 544/117; 544/118; 544/263; 544/281
(58) Field of Search .............. 514/233.2, 259.31, 514/259.1, 259.5, 259.3; 544/117, 118, 263, 281

(56) References Cited

U.S. PATENT DOCUMENTS 4,483,987 A 11/1984 Wagner ................. 544/263
6,673,564 B2 * 1/2004 Kapeller-Libermann et al. . 435/19

FOREIGN PATENT DOCUMENTS

EP 1054004 11/2000
WO 9916755 4/1999

OTHER PUBLICATIONS

Stewart ZA, Pietenpol JA., Breast Cancer Res. 2001;3(1):5–7. Epub Nov. 2, 2000.*
Ulanova M, Puttagunta L, Kim MK, Schreiber AD, Befus AD., Curr Opin Investig Drugs. May 2003;4(5):552–5.*
Yanagi S, Inatome R, Takano T, Yamamura H., Biochem Biophys Res Commun. Nov. 2, 2001;288(3):495–8.*
Porter, A.E.A. in Comprehensive Organic Chemistry, vol. 4, D.I. Barton, ed, 1979, pp. 98–103.*
Lister, J.H., in Fused Pyrimidines, Part II, D.J. Brown ed., 1971, pp. 120–124.*

* cited by examiner

Primary Examiner—Thomas C. McKenzie

(57) ABSTRACT

A compound of the formula (I)

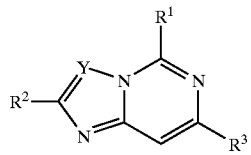

(I)

in which $R^1$ is $-OR^{11}$, $-SR^{11}$, $-SOR^{11}$, $-SO_2R^{11}$, $-NHR^{11}$, or $-NR^{12}R^{13}$, and $R^{11}$, $R^{12}$, and $R^{13}$ are as defined broadly in the text. $R^2$ is H, $C_1$–$C_6$alkyl, carbamoyl, or an ester group. $R^3$ is thienyl, pyridyl optionally substituted by halogen or $C_1$–$C_6$alkoxy; naphthyl optionally substituted by $C_1$–$C_6$alkoxy; dioxane fused phenyl; dioxacyclopentane fused phenyl; or optionally substituted phenyl. Y is CH or N. A process for preparing such compounds, pharmaceutical compositions containing such compounds, and a method of treating asthma using them are also disclosed and claimed.

7 Claims, No Drawings

IMIDAZOPYRIMIDINE DERIVATIVES AND TRIAZOLOPYRIMIDINE DERIVATIVES

TECHNICAL FIELD

The present invention relates to imidazopyrimidine derivatives and triazolopyrimidine derivatives, a process for the preparation of the derivatives and pharmaceutical preparations containing the derivatives. The imidazopyrimidine derivatives and triazolopyrimidine derivatives of the present invention inhibit Syk tyrosine kinase activity.

BACKGROUND ART

It is well known that the mast cells and basophils are the initial players in the pathogenesis of allergic diseases, such as asthma, allergic rhinitis and atopic dermatitis.

The immediate type-I allergic reaction, such as bronchoconstriction in asthma, sneezing in allergic rhinitis and itching in atopic dermatitis, are initiated by the interaction of antigens, such as pollen or house dust, with their specific IgE captured on mast cells and basophils. More specifically, high affinity IgE receptor (FceRI) on the surface of mast cells and basophils traps IgE, which then recognizes antigen. Antigen-IgE interaction engages FceRI, resulting in elicitation of cellular response such as, histamine and $PGD_2$ release to cause the immediate allergic reaction. Activated cells also produce leukotrienes and cytokines to cause the late inflammatory response, such as tissue eosinophilia.

Syk tyrosine kinase (Taniguchi, T. et. al., J. Biol. Chem. 266: 15790–15796 (1991)) is one of tyrosine kinases involved in these cellular responses. Costello, P. S. et. al. suggests that Syk tyrosine kinase is indispensable for the 3 cellular responses; degranulation, lipid mediator synthesis and cytokine production with the use of mast cells derived from syk knockout mice (Oncogene 13: 2595–2605 (1996)). Stenton, G. R. et. al. discloses that the Syk antisense oligo DNA inhalation suppress the parasite antigen-induced pulmonary inflammation in rats (J. Immunol., 164: 3790–3797 (2000)). Therefore, Syk tyrosine kinase inhibitors are expected to suppress both immediate allergic reaction and late inflammatory response.

Further, various genetic and pharmacological studies suggest Syk tyrosine kinase plays important roles in other type of cells. Syk is reported to be essential for the FcγRs-mediated phagocytosis in monocytes/macrophages (Matsuda, M. et. al., Mol. Biol. Cell 7: 1095–1106 (1996)), pre BCR-mediated B cell maturation (Cornall, R. J. et. al., Proc. Natl. Acad. Sci. USA 97: 1713–1718 (2000)), GM-CSF/IL-5-induced eosinophil survival (Yousefi, S. et. al., J. Exp. Med., 183: 1407–1414 (1996)), collagen-induced platelet activation (Poole, A. et. al., EMBO J. 16: 2333–2341 (1997)), differentiation of fibroblast to adipocytes (Wang, H. and Malbon, C. C., J. Biol. Chem. 274: 32159–32166 (1999)) and β-amyloid peptide-/prion peptide-induced neurotoxic product generation in microglia (Combs, C. K. et. al., J. Neurosci. 19: 928–939 (1999)).

Therefore, Syk tyrosine kinase inhibitors have possibilities to prevent antibody dependent cellular cytotoxicity (ADCC), antibody related diseases, eosinophilic inflammation, platelet agglutination, obesity and Alzheimer/prion disease, respectively.

As an effective agent for a Syk inhibitor, pyrimidine-5-carboxyamide derivatives represented by general formula

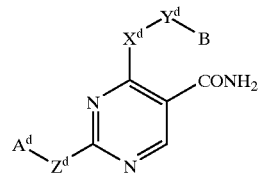

wherein $X^d$ represents O, S, $NR^{1d}$, CO, $NR^{1d}CO$, $CONR^{1d}$, C=N—$OR^{1d}$ or a bond; $Y^d$ represents lower alkylene optionally substituted by $OR^{1d}$ or $NHR^{1d}$ or a bond; $Z^d$ represents O, $NR^{2d}$ or attachment; $A^d$ represents H, optionally substituted lower alkyl, lower alkyl optionally substituted by CO, optionally substituted aryl, optionally substituted heteroaryl, optionally substituted cycloalkyl or optionally substituted saturated heterocycle including N; B represents optionally substituted aryl or optionally substituted heteroaryl; $R^{1d}$ and $R^{2d}$ represent H, lower alkyl, or —CO-lower alkyl, are disclosed in WO99/310773.

As an effective agent for a variety of diseases, various imidazopyrimidine derivatives and triazolopyrimidine derivatives have been studied. For example, Abignente Enrico et al., (Farmaco (1991), 46(10), 1099–110) discloses the compound of the following formula:

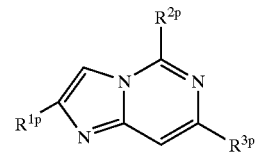

(wherein $R^{1p}$ represents $CO_2H$, $CO_2Et$, $CONH_2$, $CH_2CO_2H$; $R^{2p}$ represents Me, OMe; and $R^{3p}$ represents OMe, Me, Cl) having anti-inflammatory activity.

Danagulyan, G. G. et al., (Khim. Geterotsikl. Soedin. (1992), (2), 225–7) discloses the compounds of the following formula:

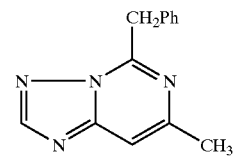

U.S. Pat. No. 4,639,445 discloses the compounds of the following formula

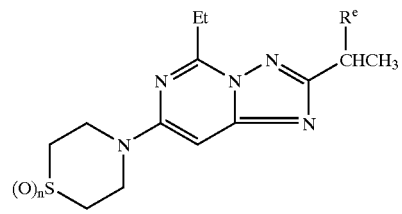

wherein $R^e$ is OH and n is 1 or 2, useful as bronchodilators.

U.S. Pat. No. 4,591,588 discloses the compounds of the following formula

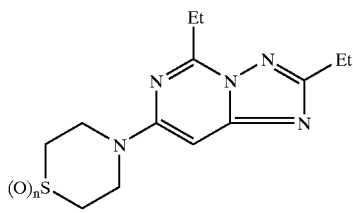

wherein n is 1 or 2, which shows bronchodilator activity.

However, none of the reference relating to imidazopyrimidine derivatives and triazolopyrimidine derivatives has aromatic group at C-7 position nor suggest Syk tyrosine kinase inhibitory activity.

SUMMARY OF THE INVENTION

As a result of extensive studies on chemical modification of imidazopyrimidine derivatives and triazolopyrimidine derivatives, the present inventors have found that the compounds of novel chemical structure related to the present invention have unexpectedly excellent Syk inhibitory activity. The present invention has been accomplished based on these findings.

This invention is to provide a novel compound shown by the following general formula (I) and the salts thereof:

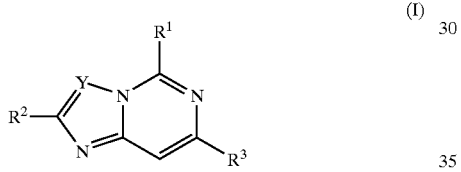

(I)

wherein $R^1$ represents $-OR^{11}$, $-SR^{11}$, $-SOR^{11}$, $-SO_2R^{11}$, $-NHR^{11}$, $-NR^{12}R^{13}$ or $-CR^{14}R^{15}R^{11}$, $R^{11}$ represents H, phenyl carbonyl, thienyl optionally substituted by $COOR^{111}$ ($R^{111}$ is H or $C_1$–$C_6$ alkyl), pyrimidyl, $C_2$–$C_6$ alkenyl, imidazolyl optionally substituted by $C_1$–$C_6$ alkyl, triazolyl optionally substituted by $C_1$–$C_6$ alkyl, tetrazolyl optionally substituted by $C_1$–$C_6$ alkyl, thiadiazolyl optionally substituted by $C_1$–$C_6$ alkyl, pyrrolidinyl optionally substituted by $C_1$–$C_6$ alkyl, cyclohexenyl, $C_1$–$C_{10}$ straight- or branched-alkyl optionally substituted by $R^{112}$, $R^{113}$ and/or $R^{114}$, $C_3$–$C_{10}$ cycloalkyl optionally substituted by $R^{112}$, $R^{113}$ and/or $R^{114}$, phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 hetero atoms selected from the group consisting of N, O and S and optionally substituted by $R^{118}$, $R^{112}$ represents halogen, amino, $-COOR^{112a}$ ($R^{112a}$ represents H or $C_1$–$C_6$ alkyl) $-CO-NH-CH_3$, $-CO-NH-(CH_2)_pCN$ (wherein p represents integer of 0–6), $-NH-COOR^{112a}$, pyrazinyl, tetrazolyl, dihydrothiophenyl, morpholino, piperidino, di($C_1$–$C_6$ alkyl)amino, indolyl, pyridinyl, thiophenyl, or phenyl optionally substituted by one to three substituents selected from the group consisting of halogen, $C_1$–$C_6$ alkyl, hydroxy, $C_1$–$C_6$ alkoxy, and trihalogen substituted $C_1$–$C_6$ alkyl, $R^{113}$ represents halogen, hydroxy, or $C_1$–$C_6$ alkoxy-carbonyl, $R^{114}$ represents halogen, $R^{115}$ represents H, halogen, amino, hydroxy, nitro, cyano, $C_1$–$C_6$ alkoxy, carboxy, $C_1$–$C_6$ alkoxy carbonyl, $C_1$–$C_6$ alkyl carbonyl, morpholino-$C_1$–$C_6$ alkyl-oxy, caroboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, $C_3$–$C_{10}$ cyclo-alkyl optionally substituted by $R^{115a}$, tetrazolyl, amidino, $-CON(R^{115b})R^{115c}$, $-SO_2N(R^{115b})R^{115c}$, $-N(R^{115b})R^{115c}$, $-SO_2R^{115d}$, $-SOR^{115d}$, $-SR^{115d}$, or $C_2$–$C_6$ alkenyl optionally substituted by $COOR^{115e}$, $R^{115a}$ represents one or two selected from the group consisting of carboxy, morpholino, morpholino-carbonyl, amino, hydroxy, cyano, $C_1$–$C_6$ alkoxy carbonyl, carbamoyl optionally substituted by cyano-$C_1$–$C_6$ alkyl, methylamino-carbonyl, dimethylamino-carbonyl, $-NH-SO_2-CH_3$, tetrazolyl, dihydrooxazolyl optionally substituted by $C_1$–$C_6$ alkyl, and 9–10 membered unsaturated condensed ring containing one N atom optionally substituted by $=O$, $R^{115b}$ represents H or $C_1$–$C_6$ alkyl, $R^{115c}$ represents H, amino, $C_1$–$C_6$ alkylamino, di($C_1$–$C_6$ alkyl)amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atom other than the adjacent N and optionally substituted by $C_1$–$C_6$ alkyl, $R^{115d}$ represents hydroxy, hydroxy $C_1$–$C_6$ alkyl, $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents one to three substituents selected from the group consisting of $C_1$–$C_6$ alkyl, amino, $C_1$–$C_6$ alkoxy, $-COOR^{118a}$ (H or $C_1$–$C_6$ alkyl), and $=O$, $R^{12}$ represents $C_1$–$C_6$ alkyl, $-(CH_2)_n-OH$, $-(CH_2)_n-CN$ (n=0, 1, 2, 3, 4, 5, or 6), $-CO-C_1$–$C_6$ alkyl, or $-C_2$–$C_6$ alkenyl, $R^{13}$ is identical to $R^{11}$, or $R^{12}$ and $R^{13}$ together with the adjacent N atom form 4–6 membered saturated heterocyclic ring which may or may not contain 1 heteroatom other than the adjacent N atom selected from the group consisting of O, N, and S the 4–6 membered heterocyclic ring optionally forms spiro with dioxacyclopentane, or is optionally fused with benzene, and/or is optionally substituted by one or two substituents selected from the group consisting of $C_1$–$C_6$ alkyl carbonyl, $C_1$–$C_6$ alkyl, hydroxy, hydroxy $C_1$–$C_6$ alkyl, carboxyl, $C_1$–$C_6$ alkoxy carbonyl, carbamoyl, phenyl, halogen substituted phenyl, $C_1$–$C_6$ alkoxy substituted phenyl, $C_1$–$C_6$ alkyl substituted phenyl, nitro phenyl, hydroxy phenyl, $C_1$–$C_6$ alkyl carbonyl phenyl, $C_1$–$C_6$ alkoxy carbonyl phenyl, pyridyl optionally substituted by $CF_3$, pyrimidyl, $C_{3-7}$ cycloalkyl, dioxolanyl, piperidino, halogen substituted phenyl carbonyl, furyl carbonyl, cyano, dimethylamino, benzyl, oxo residue, piperonyl methyl, halogen substituted diphenyl methyl, and trifluorocarbonyl amino, $R^{14}$ and $R^{15}$ are identical or different and represent H, $C_1$–$C_{10}$ alkyl, hydroxy, hydroxy $C_1$–$C_6$ alkyl, cyano $C_1$–$C_6$ alkyl, $C_3$–$C_{10}$ cycloalkyl, $C_2$–$C_{10}$ alkenyl, or $C_1$–$C_6$ alkyl carbonyl;

Y is CH or N;

$R^2$ is H, $C_1$–$C_6$ alkyl, carbamoyl, or —COOR$^{21}$
wherein $R^{21}$ is H or $C_1$–$C_6$ alkyl;

$R^3$ is thienyl, pyridyl optionally substituted by halogen or $C_1$–$C_6$ alkoxy, naphthyl optionally substituted by $C_1$–$C_6$ alkoxy, dioxane fused phenyl, dioxacyclopentane fused phenyl, or phenyl optionally substituted by one to three substituents selected from the group consisting of halogen, $C_1$–$C_6$ alkyl, nitro, amino, hydroxy, $C_1$–$C_6$ alkylthio, —OR$^{31}$, OR$^{32}$, —NR$^{33}$R$^{34}$, and —SO$_2$R$^{35}$, wherein $R^{31}$ and $R^{32}$ are identical or different and represent $C_1$–$C_6$ alkyl carbonyl, $C_1$–$C_6$ alkoxy carbonyl, $C_2$–$C_6$ alkenyl, di($C_1$–$C_6$ alkyl) amino carbonyl, $C_1$–$C_6$ alkyl amino carbonyl, —SO$_2$—R$^{311}$, or straight- or branched-$C_1$–$C_6$ alkyl optionally substituted by $R^{312}$, cyclo-$C_3$–$C_7$ alkyl optionally substituted by $R^{312}$, $R^{311}$ represents $C_1$–$C_6$ alkyl, amino, di($C_1$–$C_6$ alkyl) amino $C_1$–$C_6$ alkyl amino, $C_1$–$C_6$ alkoxy carbonyl $C_1$–$C_6$ alkyl amino, or 5–6 membered saturated hetero cyclic ring containing up to 2 heteroatoms of N, S, and/or O and optionally substituted by $C_1$–$C_6$ alkyl or carboxy, $R^{312}$ represents $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by one or three substituents selected from the group consisting of $C_1$–$C_6$ alkyl, carbamoyl, and di($C_1$–$C_6$ alkyl)amino, $R^{33}$ represents H or $C_1$–$C_6$ alkyl, $R^{34}$ represents carboxy $C_1$–$C_6$ alkyl carbonyl, $C_1$–$C_6$ alkyl carbonyl, or $C_1$–$C_6$ alkyl optionally substituted by $R^{341}$, wherein $R^{341}$ represents dimethylamino, $C_1$–$C_6$ alkoxy, morpholino, phenyl, $C_1$–$C_6$ alkyl substituted piperazino, oxopyrrolidino, or imidazolyl, or —N $R^{33}R^{34}$ forms 5–6-membered saturated hetero cyclic ring optionally containing one more hetero atom selected from the group consisting of N, S, and O and optionally substituted by $C_1$–$C_6$ alkyl, $R^{35}$ represents amino, di($C_1$–$C_6$ alkyl)amino $C_1$–$C_6$, alkyl amino, piperazino optionally substituted by hydroxy $C_1$–$C_6$ alkyl or $C_1$–$C_6$ alkyl, $C_1$–$C_6$ alkoxy carbonyl $C_1$–$C_6$ alkyl amino, morpholino, piperidino optionally substituted by carboxy or $C_1$–$C_6$ alkyl, or hydroxy $C_1$–$C_6$ alkyl amino, or its tautomeric or stereoisomeric form, or its physiologically acceptable salt.

The compound of the present invention surprisingly show excellent Syk tyrosine kinase inhibitory activity. They are therefore suitable especially as Syk tyrosine kinase inhibitors and in particular for the production of medicament or medical composition, which may be useful to treat Syk tyrosine kinase dependent diseases.

More specifically, since the compounds of the present invention inhibit Syk tyrosine kinase activity, they are useful for treatment and prophylaxis of diseases involving Syk tyrosine kinase activity as follows: those caused by allergic or inflammatory reaction which include allergic diseases, such as asthma, allergic rhinitis, atopic dermatitis, food allergy, contact allergy, hives, conjunctivitis, and vernal catarrh; autoimmune diseases, such as chronic arthrorheumatism, systemic lupus erythematosus, and psoriasis; diabrotic diseases including diabrotic colitis; fibrous diseases; tumor and the like.

The compounds of the present invention are also useful for treatment and prophylaxis of diseases: those caused by immune reaction including rejections or graft versus host disease upon organ transplantation; those caused by antibody-dependent cellular cytotoxicity, such as autoimmune hemolytic anemia, myasthenia gravis; thrombus caused by platelet agglutination; obesity; and Alzheimer disease, since all of the diseases described also relate to Syk tyrosine kinase activity.

Preferred compounds of formula (I) are those wherein:

$R^1$ is —OR$^{11}$, —SR$^{11}$, —NHR$^{11}$, or —NR$^{12}$R$^{13}$, $R^{11}$ represents H, phenyl carbonyl, thienyl optionally substituted by COOR$^{111}$ (R$^{111}$ is H or $C_1$–$C_6$ alkyl), pyrimidyl, $C_2$–$C_6$ alkenyl, imidazolyl optionally substituted by $C_1$–$C_6$ alkyl, triazolyl optionally substituted by $C_1$–$C_6$ alkyl, tetrazolyl optionally substituted by $C_1$–$C_6$ alkyl, thiadiazolyl optionally substituted by $C_1$–$C_6$ alkyl, pyrrolidinyl optionally substituted by $C_1$–$C_6$ alkyl, cyclohexenyl, $C_1$–$C_{10}$ straight- or branched-alkyl optionally substituted by $R^{112}$, $R^{113}$ and/or $R^{114}$, $C_3$–$C_{10}$ cyclo-alkyl optionally substituted by $R^{112}$, $R^{113}$ and/or $R^{114}$, phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 hetero atoms selected from the group consisting of N and S and optionally substitued by $R^{118}$, $R^{112}$ represents halogen, amino, —COOR$^{112a}$ (R$^{112a}$ represents H or $C_1$–$C_6$ alkyl) —CO—NH—CH$_3$, —CO—NH—(CH$_2$)$_p$CN, —NH—COOR$^{112a}$, pyrazinyl, tetrazolyl, dihydrothiophenyl, morpholino, piperidino, di($C_1$–$C_6$ alkyl)amino, indolyl, pyridinyl, thiophenyl, or phenyl optionally substituted by one substituent selected from the group consisiting of halogen, hydroxy, $C_1$–$C_6$ alkoxy, and trihalogen substituted methyl, $R^{113}$ represents halogen, hydroxy, or $C_1$–$C_6$ alkoxycarbonyl, $R^{114}$ represents halogen, $R^{115}$ represents H, halogen, amino, hydroxy, nitro, cyano, carboxy, $C_1$–$C_6$ alkoxycarbonyl, $C_1$–$C_6$ alkoxy, $C_1$–$C_6$ alkyl carbonyl, morpholino-$C_1$–$C_6$ alkyl-oxy, carboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, $C_3$–$C_{10}$ cyclo-alkyl optionally substituted by $R^{115a}$, tetrazolyl, amidino, —CON(R$^{115b}$)R$^{115c}$, —SO$_2$N(R$^{115b}$)R$^{115c}$, —N(R$^{115b}$)R$^{115c}$, —SO$_2$R$^{115d}$, —SOR$^{115d}$, —SR$^{115d}$, or $C_2$–$C_6$ alkenyl optionally substituted by COOR$^{115e}$, $R^{115a}$ presents one or two selected from the group consisting of carboxy, morpholino, morpholino-carbonyl, amino, hydroxy, cyano, $C_1$–$C_6$ alkoxy carbonyl, carbamoyl optionally substituted by cyano-$C_1$–$C_6$ alkyl, methylamino-carbonyl, dimethylamino-carbonyl, —NH—SO$_2$—CH$_3$, tetrazolyl, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, $C_1$–$C_6$ alkyl amino, di($C_1$–$C_6$ alkyl)amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl)

amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atoms other than the adjacent N and optionally substituted by $C_1$–$C_6$ alkyl, $R^{115d}$ represents hydroxy, hydroxy $C_1$–$C_6$ alkyl, $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents one to three substituents selected from the group consisting of $C_1$–$C_6$ alkyl, amino, $C_1$–$C_6$ alkoxy, COOR$^{118a}$ (H or $C_1$–$C_6$ alkyl), and =O $R^{12}$ represents $C_1$–$C_6$ alkyl, —(CH$_2$)$_q$—OH, —(CH$_2$)$_q$—CN (q=0, 1, 2, 3, 4, 5, or 6), —CO—$C_1$–$C_6$ alkyl, or —$C_2$–$C_6$ alkenyl, $R^{13}$ is identical to $R^{11}$, or $R^{12}$ and $R^{13}$ together with the adjacent N atom form 4–6 membered saturated heterocyclic ring which may or may not contain 1 heteroatom other than the adjacent N atom selected from the group consisting of O, N, and S, the 4–6 membered heterocyclic ring optionally forms spiro with dioxacyclopentane, or is optionally fused with benzene, and/or is optionally substituted by one or two substituents selected from the group consisting of $C_1$–$C_6$ alkyl, $C_1$–$C_6$ alkyl carbonyl, hydroxy, hydroxy $C_1$–$C_6$ alkyl, carboxyl, $C_1$–$C_6$ alkoxy carbonyl, carbamoyl, phenyl, halogen substituted phenyl, $C_1$–$C_6$ alkoxy substituted phenyl, $C_1$–$C_6$ alkyl substituted phenyl, nitro phenyl, hydroxy phenyl, $C_1$–$C_6$ alkyl carbonyl phenyl, $C_1$–$C_6$ alkoxy carbonyl phenyl, pyridyl optionally substituted by $CF_3$, pyrimidyl, $C_{3-7}$ cycloalkyl, dioxolanyl, piperidino, halogen substituted phenyl carbonyl, furyl carbonyl, cyano, dimethylamino, benzyl, oxo residue, piperonyl methyl, halogen substituted diphenyl methyl, and trifluorocarbonyl amino, Y is CH or N;

$R^2$ is H, $C_1$–$C_6$ alkyl, or carbamoyl;

$R^3$ is thienyl, pyridyl optionally substituted by halogen or $C_1$–$C_6$ alkoxy, dioxane fused phenyl, dioxacyclopentane fused phenyl, or phenyl optionally substituted by one to three substituents selected from the group consisting of halogen, $C_1$–$C_6$ alkyl, nitro, amino, hydroxy, $C_1$–$C_6$ alkylthio, —OR$^{31}$, —OR$^{32}$, —NR$^{33}$R$^{34}$, and —SO$_2$R$^{35}$, wherein $R^{31}$ and $R^{32}$ are identical or different and represent nitro, $C_1$–$C_6$ alkyl carbonyl, $C_1$–$C_6$ alkoxy carbonyl, $C_2$–$C_6$ alkenyl, di($C_1$–$C_6$ alkyl) amino carbonyl, $C_1$–$C_6$ alkyl amino carbonyl, —SO$_2$—R$^{311}$, or straight- or branched-$C_1$–$C_6$ alkyl optionally substituted by $R^{312}$, cyclo-$C_3$–$C_7$ alkyl optionally substituted by $R^{312}$, $R^{311}$ represents $C_1$–$C_6$ alkyl, amino, di($C_1$–$C_6$ alkyl) amino $C_1$–$C_6$ alkyl amino, $C_1$–$C_6$ alkoxy carbonyl $C_1$–$C_6$ alkyl amino, 5–6 membered saturated hetero cyclic ring containing up to 2 heteroatoms of N, S, and/or O and optionally substituted by $C_1$–$C_6$ alkyl or carboxy, $R^{312}$ represents one selected from the group consisting of $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by $C_1$–$C_6$ alkyl, carbamoyl, or di($C_1$–$C_6$ alkyl) amino, $R^{33}$ represents H or $C_1$–$C_6$ alkyl, $R^{34}$ represents carboxy $C_1$–$C_6$ alkyl carbonyl, $C_1$–$C_6$ alkyl carbonyl, $C_1$–$C_6$ alkyl optionally substituted by $R^{341}$, wherein $R^{341}$ represents dimethylamino, $C_1$–$C_6$ alkoxy, morpholino, phenyl, $C_1$–$C_6$ alkyl substituted piperazino, oxopyrrolidino, or imidazolyl, or —N R$^{33}$R$^{34}$ forms morpholino optionally substituted by $C_1$–$C_6$ alkyl, thiazinano optionally substituted by $C_1$–$C_6$ alkyl, piperidino optionally substituted by $C_1$–$C_6$ alkyl, or pyrrolidino optionally substituted by $C_1$–$C_6$ alkyl, $R^{35}$ represents amino, di($C_1$–$C_6$ alkyl)amino $C_1$–$C_6$ alkyl amino, hydroxy $C_1$–$C_6$ alkyl amino, $C_1$–$C_6$ alkoxy carbonyl $C_1$–$C_6$ alkyl amino, morpholino, piperazino optionally substituted by hydroxy $C_1$–$C_6$ alkyl or $C_1$–$C_6$ alkyl, or piperidino optionally substituted by carboxy, or its tautomeric or stereoisomeric form, or its physiologically acceptable salt.

More preferred compounds of Formula (I) are those wherein:

$R^1$ represents —OR$^{11}$, —SR$^{11}$, or —NHR$^{11}$, $R^{11}$ represents phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 N atoms and optionally substitued by $R^{118}$, $R^{115}$ represents H, halogen, amino, hydroxy, nitro, cyano, carboxy, $C_1$–$C_6$ alkoxycarbonyl, $C_1$–$C_6$ alkoxy, $C_1$–$C_6$ alkyl carbonyl, morpholino-$C_1$–$C_6$ alkyl-oxy, carboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, or $C_3$–$C_{10}$ cyclo-alkyl optionally substituted by $R^{115a}$, tetrazolyl, amidino, —CON(R$^{115b}$)R$^{115c}$, —SO$_2$N(R$^{115b}$)R$^{115c}$, —N(R$^{115b}$)R$^{115c}$, —SO$_2$R$^{115d}$, —SOR$^{115d}$, —SR$^{115d}$, or $C_2$–$C_6$ alkenyl optionally substituted by COOR$^{115e}$, $R^{115a}$ represents one or two selected from the group consisting of morpholino, morpholino-carbonyl, amino, hydroxy, cyano, $C_1$–$C_6$ alkoxy carbonyl, carbamoyl, methylamino-carbonyl, dimethylamino-carbonyl, —NH—SO$_2$—CH$_3$, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atoms other than the adjacent N and optionally substituted by $C_1$–$C_6$ alkyl, $R^{115d}$ represents $C_1$–$C_6$ alkyl, hydroxy, hydroxy $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents $C_1$–$C_6$ alkyl, amino, $C_1$–$C_6$ alkoxy, COOR$^{118a}$ (R$^{118a}$ is H or $C_1$–$C_6$ alkyl), or =O (mono or di), Y is CH or N;

$R^2$ is H;

$R^3$ is phenyl optionally substituted by two substituents selected from the group consisting of $-OR^{31}$, $-OR^{32}$, and $-NR^{33}R^{34}$, wherein $R^{31}$ and $R^{32}$ are identical or different and represent straight- or branched-$C_1$-$C_6$ alkyl optionally substituted by $R^{312}$, cyclo-$C_3$-$C_7$ alkyl optionally substituted by $R^{312}$, $R^{312}$ represents one selected from the group consisting of $C_1$-$C_6$ alkoxy, halogen, phenyl optionally substituted by $C_1$-$C_6$ alkoxy, di($C_1$-$C_6$ alkyl) amino, $C_1$-$C_6$ alkyl and hydroxy $C_1$-$C_6$ alkyl substituted amino, or 5–6 membered saturated hetero ring containing up to 2 heteroatoms of N, S, and/or O and optionally substituted by $C_1$-$C_6$ alkyl, carbamoyl, or di($C_1$-$C_6$ alkyl) amino $R^{33}$ represents H, or $C_1$-$C_6$ alkyl, $R^{34}$ represents $C_1$-$C_6$ alkyl optionally substituted by $C_1$-$C_6$ alkoxyl, or $-N R^{33}R^{34}$ forms morpholino optionally substituted by $C_1$-$C_6$ alkyl, or its tautomeric or stereoisomeric form, or its physiologically acceptable salt.

The most preferable compounds of the present invention are as follows:

[7-(3,4-Dimethoxy-phenyl)-imidazo[1,2-c]pyrimidin-5-yl]-(1H-indazol-6-yl)-amine;
2-[7-(3,4-Dimethoxy-phenyl)-imidazo[1,2-c]pyrimidin-5-ylamino]-benzamide;
2-[7-(3,4-Dimethoxy-phenyl)-imidazo[1,2-c]pyrimidin-5-ylamino]-5-methoxy-benzamide;
2-[7-(3,4-Dimethoxy-phenyl)-imidazo[1,2-c]pyrimidin-5-ylamino]-benzenesulfonamide;
[7-(3,4-Dimethoxy-phenyl)-[1,2,4]triazolo[1,5-c]pyrimidin-5-yl]-(1H-indazol-6-yl)-amide;
4-Amino-2-[7-(3,4-dimethoxy-phenyl)-imidazo[1,2-c]pyrimidin-5-ylamino]-benzamide;
(7-(3-methoxy-4-[(2-methoxy-ethyl)-methyl-amino]-phenyl)-imidazo[1,2-c]pyrimidin-5-yl)-(4-methoxy-phenyl)-amine;
[7-(3-Methoxy-4-morpholin-4-yl-phenyl)-imidazo[1,2-c]pyrimidin-5-yl]-p-tolyl-amine;
(2-Methanesulfonyl-phenyl)-(7-(3-methoxy-4-[(2-methoxy-ethyl)-methyl-amino]-phenyl)-imidazo[1,2-c]pyrimidin-5-yl)-amine;
2-[7-(3-Methoxy-4-morpholin-4-yl-phenyl)-imidazo[1,2-c]pyrimidin-5-ylamino]-nicotinamide;
2-[7-(3-Methoxy-4-morpholin-4-yl-phenyl)-imidazo[1,2-c]pyrimidin-5-ylamino]-benzamide;
2-Methanesulfonyl-phenyl)-[7-(3-methoxy-4-morpholin-4-yl-phenyl)-imidazo[1,2-c]pyrimidin-5-yl]-amine;
4-[7-(3-Methoxy-4-morpholin-4-yl-phenyl)-imidazo[1,2-c]pyrimidin-5-ylamino]-phenol;
[7-(3-Methoxy-4-morpholin-4-yl-phenyl)-imidazo[1,2-c]pyrimidin-5-yl]-(4-methoxy-phenyl)-amine; and
2-[7-(3,4-Dimethoxy-phenyl)-imidazo[1,2-c]pyrimidin-5-ylamino]-nicotinamide or its tautomeric or stereoisomeric form, or its physiologically acceptable salt.

The compound of the formula (I) or salts thereof of the present invention can be, but not limited to be, prepared by the methods [A]–[F] below.

[A] The compound (Ia):

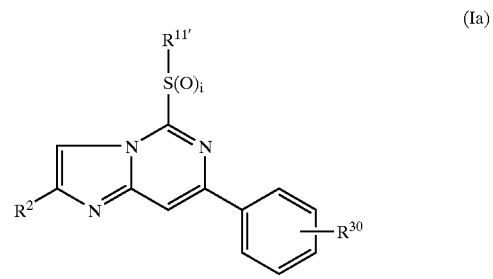

(Ia)

wherein $R^2$ are the same as defined above; i represent 0, 1, or 2; $R^{11'}$ represents $C_1$-$C_6$ alkyl; and $R^{30}$ represents optional substituents on the 1, 2, and/or 3 positions of phenyl including hydrogen, OMe, methyl, halogen, and/or morpholino, or a salt thereof can be obtained, for example, by the following process.

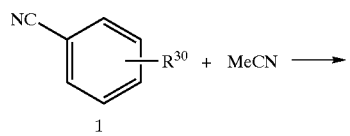

1

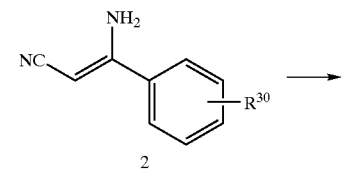

2

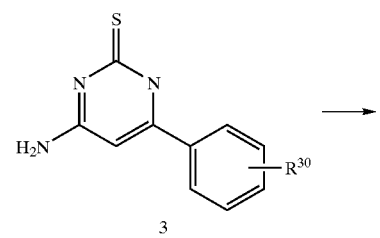

3

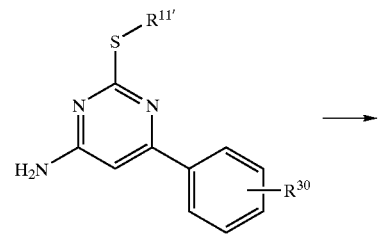

4

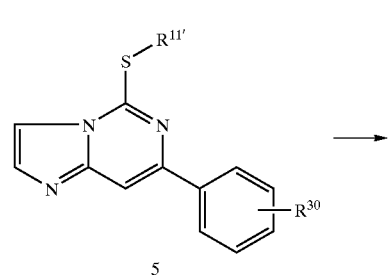

5

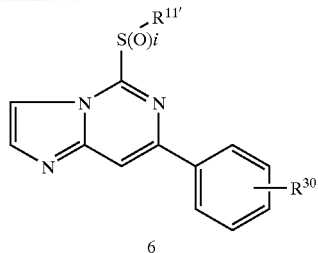

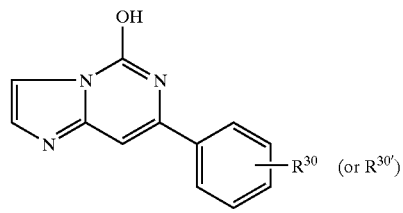

wherein $R^{30}$ and $R^{30'}$ are the same as defined above.

The reaction maybe be carried out by treating compound (Ia) or (Ib) with an aqueous solution of base of 2–5 equivalents on molar base (for example NaOH or KOH) in methanol or ethanol with heating for 5–6 hours.

Compound (IIa):

Compound 1, optionally substituted benzonitrile, is commercially available or can be synthesized from common chemical reagents by conventional methods.

Compound 1 can be replaced by thienyl nitrile, optionally substituted naphtyl nitrile, optionally substituted pyridyl nitrile, dioxane fused phenyl nitrile, or dioxacyclopentane fused phenyl nitrile to produce the compound different at C-7 position from the formula (IIa).

Compound 2 may be prepared by reacting the anion of $CH_3CN$, which is generated by treating acetonitrile with base e.g., LDA, with Compound 1. The reaction may be carried out in ether solvents, such as diethylether or THF at −78° C. to room temperature overnight.

Compound 3 may be prepared by reacting compound 2 with thiourea in the presence of base, e.g., sodium alkoxide with heating in alcohol solvent overnight.

Compound 4, wherein $R^{11'}$ represents $C_1$–$C_6$ alkyl may be prepared by alkylating compound 3. Alkylation may be carried out by treating compound 3 in an appropriate solvent with alkyl halides, such as $C_2H_5I$, $CH_3I$, $C_2H_5Br$, and $CH_3Br$ in the presence of base e.g., inorganic bases such as $NaHCO_3$ and $Na_2CO_3$, or organic base such as triethylamine at room temperature for 2 hours to overnight.

Compound 5 may be prepared by treating compound 4 with 2–5 equivalents of halogen acetaldehyde e.g., bromoacetaldehyde, or halogen acetal, e.g., bromoacetal, or equivalents thereof. The reaction may be carried out for example in THF-water with heating for 3 hours to overnight.

Alternatively, compound 4 can be treated with an alpha-halogen substituted ketone or equivalent thereof to ultimately produce 2' substituted compound of the formula (I) of the present invention.

Compound 6 is prepared by oxidizing compound 5 by conventional methods.

[B] The compound of the formula (Ib) below:

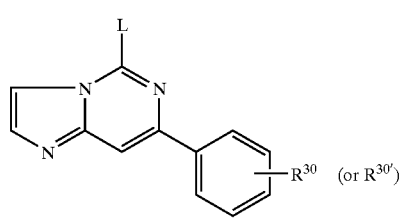

wherein $R^{30'}$ represents optional substituents on the 1,2, and/or 3 positions of phenyl including, but not limited to, $SO_2R^{35}$ (wherein $R^{35}$ is the same as defined) can be prepared by modifying $R^{30}$ of the formula (Ia) above with the use of common chemical reagents by conventional methods.

[C] Intermediates for further variation

The compound (Ia) and (Ib) above can be hydrolyzed to synthesize intermediate compound 7 below:

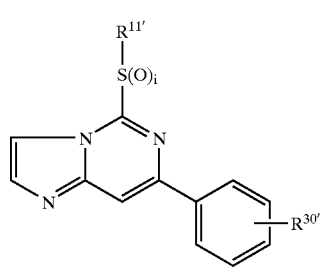

(wherein L is a leaving group and may be represents, for instance, halogen atom e.g., chlorine, bromine or iodine atom; $C_6$–$C_{10}$ arylsulfonyloxy group e.g., benzenesulfonyloxy, polysulfonyloxy, or p-toluenesulfonyloxy; and $C_1$–$C_4$ alkylsulfonyloxy group e.g., methanesulfonyloxy, and the like.halogen) may be prepared by reacting compound 7 with an appropriate halogenating reagent (for example $POCl_3$, $PCl_5$, $SOCl_2$ etc.) or corresponding sulfonyl chloride or the like in the presence of a base.

[D] A general method of producing the intermediate shown by the formula (IIb) or salts thereof as used in preparing the compound of the formula (I) or salts thereof is mentioned below.

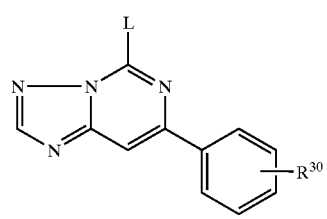

wherein $R^{30}$ and L are the same as defined above.

The compounds of formula (IIb) can be synthesized by the following route;

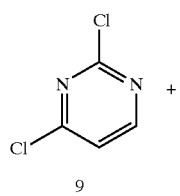

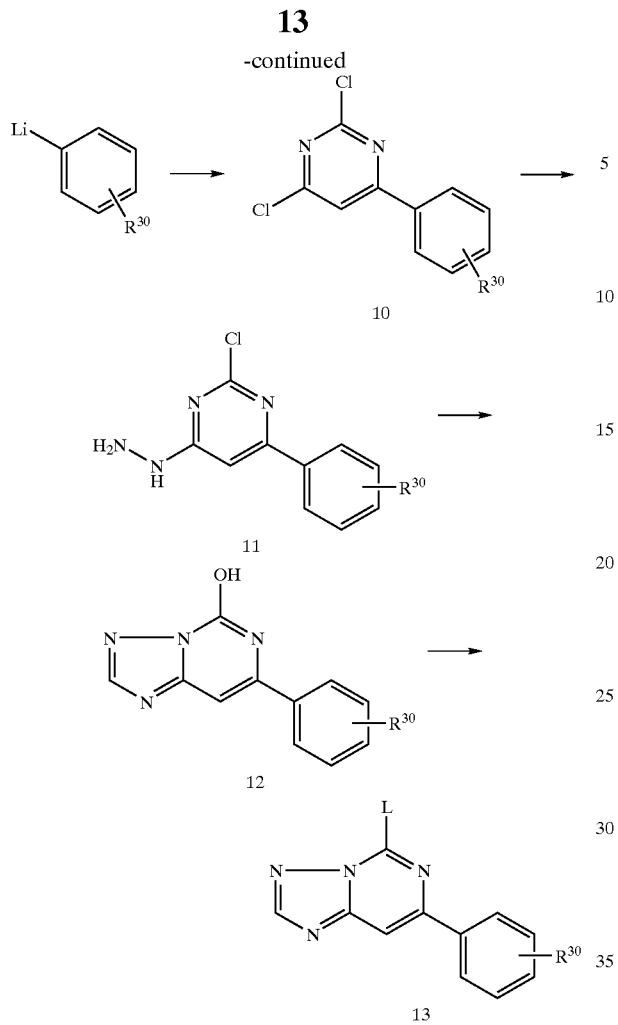

[E] The compound (Ie):

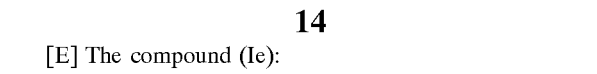

wherein $R^2$, $R^3$ and Y are the same as defined above and $R^{1'}$ represents $-OR^{11}$, $-NHR^{11}$, $-SR^{11"}$, $-SO_2R^{11"}$, $-SOR^{11"}$, or $-NR^{12}R^{13}$ (wherein $R^{11}$, $R^{12}$, and $R^{13}$ are the same as defined above; $R^{11"}$ is identical to $R^{11}$ but $C_1$–$C_6$ alkyl) or a salt thereof can be obtained, for example, by reacting a compound shown by the general formula (II):

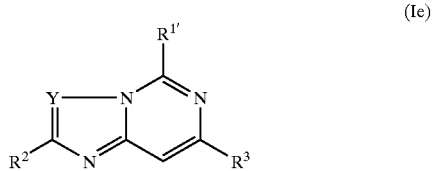

wherein Y, $R^2$, $R^3$, and L are the same defined as defined above, or a salt thereof, with a compound shown by the general formula (III):

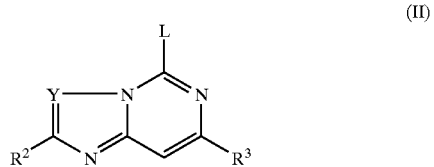

or a salt thereof.

This reaction can be carried out without solvent or in a solvent including, for instance, alcohols such as methanol and ethanol; ethers, such as dioxane, diethyl ether, and tetrahydrofuran (THF); aromatic hydrocarbons such as benzene, toluene and xylene; nitriles such as acetonitrile; amides such as dimethylformamide (DMF) and dimethylacetamide; sulfoxides such as dimethyl sulfoxide, and others.

The amount of the compound shown by the formula (III) or a salt thereof per mole of the compound shown by the formula (II) or the salt thereof as used in the reaction is, usually ⅕ to 5 moles and preferably about ½ to 2 moles.

The reaction temperature can be optionally set depending on the compounds to be reacted. The reaction temperature is usually, but not limited to, about 10° C. to 200° C. and preferably about 20° C. to 100° C. The reaction may be conducted for, usually, 30 minutes to 48 hours and preferably 1 to 24 hours.

Some reaction can be advantageously conducted in the presence of a base. Examples of the base include an alkali metal hydride such as sodium hydride or potassium hydride; alkali metal alkoxide such as sodium methoxide or sodium ethoxide; alkali metal hydroxide such as sodium hydroxide or potassium hydroxide; carbonates such as sodium carbonate or potassium carbonate, and hydrogen carbonates such as sodium hydrogen carbonate and potassium hydrogen carbonate; organic amines such as triethylamine.

Compound 10 can be prepared by reacting 2,4-dichloropyrimidine (Compound 9) with aryl lithium reagent, which is generated in situ by treating aromatic halogen (for example, Cl, Br, I) with n-butyl lithium. The reaction can be carried out in ether solvents (such as diethyl ether or THF) at −78° C. to 50° C. for 5 to 24 hours. (The aromatic halogens are commercially available or can be synthesized from common chemical reagents by conventional methods.)

Compound 11 can be prepared by treating compound 10 with hydrazine hydrate or anhydrous hydrazine in appropriate solvent (for example, CHCl₃, THF etc.). The reaction can be carried out by treating compound 10 with 5–30 equivalents of hydrazine hydrate or anhydrous hydrazine in CHCl₃ or THF at 0° C. to 100° C. for 5–24 hours.

Compound 12 can be prepared by reacting Compound 11 with carboxylic acid or orth-acid ester. The reaction can be carried out using carboxylic acid, or orth-acid ester as solvent at 50° C. to 200° C. for 3 to 20 hours.

Compounds 13 (where L=aryl or alkyl sulfonyloxy) can be prepared by reacting compound 12 with the corresponding sulfonyl chloride in the presence of a base.

Compound 13 (where L=halogen) can be prepared by reacting compound 12 with appropriate halogenating reagent (for example POCl₃, PCl₅, SOCl₂, etc.) in the presence of a base. The reaction may be typically carried out, without limitation, using the halogenating reagent as the solvent under reflux condition for 3 to 5 hours.

[F] Alternatively, the compound of the formula (If) below:

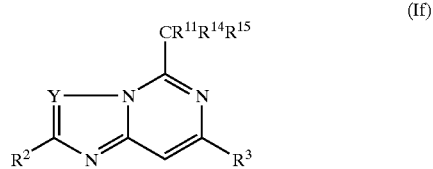

(If)

wherein $R^2$, $R^3$, $R^{11}$, $R^{14}$ and $R^{15}$ are the same as defined above, can be prepared by reacting a compound shown by a compound of the formula (II) with Grignard reagent or according to the known conventional methods.

When the compound shown by the formula (I) or a salt thereof has tautomeric isomers and/or stereoisomers (e.g., geometrical isomers and conformational isomers), each of their separated isomer and mixtures are also included in the scope of the present invention.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, depending on its substituents, may be modified to form lower alkylesters or known other esters; and/or hydrates or other salvates. Those esters, hydrates, and salvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefor. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely devided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

The effect of the present compounds were examined by the following assays and pharmacological tests.

[Syk Tyrosine Kinase Inhibitory Assay]
(1) Preparation of Syk Protein

A cDNA fragment encoding human Syk openreading frame was cloned from total RNA of human Burkitt's lymphoma B cell lines, Raji (American Type Culture Collection), with the use of RT-PCR method. The cDNA fragment was inserted into pAcG2T (Pharmingen, San Diego, Calif.) to construct a baculovirus transfer vector. Then the vector, together with the linearized baculovirus (BaculoGold™, Pharmingen), was used to transfect Sf21 cells (Invitrogen, San Diego, Calif.).

Generated recombinant baculovirus was cloned and amplified in Sf21 cells. Sf21 cells were infected with this amplified high titer virus to produce a chimeric protein of Syk kinase fused by glutathione-S-transferase (GST).

The resulting GST-Syk was purified with the use of glutathione column (Amersham Pharmacia Biotech AB, Uppsala, Sweden) according to the manufacturer's instruction. The purity of the protein was confirmed to be more than 90% by SDS-PAGE.

(2) Synthesize of a Peptide

Next, a peptide fragment of 30 residues including two tyrosine residues, KISDFGLSKALRADENYYKAQTHGKWPVKW, was synthesized by a peptide synthesizer. The N-terminal of the fragment was then biotinylated to obtain biotinylated activation loop peptide (AL).

(3) The Measurement of Syk Tyrosine Kinase Activity

All reagents were diluted with the Syk kinase assay buffer (50 mM Tris-HCl (pH 8.0), 10 mM $MgCl_2$, 0.1 mM $Na_3VO_4$, 0.1% BSA, 1 mM DTT). First, a mixture (35 µl) including 3.2 µg of GST-Syk and 0.5 µg of AL was put in each well in 96-well plates. Then 5 µl of a test compound in the presence of 2.5% dimethylsulfoxide (DMSO) was added to each well. To this mixture was added 300 µM ATP (10 µl) to initiate the kinase reaction. The final reaction mixture (50 µl) consists of 0.65 nM GST-Syk, 3 µM AL, 30 µM ATP, a test compound, 0.25% DMSO, and a Syk kinase assay buffer.

The mixture was incubated for 1 hr at room temperature, and the reaction was terminated by the addition of 120 µl of termination buffer (50 mM Tris-HCl (pH 8.0), 10 mMEDTA, 500 mM NaCl, 0.1% BSA). The mixture was transferred to streptavidin-coated plates and incubated for 30 min at room temperature to combine biotin-AL to the plates. After washing the plates with Tris-buffered saline (TBS) (50 mM Tris-HCl (pH 8.0), 138 mM NaCl, 2.7 mM KCl) containing 0.05% Tween-20 for 3 times, 100 µl of antibody solution consisting of 50 mM Tris-HCl (pH 8.0), 138 mM NaCl, 2.7 mM KCl, 1% BSA, 60 ng/ml anti-phosphotyrosine monoclonal antibody, 4G10 (Upstate Biotechnology), which is labeled with europium by Amersham Pharmacia's kit in advance, was added and incubated at room temperature for 60 min. After washing, 100 µl of enhancement solution (Amersham pharmacia Biotech) was added and then time-resolved fluorescence was measured by multi-label counter ARVO (Wallac Oy, Finland) at 340 nm for excitation and 615 nm for emission with 400 msec of delay and 400 msec of window.

[Src Kinase Inhibitory Assay]
(1) Preparation of Src and its Substrate

Human Src kinase was purchased from Upstate Biotechnology (Lake Placid, N.Y.).

The cDNA fragment encoding T cell receptor zeta-chain (Zeta) was obtained from a Jurkat cDNA library. Then Zeta was expressed as a fusion protein with poly histidine-tag (His-Zeta) in E. coli and purified by nickel resign as described in the instruction of His-tag purification kit (Novagen, Madison, Wis.).

His-Zeta was diluted with TBS to prepare solution with the concentration of 10 µg/ml. The resulting solution (100 µl) was put in an each well of a nickel plate. Plates were incubated for overnight at 4° C. to coat the surface of the well with His-Zeta.

After washing the plate with 0.05% Tween-20 containing TBS for 3 times, 35 µl of reaction mixture containing 0.1 ng Src was put into an each well of a His-Zeta coated nickel plate. Then, 5 µl of a test compound in the presence of 2.5% DMSO was added to each well. To this mixture was added 10 µl of 100 µM ATP to initiate the kinase reaction. Final mixture consists of 0.1 ng Src, a test compound, 0.25% DMSO, 10 µM ATP in the Src kinase assay buffer (50 mM Hepes (pH 7.4.), 10 mM $MgCl_2$, 0.125% BSA). The mixture was incubated for 45 min at RT with gentle shaking, and the reaction was terminated by washing the wells. To detect the phosphorylation of His-Zeta, 100 µl of antibody solution with europium-labeled 4G10 was added and time-resolved fluorescence was measured as mentioned above.

[The Measurement of Hexosaminidase Release from RBL-2H3 Cells]

RBL-2H3 cells were maintained in minimum essential medium supplemented by 15% FCS, penicillin G sodium (100 units/ml), and streptomycin sulfate (100 units/ml). Thirty two thousand ($3.2 \times 10^4$) cells were seeded in each well of 96 well plate and cultured for more than 24 hr in the presence of 0.3 µg/ml of anti-dinitrophenol (DNP) monoclonal mouse IgE (SPE-7: Sigma-Aldrich Corp., St. Louis, Mo.). After the gentle washing of the wells with PIPES buffer (25 mM PIPES, 125 mM NaCl, 2.7 mM KCl, 5.6 mM glucose, 1 mM $CaCl_2$, 0.1% BSA, pH 7.4), cells were treated with a test compound (45 µl) in the presence of 0.3% DMSO for 15 min at 37° C. and then stimulated with 5 µl of DNP-conjugated bovine serum albumin (DNP-BSA, Sigma-Aldrich) with the concentration of 0.1 µg/ml for further 45 min at 37° C. The supernatant (20 µl) was recovered and incubated with equal volume of 1 mM p-nitrophenyl-β-D-glucosaminidase in 0.1 M sodium citrate (pH 4.5) for 1 hr at 37° C. to detect the amount of released hexosaminidase. The reaction of hexosaminidase was terminated by the addition of 200 μl of 0.1 M Na₂CO₃/0.1 M NaHCO₃ (pH 10) and the absorbance at OD₄₁₀ was measured to determine the amount of release of hexosaminidase.

[Passive Cutaneous Anaphylaxis (PCA) Test in Rats]

6 Weeks old male Wistar rats were sensitized intradermally (i.d.) on their shaved backs with 50 μl of 0.1 μg/ml mouse anti-DNP IgE monoclonal antibody (SPE-7) under a light anesthesia. After 24 hours, the rats were challenged intravenously with 1 ml of saline containing 0.6 mg DNP-BSA (30) (LSL CO., LTD) and 0.005 g of Evans blue. Compounds were injected intraperitoneally (i.p.) 0.5 hr prior to antigen injection. Rats without the sensitization, challenge, and compound treatment were used for a blank (control) and rats with sensitization, challenge and vehicle treatment were used to determine a value without inhibition. Thirty min after the challenge, the rats were killed, and the skin of the back was removed. Evans blue dye in the skin was extracted in formamide overnight at 63° C. Then an absorbance at 620 nm was measured to obtain the optical density of the leaked dye.

Percent inhibition of PCA with a compound was calculated as follows:

% inhibition={(mean vehicle value−sample value)/(mean vehicle value−mean control value)}×100

[Anaphylactic Bronchoconstriction in Rats]

6 Weeks old male Wistar rats were sensitized intravenously (i v.) with 10 μg mouse anti-DNP IgE, SPE-7, and 1 days later, the rats were challenged intravenously with 0.3 ml of saline containing 1.5 mg DNP-BSA (30) under anesthesia with urethan (1000 mg/kg, i.p.) and gallamine (50 mg/kg, i.v.). The trachea was cannulated for artifical respiration (2 ml/stroke, 70 strokes/min). Pulmonary inflation pressure (PIP) was recorded through a side-arm of cannula connected to pressure transducer. Change in PIP reflect change of both resistance and compliance of the lungs. To evaluate the drugs, each drug was given i.v. 5 min before challenge.

In vitro test results are shown in the tables of the Examples below. The data corresponds to the compounds as yielded by solid phase synthesis and thus to levels of purity of about 40 to 90%. For practical reasons, the compounds are grouped in four classes of activity as follows:

$IC_{50}$=A≦0.5 μM<B≦2 μM<C≦10 μM<D

The compounds of the present invention also show excellent selectivity, and strong activity in vivo assays.

EXAMPLES

The present invention will be described in detail below in the form of examples, but they should by no means be construed as defining the metes and bounds of the present invention.

In the examples below, all quantitative data, if not stated otherwise, relate to percentages by weight. The mass determinations were carried out by MAT95 (Finnigan MAT).

Example 1

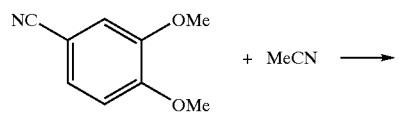
+ MeCN ⟶

-continued

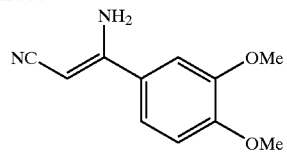

To a solution of diisopropylamine (52.7 g, 521 mmol) in THF (1 L) at −78° C. was added n-BuLi (1.6 M in hexane, 272 ml, 435 mmol) over 15 min. Acetonitrile (18.8 g, 460 mmol) in THF (200 m) was added to the LDA (Lithium diisopropylamide) solution over 15 min. to create a white precipitate. The resulting mixture was stirred for 30 min at −78° C. and was then treated with a solution of 3,4-dimethoxybenzonitrile (50 g, 306 mmol) in THF (200 ml). The resulting mixture was stirred at −78° C. for 20 min., and then allowed to slowly warm to room temperature to afford a clear orange solution. The solution was stirred at room temperature overnight. Water (300 ml) was added to the reaction mixture. The solution was partially concentrated under reduced pressure, and then separated between water and $CH_2Cl_2$. The organic phase was washed with brine and dried over $Na_2SO_4$. Concentrated under reduced pressure to give the crude product which was purified by recrystalization from MeOH. Two crops were obtained. (total 50.0 g, 80% yield)

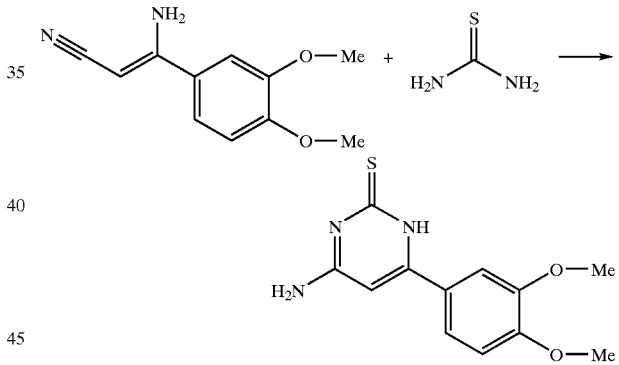

To a solution of sodium ethoxide in ethanol [prepared from sodium (11.3 g, 490 mmol) and ethanol (240 ml)] was added thiourea (28.0 g, 367 mmol) and alpha cinnamonitrile (50 g, 245 mmol). The resulting mixture was heated under reflux overnight. The mixture was cooled to room temperature and diluted with water (300 ml), and then neutralized with 1N HCl. The resulting precipitate was filtered and washed with water and then THF. (64 g, quant.)

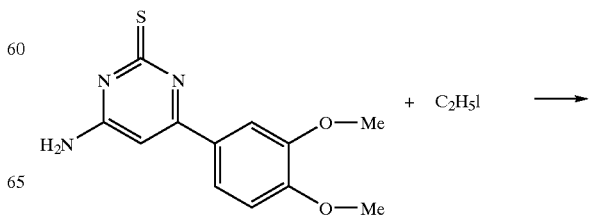

-continued

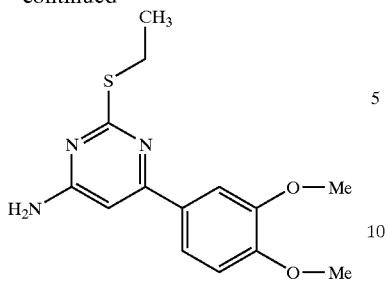

To a solution of iodoethane (75.6 g, 485 mmol) and 4-amino-6-(3,4-dimethoxyphenyl)-2-mercapto-pyrimidine (63.8 g, 242 mmol) in DMSO (560 ml) was added a saturated aqueous NaHCO₃ solution (270 ml). The reaction mixture was stirred at room temperature overnight. The mixture was diluted with water (400 ml) and the precipitate was filtered to give the desired product. (51.3 g, 73%)

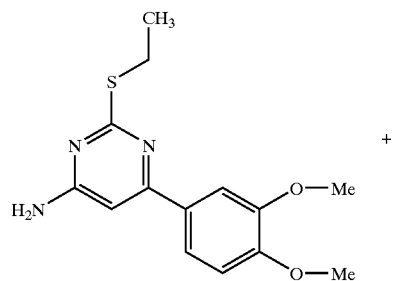 +

-continued

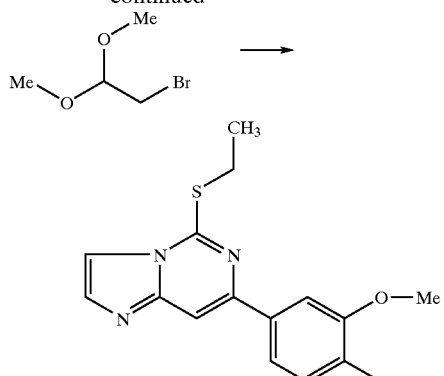

A solution of 4-amino-6-(3,4-dimethoxyphenyl)-2-(ethylthio)pyrimidine (25.7 g, 880 mmol) and bromoacetaldehyde dimethyl acetal (29.8 g, 1760 mmol) in water (500 ml) and THF (35 ml) was heated under reflux overnight. The mixture was cooled to room temperature. The precipitate was filtered and washed with water and MeOH. The product was isolated as the HBr salt and was used for the next reaction without neutralization. (25.0 g, 78%, Molecular weight: 315.3968)

With the use of other commercially available benzonitriles as substitutes for the 3,4-dimethoxybenzonitrile, and according to the procedure that is similar to that described above, following compounds shown in Table 1 below were prepared. IC$_{50}$ classes defined above are listed in the tables.

TABLE 1

| Ex. No. | MOLSTRUCTURE | MOLWEIGHT | Activity grade | MS | NMR |
|---|---|---|---|---|---|
| 1-1 | | 373.4338 | B | 374 | (DMSO d-6) 1.52 (3H, t, J = 7.1 Hz), 3.53 (2H, q, J = 7.1 Hz), 3.82 (3H, s), 3.86 (3H, s), 3.88 (3H, s), 7.10 (1H, d, J = 8.7 Hz), 7.78–7.83 (2H, m), 8.00 (1H, s), 8.27 (1H, s) |
| 1-2 | | 286.3579 | C | 287 | (DMSO d-6) 1.49 (3H, t, J = 7.2 Hz), 3.52 (2H, q, J = 7.2 Hz), 3.93 (3H, s), 6.95 (1H, d, J = 8.7 Hz), 7.71 (1H, d, J = 1.1 Hz), 7.83 (1H, s), 8.01 (1H, s), 8.47 (1H, dd), 9.03 (1H, d, J = 2.3 Hz) |

TABLE 1-continued

| Ex. No. | MOLSTRUCTURE | MOLWEIGHT | Activity grade | MS | NMR |
|---|---|---|---|---|---|
| 1-3 | | 299.3538 | B | | (CDCl$_3$) d 1.57 (3H, 1, J = 7.3 Hz), 3.51 (2H, q, J = 7.3 Hz), 6.04 (2H, s), 6.91 (1 H, d, J = 8.1 Hz), 7.47 (1H, d, J = 0.6 Hz), 7.56–7.6 (4H, m). |
| 1-4 | | 301.3697 | ND | | |
| 1-5 | | 285.3703 | B | 286 | |
| 1-6 | | 335.4308 | C | | |
| 1-7 | | 387.4609 | | 388 | (DMSO-d6) 1.34 (3H, t, J = 7.1 Hz), 1.52 (3H, t, J = 7.2 Hz), 3.53 (2H, q, J = 7.2 Hz), 3.83 (3H, s), 3.88 (3H, s), 4.34 (2H, q, J = 7.1 Hz), 7.09 (1H, d, J = 8.4 Hz), 7.76–7.82 (2H, m), 7.99 (1H, s), 8.23 (1H, s) |

TABLE 1-continued

| Ex. No. | MOLSTRUCTURE | MOLWEIGHT | Activity grade | MS | NMR |
|---|---|---|---|---|---|
| 1-8 | | 329.4239 | A | 330 | (DMSO-d6) 1.50 (3H, t, J = 7.2 Hz), 2.36 (3H, s), 3.50 (2H, q, J = 7.2 Hz), 3.82 (3H, s), 3.87 (3H, s), 7.07 (1H, d, J = 9.0 Hz), 7.52 (1H, s), 7.52 (1H, s), 7.76–7.79 (2H, m), 7.84 (1H, s) |
| 1-9 | | 315.3968 | | 316 | (DMSO-d6) 1.47 (3H, t, J = 7.2 Hz), 3.47 (2H, q, J = 7.3 Hz), 3.85 (3H, s), 3.94 (3H, s), 6.69–6.73 (2H, m), 7.67 (1H, d, J = 1.4 Hz), 7.77 (1H, s), 7.92 (1H, s), 8.13 (1H, dd) |
| 1-10 | | 339.3416 | | 340 | (DMSO-d6) 1.50 (3H, t, J = 7.3 Hz), 3.53 (2H, q, J = 7.3 Hz), 7.50 (1H, d, J = 8.1 Hz), 7.75 (1H, s), 7.86 (1H, s), 8.08 (1H, s), 8.31—8.36 (2H, m) |
| 1-11 | | 269.3709 | | | (DMSO-d6) 1.50 (3H, t, J = 7.3 Hz), 2.37 (3H, s), 3.52 (2H, q, J = 7.3 Hz), 7.32 (2H, d, J = 8.1 Hz), 7.70 (1H, s), 7.81 (1H, s), 7.95 (1H, s), 8.10 (2H, d, J = 8.2 Hz) |

TABLE 1-continued
| Ex. No. | MOLSTRUCTURE | MOLWEIGHT | Activity grade | MS | NMR |
|---|---|---|---|---|---|
| 1-12 | 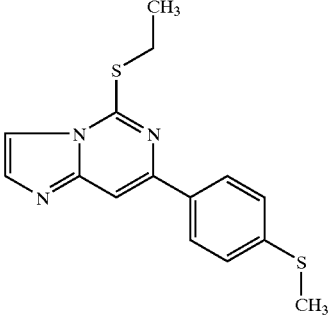 | 301.4349 | B | 302 | (DMSO-d6) 1.50 (3H, t, J = 7.3 Hz), 2.54 (3H, s), 3.52 (2H, q, J = 7.2 Hz), 7.38 (2H, d, J = 8.6 Hz), 7.71 (1H, d), 7.81 (1H, s), 7.98 (1H, s), 8.13–8.17 (2h, m) |
| 1-13 | 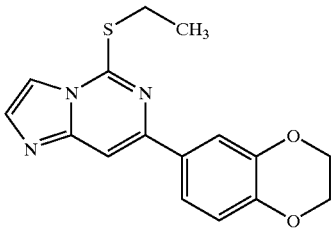 | 313.3795 | B | 314 | (CDCl3) d 1.56 (3H, t, J = 7.3 Hz), 3.51 (2H, q, J = 7.3 Hz), 4.32 (3H, s), 6.96 (1H, d, J = 8.5 Hz), 7.46 (1H, d, J = 0.6 Hz), 7.56 (1H, dd, J = 2.2, 8.6 Hz), 7.62 (3H, m). |
| 1-14 | 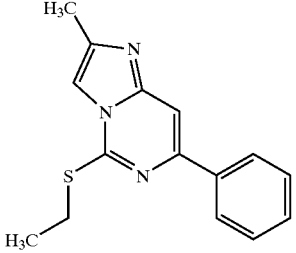 | 269.3709 | | | |
| 1-15 | 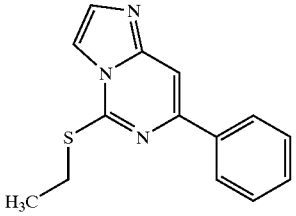 | 255.3438 | | | |

TABLE 1-continued

| Ex. No. | MOLSTRUCTURE | MOLWEIGHT | Activity grade | MS | NMR |
|---|---|---|---|---|---|
| 1-16 | | 271.278 | | | |

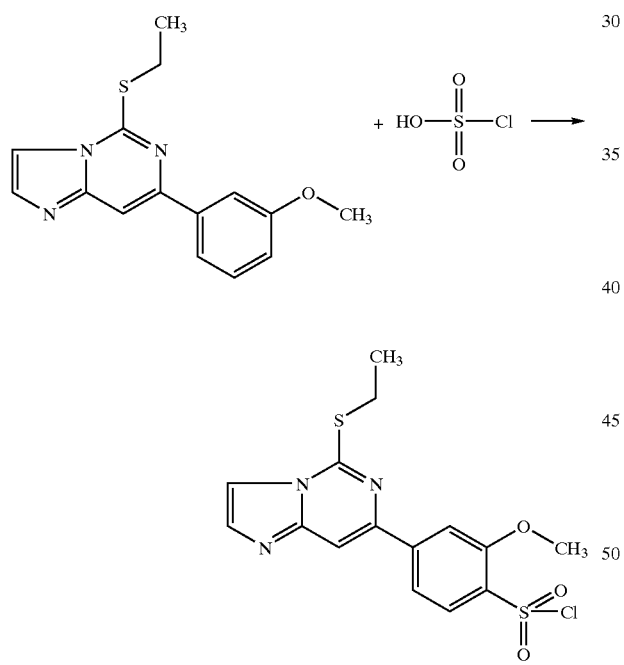

Example 2

With the use of 3-methoxybenzonitrile, and according to the similar procedure to that of Example 1, 5-Ethylsulfanyl-7-(3-methoxyphenyl)-imidazo[1,2-c]pyrimidine was prepared.

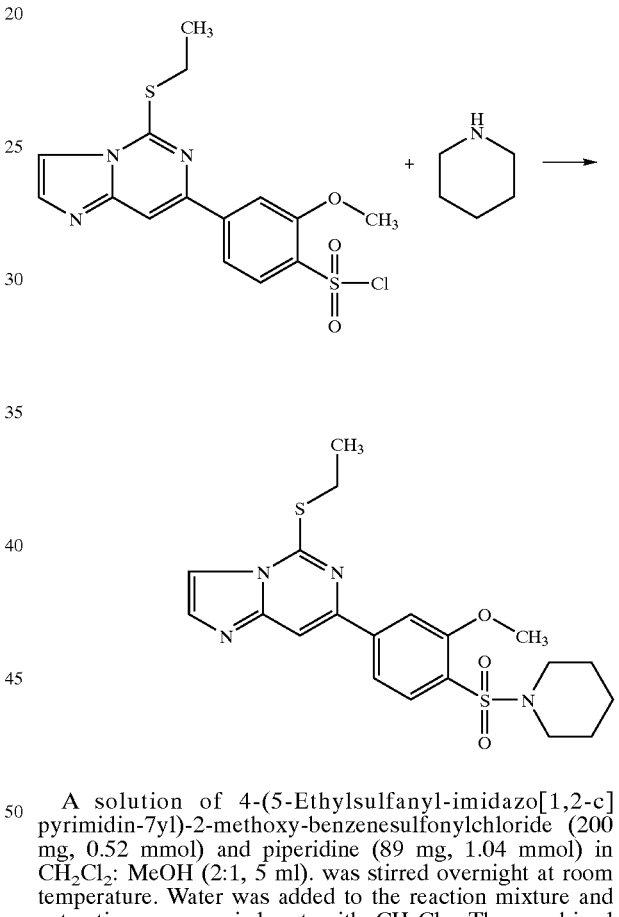

Then to 5 ml of chlorosulfonic acid was added 5-Ethylsulfanyl-7-(3-methoxyphenyl)-imidazo[1,2-c]pyrimidine (200 mg, 0.70 mmol). The mixture was stirred at room temperature overnight. The reaction mixture was added slowly to ice water. Extraction was carried out with $CH_2Cl_2$. The organic layer was washed with brine and dried over $MgSO_4$. The organic layer was then concentrated to give 4-(5-Ethylsulfanyl-imidazo[1,2-c]pyrimidin-7yl)-2-methoxy-benzenesulfonyl chloride(201 mg, 75%).

A solution of 4-(5-Ethylsulfanyl-imidazo[1,2-c]pyrimidin-7yl)-2-methoxy-benzenesulfonylchloride (200 mg, 0.52 mmol) and piperidine (89 mg, 1.04 mmol) in $CH_2Cl_2$: MeOH (2:1, 5 ml). was stirred overnight at room temperature. Water was added to the reaction mixture and extraction was carried out with $CH_2Cl_2$. The combined organic layer was washed with brine and dried over $Na_2SO_4$. The organic layer was concentrated to give the crude product of 5-Ethylsulfanyl-7-[3-methoxy-4-(piperidine-1-sulfonyl)-phenyl]imidazo[1,2-c]pyrimidine which was purified by preparative thin layer chromatography (45 mg, 20%).

Molecular weight: 432.5667 Activity grade: C-D
$^1$H-NMR (DMSO d-6) 1.21–1.40 (6H, m), 1.39 (3H, t, J=7.2 Hz), 2.80–2.83 (4H, m), 3.37 (2H, q, J=7.2 Hz), 3.88 (3H, s), 7.13 (1H, d, J=2.6 Hz), 7.21 (1H, dd), 7.50 (1H, s), 7.75 (1H, d, J=1.1 Hz), 7.88–7.91 (2H, m)

According to the procedure that is similar to that described above, following compounds shown in Table 2 below were prepared. $IC_{50}$ classes defined above are listed in the tables.

TABLE 2
| | | | | | |
|---|---|---|---|---|---|
| 2-1 | 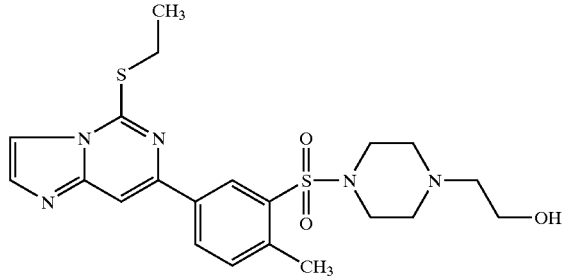 | 461.609 | B | 462 | (DMSO-d6) 1.51 (3H, t, J = 7.2 Hz), 2.38 (2H, 1, J = 6.1 Hz), 2.63 (3H, s), 3.08–3.11 (4H, m), 3.41–3.58 (4H, m), 7.59 (1H, d, J = 8.1 Hz), 7.75 (1H, s), 7.87 (1H, s), 8.12 (1H, s), 8.37 (1H, dd), 8.61 (1H, s) |
| 2-2 | 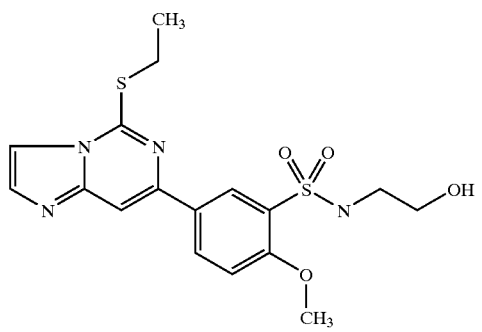 | 408.5013 | A | 409 | (DMSO-d6) 1.51 (3H, t, J = 7.2 Hz), 2.80–2.91 (2H, m), 3.38 (2H, q, J = 6.3 Hz), 3.52 (2H, q, J = 7.2 Hz), 3.98 (3H, s), 4.64 (1H, t, J = 5.6 Hz), 7.17 (1H, br), 7.36 (1H, d, J = 8.8 Hz), 7.72 (1H, d, J = 1.4 Hz), 7.84 (1H, s), 7.99 (1H, s), 8.42 (1H, dd) |
| 2-3 | 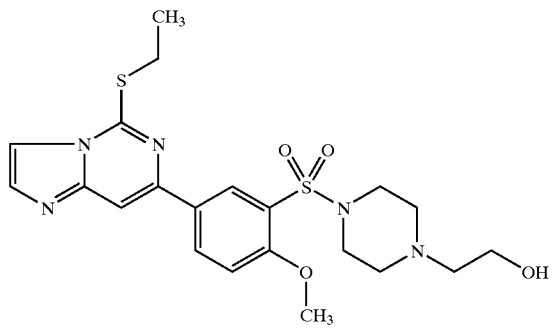 | 477.6084 | A | 478 | (DMSO-d6) 1.51 (3H, t, J = 7.2 Hz), 2.38 (2H, t, J = 6.2 Hz), 2.43–2.51 (4H, m), 3.11–3.16 (4H, m), 3.42–3.54 (4H, m), 3.97 (3H, s); 4.35(1H, t, J = 5.4 Hz), 7.39 (1H, d, J = 8.9 Hz), 7.72 (1H, d, J = 1.4 Hz), 7.84 (1H, s), 8.01 (1H, s), 8.42–8.47 (1H, dd), 8.61 (1H, d, J = 2.4 Hz) |
| 2-4 | 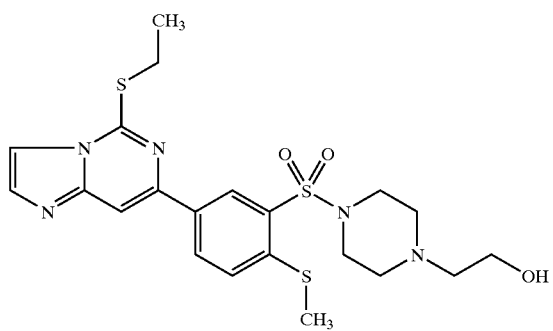 | 493.6731 | B | 494 | (DMSO-d6) 1.49 (3H, t, J = 7.2 Hz), 2.40 (2H, t, J = 6.0 Hz), 2.48–2.54 (4H, m), 3.25–3.30 (4H, m), 3.42–3.54 (4H, m), 4.34 (1H, t, J = 5.4 Hz), 7.76 (1H, d, J = 1.3 Hz), 7.88–7.91 (2H, m), 8.16 (1H, s), 8.48–8.52 (1H, dd), 8.69 (1H, d, J = 1.8 Hz) |

TABLE 2-continued

| 2-5 | (structure) | 392.502 | A | 393 | (DMSO-d6) 1.51 (3H, t, J = 7.2 Hz), 2.63 (3H, s), 2.92 (2H, q, J = 5.9 Hz), 3.40 (2H, q, J = 5.8 Hz), 3.54 (2H, q, J = 7.2 Hz), 4.69 (1H, t, J = 5.6 Hz), 7.53 (1H, d, J = 8.0 Hz), 7.74–7.79 (2H, m), 7.87 (1H, s), 8.07 (1H, s), 8.29–8.33 (1H, m), 8.67 (1H, s) |
|---|---|---|---|---|---|
| 2-6 | (structure) | 434.5388 | C–D | 435 | (DMSO d-6) 1.39 (3H, t, J = 7.2 Hz), 2.79–2.82 (4H, m), 3.26–3.41 (6H, m), 3.89 (3H, s), 7.15 (1H, d, J = 2.6 Hz), 7.23 (1H, dd), 7.52 (1H, s), 7.75 (1H, d, J = 1.1 Hz), 7.88–7.92 (2H, m) |
| 2-7 | (structure) | 364.4484 | C–D | 365 | (DMSO d-6) 1.38 (3H, t, J = 7.1 Hz), 3.39 (2H: q, J = 72 Hz), 3.87 (3H, s), (3H, m), 7.59 (1H, s), 7.75 (1H, d, J = 1.1 Hz), 7.87 (1H, s), 8.00 (1H, d, J = 8.7 Hz) |
| 2-8 | (structure) | 435.5705 | C–D | 436 | (DMSO d-6) 1.39 (3H, t, J = 7.4 Hz), 2.05 (6H), 2.26 (2H, t, J = 6.8 Hz), 2.80 (2H, t, J = 6.8 Hz), 3.88 (3H, s), 7.13–19 (3H, m), 7.56 (1H, s), 7.76 (1H, s), 7.94 (1H, d, J = 8.7 Hz) |

TABLE 2-continued

| | Structure | MS calc. | C-D | MS found | NMR |
|---|---|---|---|---|---|
| 2-9 | 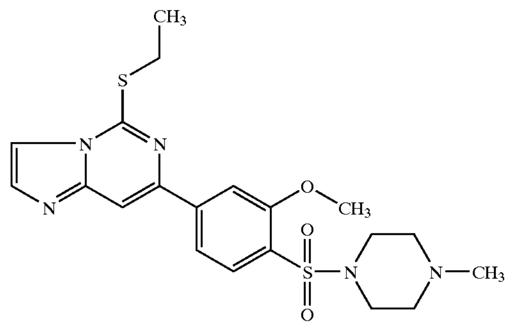 | 447.5815 | C–D | 448 | (DMSO d-6) 1.40 (3H, t, J = 7.2 Hz), 2.78–2.81 (4H, m), 3.89 (3H, s), 7.16 (1H, d, J = 2.6 Hz), 7.22 (1H, dd), 7.52 (1H, s), 7.76 (1H, d , J = 1.1 Hz), 7.88–7.94 (2H, m) |
| 2-10 | 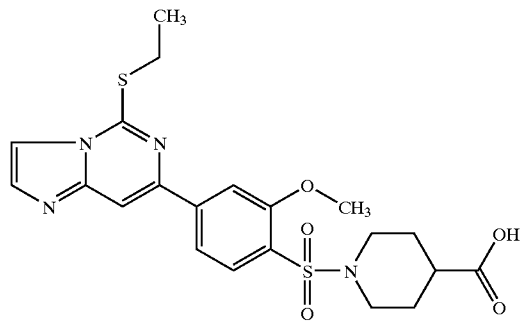 | 476.5756 | C–D | 477 | (DMSO d-6) 1.39 (3H, t, J = 7.2 Hz), 3.85 (3H, s), 7.14 (1H, d, J = 2.6 Hz), 7.21 (1H, dd), 7.49 (1H, s), 7.78 (1H, s), 7.88–7.94 (2H, m), 12.32 (1H, br) |
| 2-11 | 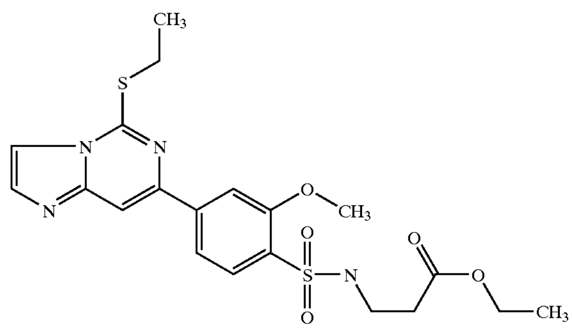 | 464.5646 | C–D | 465 | (DMSO d-6) 1.13 (3H, t, J = 7.2 Hz), 1.38 (3H, t, J =7.2 Hz), 2.36 (2H, t, J = 6.8 Hz), 2.75– 2.95 (2H, m), 3.38 (2H, q, J = 7.2 Hz), 3.89 (3H, s), 4.00 (2H, q, J = 7.1 Hz), 7.11 (1H, d, J = 2.6 Hz), 7.19 (1H, dd), 7.33 (1H, br), 7.52 (1H, s), 7.75 (1H, d, J = 1.5 Hz), 7.86–7.94 (2H, m) |

Example 3

To 4-hydroxy-3-methoxybenzonitrile (20.0 g, 134 mmol) in acetone (200 ml) were added K$_2$CO$_3$ (55.6 g, 402 mmol) and benzyl chloride (23.2 ml, 201 mmol). The resulting reaction mixture was refluxed overnight. After cooling to room temperature, acetone was removed by evaporation under reduced pressure and the residue was recrystallized to obtain 4-benzyloxy-3-methoxy-benzonitrile(28.5 g, 88%). Then, according to the similar procedure of Example 1, 7-(4-Benzyloxy-3-methoxy-phenyl)-5-ethylsulfanyl-imidazo[1,2-c]pyrimidine was prepared.

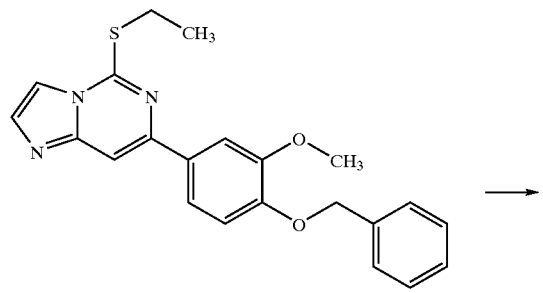

→

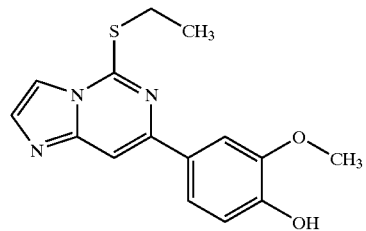

Next, to 7-(4-Benzyloxy-3-methoxy-phenyl)-5-ethylsulfanyl-imidazo[1,2-c]pyrimidine (5.0 g, 12.77 mmol) were added TFA (5 ml) and thioanisole (2 ml). The resulting reaction mixture was stirred at room temperature overnight. Ice water was added and the resulting precipitate was collected by filtration. The crude product of 4-(5-Ethylsulfanyl-imidazo[1,2-c]pyrimidin-7-yl)-2-methoxyphenol was suspended in CH$_2$Cl$_2$ and used in the next reaction without further purification. (3.4 g, 88%)

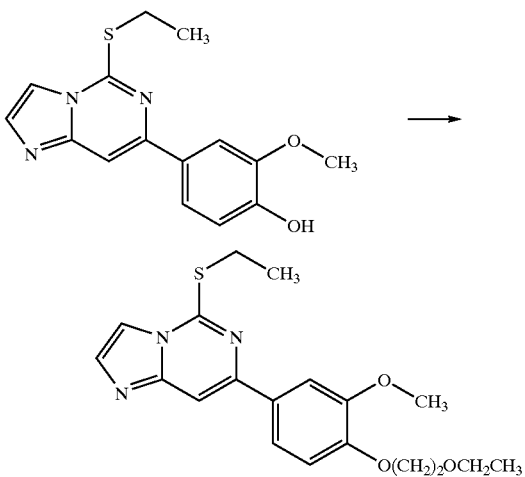

To 4-(5-Ethylsulfanyl-imidazo[1,2-c]pyrimidin-7-yl)-2-methoxy-phenol (45 mg, 0.15 mmol) in DMF (1 ml) were added bromoethyl ethyl ether (34?l, 0.30 mmol) and $K_2CO_3$ (62 mg, 0.45 mmol). The reaction mixture was stirred at 50° C. overnight. After cooling to room temperature, the mixture was poured into water and extracted with EtOAc. The combined organic extract was dried over $MgSO_4$, concentrated in vacuo and purified by preparative thin layer chromatography to give the desired product. (24.6 mg, 43.5%)

Molecular weight: 373.4774 Mass spectrometry: 374 Activity grade: A $^1$H-NMR: (CDCl3) d 1.25 (3H, t, J=7.0 Hz), 1.59 (3H, t, J=7.3 Hz), 3.51 (2H, q, J=7.3 Hz), 3.62 (2H, q, J=7.0 Hz), 3.86 (2H, t, J=5.2 Hz), 3.96 (3H, s), 4.25 (2H, t, J=5.2 Hz), 7.02 (1H, d, J=8.4 Hz), 7.47 (1H, t, J=0.6 Hz), 7.65 (4H, m).

According to the procedure that is similar to that of Example 3, following compounds shown in Table 3 below were prepared. $IC_{50}$ classes defined above are listed in the tables.

TABLE 3

| Ex. No. | MOLSTRUCTURE | MOLWEIGH | Activity grade | MS | NMR |
|---|---|---|---|---|---|
| 3-1 | | 329.42 | A | | |
| 3-2 | | 341.4351 | A | | |
| 3-3 | | 421.5221 | B | 422 | (CDCl3) d 1.59 (3H, t, J = 7.3 Hz), 3.50 (2H, q, J = 7.3 Hz), 3.81 (3H, s), 3.98 (3H, s), 5.15 (2H, s), 6.87–6.93 (2H, m), 6.99 (1H, d, J = 8.5 Hz), 7.29 (1H, d, J = 8.6 Hz), 7.39 (1H, d, J = 8.6 Hz), 7.47 (s, 1H), 7.57–7.69 (m, 4H). |

TABLE 3-continued

| Ex. No. | MOLSTRUCTURE | MOLWEIGH | Activity grade | MS | NMR |
|---|---|---|---|---|---|
| material for Example 3 | | 301.3697 | A | 302 | (CDCl3) d 1.59 (3H, t, J = 7.3 Hz), 3.51 (2H, q, J = 7.3 Hz), 3.99 (3H, s), 5.81 (1H, s), 7.02 (1H, d, J = 8.9 Hz), 7.47 (1H, s), 7.62 (4H, m). |
| 3-4 | | 399.5157 | A | 400 | (CDCl3) d 1.37–1.70 (4H, m), 1.59 (3H, t, J = 7.3 Hz), 1.73–1.82 (1H, m), 1.87–1.97 (1H, m), 3.48–3.57 (3H, m), 3.81 (1H, m), 3.95 (3H, s), 3.96–4.15 (3H, m), 7.00 (1H, d, J = 8.4 Hz), 7.47 (1H, t, J = 0.6 Hz), 7.64 (4H, m). |
| 3-5 | | 343.451 | A | 344 | (CDCl3) d 1.43 (6H, d, J 6.0 Hz), 1.59 (3H, t, J = 7.3 Hz), 3.51 (2H, q, J = 7.3 Hz), 3.81 (1H, m), 3.95 (3H, s), 7.01 (1 H, d, J = 8.2 Hz), 7.47 (1H, t, J = 0.6 Hz), 7.62 (4H, m). |
| 3-6 | | 383.5163 | B | 384 | (CDCl3) d 1.35 (4H, m), 1.62 (7H, m), 1.85 (2H, m), 2.07 (2H, m), 3.50 (2H, q, J = 7.3 Hz), 3.95 (3H, s), 5.15 (2H, s), 4.29 (1H, m), 7.00 (1H, d, J 8.4 Hz), 7.47 (1H, s), 7.64 (4H, m). |

TABLE 3-continued

| Ex. No. | MOLSTRUCTURE | MOLWEIGH | Activity grade | MS | NMR |
|---|---|---|---|---|---|
| 3-7 | | 343.4073 | A | 344 | (CDCl3) d 1.58 (3H, t, J = 7.3 Hz), 2.35 (3H, s), 3.51 (2H, q, J = 7.3 Hz), 3.94 (3H, s), 7.14 (1H, d, J = 8.4 Hz), 7.50 (1H, t, J = 0.7 Hz), 7.69 (4H, m). |
| 3-8 | | 371.4615 | B | 372 | (CDCl3) d 1.35 (6H, d, J = 7.0 Hz), 1.59 (3H, t, J = 7.3 Hz), 2.89 (1H, quint, J = 7.0 Hz), 3.50 (2H, q, J = 7.3 Hz), 3.92 (3H, s), 7.12 (1H, d, J = 8.3 Hz), 7.50 (1H, t, J = 0.7 Hz), 7.62–7.74 (4H, m). |
| 3-9 | | 372.4491 | B | 373 | (CDCl3) d 1.24 (3H, t, J = 7.1 Hz), 1.58 (3H, t, J = 7.3 Hz), 3.35 (2H, quint, J = 6.6 Hz), 3.50 (2H, q, J = 7.3 Hz), 3.95 (3H, s), 5.06 (1H, broad t), 7.14 (1H, d, J = 8.4 Hz), 7.50 (1H, d, J = 0.7 Hz), 7.69 (4H, m). |
| 3-10 | | 379.4596 | B | 380 | (CDCl3) d 1.59 (3H, t, J = 7.3 Hz), 3.24 (3H, s), 3.51 (2H, q, J = 7.3 Hz), 4.00 (3H, s), 7.41 (1H, d, J = 8.4 Hz), 7.52 (1H, d, J = 0.6 Hz), 7.51–7.71 (4H, m). |

TABLE 3-continued

| Ex. No. | MOLSTRUCTURE | MOLWEIGH | Activity grade | MS | NMR |
|---|---|---|---|---|---|
| 3-11 | | 359.4067 | A | 360 | (CDCl3) d 1.59 (3H, t, J = 7.3 Hz), 3.51 (2H, q, J = 7.3 Hz), 3.93 (3H, s), 3.96 (3H, s), 7.24(1 H, d, J = 8.4 Hz), 7.51 (1H, d, J = 0.7 Hz), 7.63 (1H, d, J = 1.9 Hz), 7.66 (2H, m), 7.75 (1H, d, J = 1.9 Hz). |
| 3-12 | | 372.4491 | C | 373 | (CDCl3) d 1.57 (3H, t, J = 7.3 Hz), 3.02 (3H, s), 3.14 (3H, s), 3.52 (2H, q, J = 7.3 Hz), 3.96 (3H, s), 6.96 (1H, d, J = 8.4 Hz), 7.47 (1H, t, J = 0.6 Hz), 7.60–7.70 (4H, m). |

Example 4

As a starting material, 3-hydroxy-4-methoxy benzonitrile was prepared.

First, a mixture of 3-hydroxy-4-methoxy benzaldehyde (25 g, 164.3 mmol), hydroxylamine hydrochloride (13.7 g, 197.2 mmol), and acetic acid sodium salt (27 g, 328.6 mmol) in acetic acid (200 ml) was refluxed overnight. After cooling, the acetic acid was evaporated under reduced pressure. Water was added to the residue and the resulting precipitate was collected by filtration. The crude product was recrystalized to give 3-hydroxy-4-methoxy benzonitrile. (23.54 g, 96%)

Then with the use of this nitrile compound and according to the procedure that is similar to that of Example 3, following compounds shown in Table 4 below were prepared.

TABLE 4

| Ex. No. | MOLSTRUCTURE | MOLWEIGH | Activity grade | MS | NMR |
|---|---|---|---|---|---|
| 4-1 | | 391.4956 | B | 392 | (CDCl3) d 1.52 (3H, t, J = 7.3 Hz), 3.40 (2H, q, J = 7.3 Hz), 3.96 (3H, s), 5.27 (2H, s), 7.00 (1H, d, J = 8.2 Hz), 7.31 (1H, d, J = 7.6 Hz), 7.38 (2H, t, J = 7.4 Hz), 7.47 (3H, m), 7.56 (1H, s), 7.63 (1H, dd, J = 2.2, 12.6 Hz), 7.67 (1H, d, J = 2.0 Hz). |
| 4-2 | | 301.3697 | A | 302 | (CDCl3) d 1.57 (3H, t, J = 7.3 Hz), 3.52 (2H, q, J = 7.3 Hz), 3.96 (3H, s), 5.81 (1H, s), 6.96 (1H, d, J = 8.5 Hz), 7.47 (1H, t, J = 0.6 Hz), 7.58–7.64 (3H, m), 7.69 (1H, d, J = 2.1 Hz). |

TABLE 4-continued

| Ex. No. | MOLSTRUCTURE | MOLWEIGH | Activity grade | MS | NMR |
|---|---|---|---|---|---|
| 4-3 | | 343.451 | A | 344 | (CDCl3) d 1.43 (6H, d, J = 6.0 Hz), 1.59 (3H, t, J = 7.3 Hz), 3.51 (2H, q, J = 7.3 Hz), 3.92 (3H, s), 4.63 (1H, quint, J = 6.0 Hz), 6.98 (1H, d, J = 8.4 Hz), 7.47 (1H, s), 7.63–7.71 (4H, m). |
| 4-4 | | 383.5163 | B | 384 | (CDCl3) d 1.34 (4H, m), 1.57 (5H, m), 1.87 (2H, m), 2.11 (2H, m), 3.51 (2H, q, J = 7.3 Hz), 3.92 (3H, s), 4.30 (1H, m), 6.98 (1H, d, J = 8.4 Hz), 7.47 (1H, s), 7.63 (3H, m), 7.72 (1H, d, J = 2.1 Hz). |
| 4-5 | | 399.5157 | B | 400 | (CDCl3) d 1.40–1.71 (5H, m), 1.78 (1H, m), 1.93 (1 H, m), 3.52 (3H, m), 3.83 (1H, m), 3.92 (3H, s), 3.99–4.18 (3H, m), 6.96 (1H, d, J = 8.4 Hz), 7.47 (1H, t, J = 0.6 Hz), 7.63 (2H, m), 7.66 (1H, dd, J = 2.1, 8.4 Hz), 7.72 (1H, d, J = 2.1 Hz). |
| 4-6 | | 373.4774 | A | 374 | (CDCl3) d 1.25 (3H, t, J = 7.0 Hz), 1.58 (3H, t, J = 7.3 Hz), 3.51 (2H, q, J = 7.3 Hz), 3.63 (2H, q, J = 7.0 Hz), 3.87 (2H, t, J = 5.2 Hz), 3.93 (3H, s), 4.29 (2H, t, J = 5.2 Hz), 6.98 (d, 1H, J = 8.4 Hz), 7.47 (1H, s), 7.63 (2H, s), 7.67 (1H, dd, J = 2.0, 8.4 Hz), 7.73 (1 H, d, J = 2.0 Hz). |
| 4-7 | | 343.4073 | A | 344 | (CDCl3) d 1.56 (3H, t, J = 7.3 Hz), 2.37 (3H, s), 3.51 (2H, q, J = 7.3 Hz), 3.90 (3H, s), 7.04 (1H, d, J = 8.6 Hz), 7.48 (1H, t, J = 0.6 Hz), 7.62 (2H, m), 7.77 (1H, d, J = 2.2 Hz), 7.93 (1H, dd, J = 2.2, 8.6 Hz). |
| 4-8 | | 372.4491 | A | 373 | (CDCl3) d 1.25 (3H, t, J = 7.1 Hz), 1.56 (3H, t, J = 7.3 Hz), 3.35 (2H, quint, J = 6.6 Hz), 3.51 (2H, q, J = 7.3 Hz), 3.92 (3H, s), 5.07 (1H, broad t), 7.05 (1H, d, J = 8.6 Hz), 7.47 (1H, s), 7.63 (2H, m), 7.82 (1H, d, J = 2.2 Hz), 7.92 (1H, dd, J = 2.2, 8,6 Hz). |

TABLE 4-continued

| Ex. No. | MOLSTRUCTURE | MOLWEIGH | Activity grade | MS | NMR |
|---|---|---|---|---|---|
| 4-9 | | 379.4596 | B | 380 | (CDCl3) d 1.57 (3H, t, J = 7.3 Hz), 3.22 (3H, s), 3.52 (2H, q, J = 7.3 Hz), 3.97 (3H, s), 7.09 (1H, d, J = 8.6 Hz), 7.51 (1H, s), 7.80 (1H, s), 7.98 (1H, d, J =8.2 Hz), 8.14 (1H, s), 8.29 (1H, s). |
| 4-10 | | 372.4491 | B | 373 | (CDCl3) d 1.57 (3H, t, J = 7.3 Hz), 3.04 (3H, s), 3.17 (3H, s), 3.52 (2H, q, J = 7.3 Hz), 3.91 (3H, s), 7.05 (1H, d, J = 8.6 Hz), 7.47 (1H, s), 7.64 (2H, broad d), 7.79 (1H, d, J = 2.2 Hz), 7.93 (1h, dd, J = 2.2, 8.6 Hz). |

Example 5

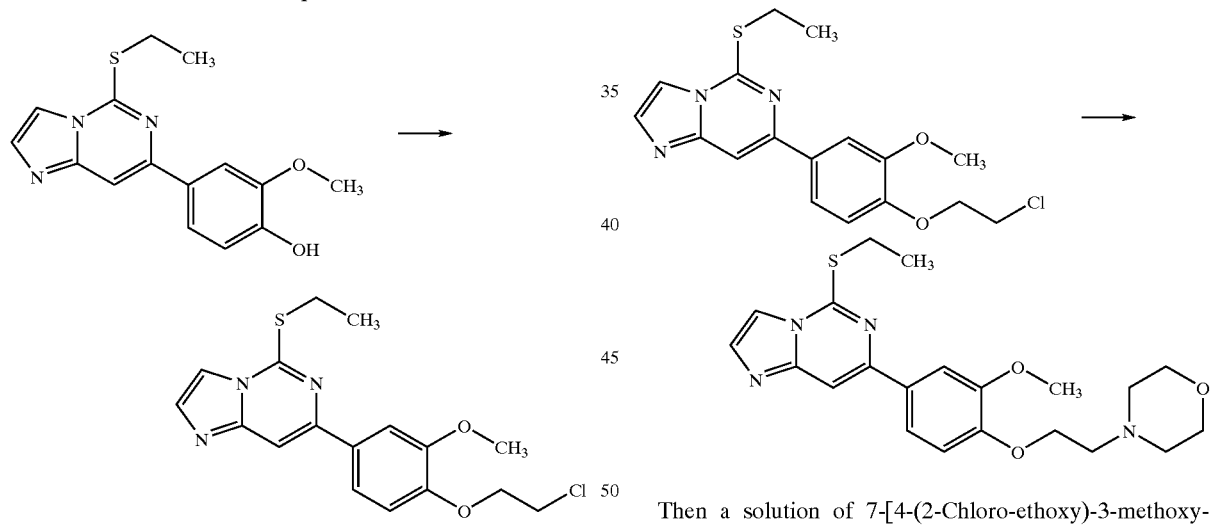

A mixture of 4-(5-Ethylsulfanyl-imidazo[1,2-c]pyrimidin-7-yl)-2-methoxyphenol (750 mg, 2.49 mmol) obtained in the process of Example 3, 1-bromo-2-chloroethane (0.62 ml, 7.47 mmol) and CS$_2$CO$_3$ (2.43 g, 7.47 mmol) in acetone (25 ml) was refluxed for 3 h. After cooling to room temperature, the mixture was poured into water and extracted with EtOAc. The organic extract was dried over MgSO$_4$, concentrated in vacuo and the residue was purified by column chromatography to give 7-[4-(2-Chloro-ethoxy)-3-methoxy-phenyl]-5-ethylsulfanyl-imidazo[1,2-c]pyrimidine (805 mg, 88%).

Then a solution of 7-[4-(2-Chloro-ethoxy)-3-methoxy-phenyl]-5-ethylsulfanyl-imidazo[1,2-c]pyrimidine (800 mg, 2.2 mmol) in morpholine (10 ml) was stirred at 100° C. overnight. After cooling to room temperature, the mixture was poured into a dilute NaOH solution and extracted with CH$_2$Cl$_2$. The combined organic extract was dried over MgSO$_4$ and concentrated in vacuo. The crude product was purified by column chromatography to give 5-Ethylsulfanyl-7-[3-methoxy-4-(2-morpholin-4-yl-ethoxy)-phenyl]-imidazo[1,2-c]pyrimidine (650 mg, 71%).

Molecular weight: 414.5274 Mass spectrometry: 415 Activity grade: A $^1$H-NMR: (CDCl3) d 1.59 (3H, t, J=7.3 Hz), 2.61 (4H, t, J=4.6 Hz), 2.88 (2H, t, J=6.0 Hz), 3.51 (2H, q, J=7.3 Hz), 3.75 (4H, t, J=4.6 Hz), 3.96 (3H, s), 4.23 (2H, t, J=6.0 Hz), 6.99 (1H, d, J=8.4 Hz), 7.48 (1H, s), 7.61–7.68 (4H, m).

According to the procedure that is similar to that described above, following compounds shown in Table 5 below were prepared.

TABLE 5

| Ex. No. | MOLSTRUCTURE | MOL-WEIGH | Activity grade | MS | NMR |
|---|---|---|---|---|---|
| 5-1 | | 428.5542 | A | 429 | (CDCl3) d 1.59 (3H, t, J = 7.3 Hz), 2.05 (2H, quint, J = 6.8 Hz), 2.48 (4H, t, J = 4.5 Hz), 2.56 (2H, t, J = 7.1 Hz), 3.51 (2H, q, J = 7.3 Hz), 3.72 (4H, t, J = 4.6 Hz), 3.96 (3H, s), 4.17 (2H, t, J = 6.6 Hz), 7.00 (1H, d, J = 8.4 Hz), 7.48 (1H, s), 7.61 |
| 5-2 | | 414.571 | A | | (CDCl3) d 1.04 (6H, t, J = 7.1 Hz), 1.59 (3H, t, J = 7.3 Hz), 2.01 (2H, quint, J = 6.9 Hz), 2.49–2.67 (6H, m), 3.51 (2H, q, J = 7.3 Hz), 3.96 (3H, s), 4.15 (2H, t, J = 6.6 Hz), 7.01 (1H, d, J = 8.3 Hz), 7.47 (1H, s), 7.60–7.68 (4H, m). |
| 5-3 | | 416.5432 | A | | (CDCl3) d 1.59 (3H, t, J = 7.3 Hz), 2.07 (2H, quint, J = 6.6 Hz), 2.32 (3H, s), 2.60 (2H, t, J = 5.3 Hz), 2.68 (2H, t, J = 7.1 Hz), 3.51 (2H, q, J = 7.3 Hz), 3.63 (2H, t, J = 5.3 Hz), 3.96 (3H, s), 4.15 (2H, t, J = 6.4 Hz), 6.98 (1 H, d, J = 8.3 Hz), 7.47 (1H, s), 7.61–7.68 (4H, m). |
| 5-4 | | 441.5969 | B | | (CDCl3) d 1.59 (3H, t, J = 7.3 Hz), 2.08 (2H, quint, J = 6.8 Hz), 2.35 (3H, s), 2.40–2.60 (10, m), 3.51 (2H, q, J = 7.3 Hz), 3.93 (3H, s), 4.18 (2H, t, J = 6.8 Hz), 6.97 (1H, d, J = 8.6 Hz), 7.47 (1H, s), 7.62–7.68 (4H, m). |
| 5-5 | | 455.6237 | B | | (CDCl3) d 1.56 (3H, t, J = 7.3 Hz), 1.73 (1H, m), 3.51 (2H, q, J = 7.3 Hz), 3.91 (3H, s), 4.19 (2H, t, J = 9.0 Hz), 6.97 (1H, d, J = 8.6 Hz), 7.47 (1H, s), 7.62–7.68 (4H, m). |

TABLE 5-continued

| Ex. No. | MOLSTRUCTURE | MOL-WEIGH | Activity grade | MS | NMR |
|---|---|---|---|---|---|
| 5-6 | | 426.582 | B | | (CDCl3) d 1.43–1.62 (9H, m), 2.08 (2H, quint, J = 6.8 Hz), 2.42 (4H, broad s), 2.53 (2H, broad t), 3.51 (2H, q, J = 7.3 Hz), 3.94 (3H, s), 4.18 (2H, t, J = 6.8 Hz), 6.97 (1H, d, J = 8.3 Hz), 7.47 (1H, s), 7.60–7.69 (4H, m). |
| 5-7 | | 426.582 | A | | (CDCl3) d 1.46–1.62 (9H, m), 2.10 (2H, broad quint), 2.46–2.56 (6H, broad m), 3.51 (2H, q, J 7.3 Hz), 3.95 (3H, s), 4.16 (2H, t, J = 6.8 Hz), 7.01 (1H, d, J = 8.3 Hz), 7.47 (1H, d, J = 0.7 Hz), 7.60–7.67 (4H, m). |
| 5-8 | | 441.5969 | A | | (CDCl3) d 1.58 (3H, t, J = 7.3 Hz), 2.05 (2H, quint, J = 6.8 Hz), 2.31 (3H, s), 2.48–2.63 (10H, m), 3.51 (2H, q, J = 7.3 Hz), 3.94 (3H, s), 4.16 (2H, t, J = 6.8 Hz), 7.00 (1H, d, J = 8.3 Hz), 7.47 (1H, s), 7.60–7.68 (4H, m). |
| 5-9 | | 444.6212 | A | | (CDCl3) d 1.58 (3H, t, J = 7.3 Hz), 2.03 (2H, quint, J = 6.8 Hz), 2.58 (2H, t, J = 7.1 Hz), 2.66–2.77 (8H, m), 3.51 (2H, q, J = 7.3 Hz), 3.95 (3H, s), 4.14 (2H, t, J = 6.8 Hz), 7.00 (1H, d, J = 8.3 Hz), 7.48 (1H, a), 7.60–7.67 (4H, m). |
| 5-10 | | 444.6212 | B | | (CDCl3) d 1.59 (3H, t, J = 7.3 Hz), 2.06 (2H, quint, J = 6.8 Hz), 2.60 (2H, t, J = 7.1 Hz), 2.65–2.77 (8H, m), 3.51 (2H, q, J = 7.3 Hz), 3.93 (3H, s), 4.17 (2H, t, J = 6.8 Hz), 6.98 (1H, d, J = 8.9 Hz), 7.48 (1H, s), 7.60–7.65 (4H, m). |

TABLE 5-continued

| Ex. No. | MOLSTRUCTURE | MOL-WEIGH | Activity grade | MS | NMR |
|---|---|---|---|---|---|
| 5-11 | | 428.5542 | B | | (CDCl3) d 1.59 (3H, t, J = 7.3 Hz), 2.08 (2H, quint, J = 6.8 Hz), 2.49 (4H, broad s), 2.58 (2H, t, J = 7.1 Hz), 3.51 (2H, q, J = 7.3 Hz), 3.72 (4H, t, J = 4.4 Hz), 3.92 (3H, s), 4.20 (2H, t, J = 6.8 Hz), 6.98 (1H, d, J = 8.9 Hz), 7.47 (1H, s), 7.63–7.67 (4H, m). |
| 5-12 | | 414.5274 | B | | (CDCl3) d 1.58 (3H, t, J = 7.3 Hz), 2.63 (4H, broad s), 2.90 (2H, t, J = 6.0 Hz), 3.51 (2H, q, J = 7.3 Hz), 3.75 (4H, t, J = 4.7 Hz), 3.93 (3H, s), 4.27 (2H, t, J = 6.0 Hz), 6.98 (1H, d, J = 8.2 Hz), 7.47 (1H, d, J = 0.6 Hz), 7.62–7.70 (4H, m). |
| 5-13 | | 469.6069 | A | | (CDCl3) d 1.59 (3H, t, J = 7.3 Hz), 1.61–2.22 (9H, m), 2.54 (2H, t, J = 7.1 Hz), 3.00 (2H, broad d), 3.51 (2H, q, J = 7.3 Hz), 3.94 (3H, s), 4.16 (2H, q, J = 6.8 Hz), 5.24(1H, broad s), 5.43 (1H, broad s), 6.99 (1H, d, J = 8.3 Hz), 7.47 (1H, d, J = 0.7 Hz), 7.60–7.65 (4H, m). |
| 5-14 | | 442.581 | A | | (CDCl3), 1.16 (3H, s), 1.18 (3H, s), 1.59 (2H, t, J = 7.5 Hz), 1.92 (2H, t, J = 10.6 Hz), 2.86 (2H, s), 2.88 (2H, s), 3.48(3H, d, J = 3.8 Hz), 3.72(2H, m), 3.96(3H,s), 4.23(2H, t, J = 6.0 Hz), 7.00 (1H, d, J = 8.3 Hz), 7.48 (1H, s), 7.64 (4H, m) |

Example 6

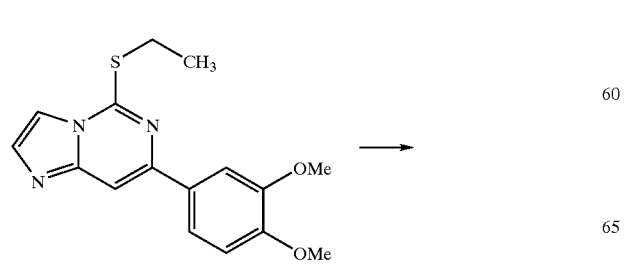

-continued

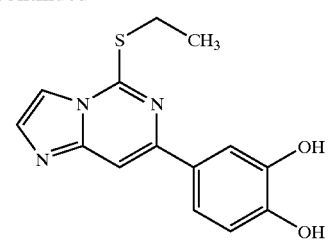

To 7-(3,4-Dimethoxy-phenyl)-5-ethylsulfanyl-imidazo[1,2-c]pyrimidine (1.1 g, 3.5 mmol) in CH$_2$Cl$_2$ (25 ml) at 0° C., was added dropwise 1M solution of BBr$_3$ in CH$_2$Cl$_2$ (25 ml, 25.0 mmol). The reaction mixture was stirred at 0° C. for 15 min and then at room temperature overnight. The mixture was then cooled using ice bath and ice-water was added, the precipitate was collected by filtration and then suspended in CH$_2$Cl$_2$ to give 4-(5-Ethylsulfanyl-imidazo[1,2-c]pyrimidin-7-yl)-benzene-1,2-diol. (875 mg, 87%)

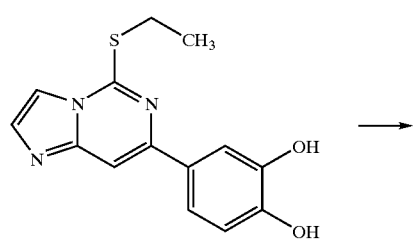

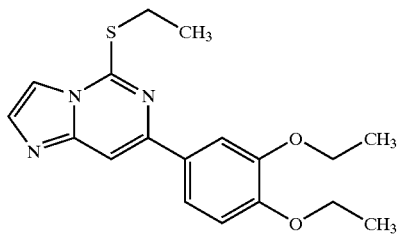

→

To 4-(5-Ethylsulfanyl-imidazo[1,2-c]pyrimidin-7-yl)-benzene-1,2-diol (86.2 mg, 0.3 mmol) in DMF (2 ml) were added ethyl bromide (112 μl, 1.5 mmol) and K$_2$CO$_3$ (290 mg, 2.1 mmol). The reaction mixture was stirred at about 50° C. overnight. After cooling to room temperature, it was poured into water and extracted with EtOAc. The combined organic extract was dried over MgSO$_4$ and concentrated in vacuo. The residue was purified by preparative thin layer chromatography to give 7-(3,4-Diethoxy-phenyl)-5-ethylsulfanyl-imidazo[1,2-c]pyrimidine (39.1 mg, yield 36%).

According to the procedure that is similar to that described above, following compounds shown in Table 6 below were prepared.

TABLE 6

| Ex. No. | MOLSTRUCTURE | MOLWEIGHT | Activity grade | MS | NMR |
|---|---|---|---|---|---|
| 6-1 | | 343.4489 | A | 344 | (CDCl3) d 1.46–1.61 (9H, m), 3.51 (2H, q, J = 7.3 Hz), 4.16 (2H, q, J = 7.0 Hz), 4.21 (2H, q, J = 7.0 Hz), 6.98 (1H, d, J = 8.5 Hz), 7.47 (1H, d, J = 0.6 Hz), 7.61–7.68 (4H, m). |
| 6-2 | | 431.5541 | B | 432 | (CDCl3) d 1.24 (3H, 1, J = 7.0 Hz), 1.25 (3H, t, J = 7.0 Hz), 1.58 (2H, q, J = 7.3 Hz), 3.51 (2H, q, J = 7.3 Hz), 3.63 (4H, m), 3.84 (4H, m), 4.24 (4H, m), 7.02 (1H, d, J = 8.5 Hz), 7.47 (1H, d, J = 0.6 Hz), 7.60–7.67 (3H, m), 7.72 (1H, d, J = 2.2 Hz). |
| material for Example 6 | | 287.3417 | C | | (DMSO d-6) d 1.52 (3H, t, J = 7.3 Hz), 3.58 (2H, q, J = 7.3 Hz), 6.92 (1H, d, J = 8.3 Hz), 7.62 (1H, dd, J = 2.2, 8.3 Hz), 7.70 (1H, d, J = 2.2 Hz), 7.87 (1H, s), 8.15 (2H, dd, J = 2.2, 10.7 Hz). |

Example 7

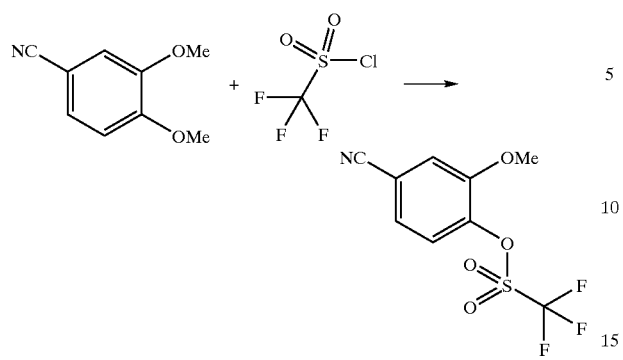

To a solution of 4-Hydroxy-3-methoxy-benzonitrile (89 g, 0.60 mol) in 1000 ml of CH$_2$Cl$_2$ was added 130 ml of triethylamine and triflic chloride (125 g, 0.79 mol) in the presence of a catalytic amount of Dimethylaminopyridine at 0° C. After being stirred for 1 h at 0° C., the reaction was quenched with water. The reaction mixture was washed with a saturated NaHCO$_3$ solution(30 ml) and brine (300 ml). The organic layer was dried over MgSO$_4$ and concentrated. The crude mixture was used for next step without further purification.

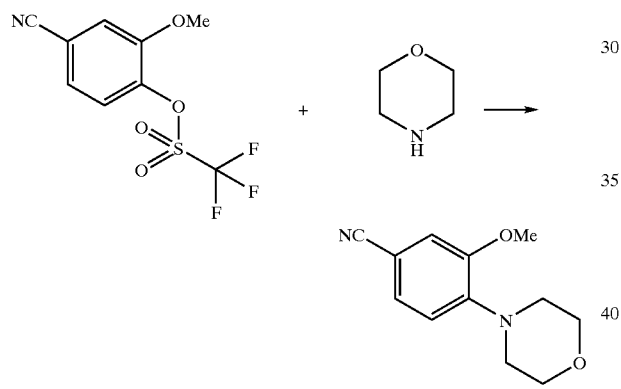

The crude triflate in 500 ml of morpholine was heated at 120° C. for 2 h. After cooling to room temperature, morpholine was removed under reduced pressure. The residue was diluted with 3N HCl (200 ml) and EtOAc (300 ml). After separation of the aqueous layer, the organic layer was extracted with 3N HCl. The combined aquous layer was basified by addition of 6N NaOH solution and then extracted with EtOAc. The combined organic layer was washed with brine (300 ml), dried over MgSO$_4$ and concentrated. The crude product was filtrated on silica. The filtrate was concentrated and the residue was recrytallized from ether to give 3-Methoxy-4-morpholin-4-yl-benzonitrile (39 g, 30%) as a white solid.

With the use of 3-Methoxy-4-morpholin-4-yl-benzonitrile, and according to the procedure that is similar to that of Example 1 above, 5-Ethylsulfanyl-7-(3-methoxy-4-morpholin-4-yl-phenyl)-imidazo[1,2-c]pyrimidine was prepared.
Molecular weight: 370.4768 Mass spectrometry: 371 Activity grade: A $^1$H-NMR: CDCl3 7.67–7.63 (m, 4H), 7.60 (s, 1H), 7.48 (s, 1H), 7.01 (d, 1H, J=15.1 Hz), 3.97 (s, 3H), 3.92 (t, 4H, J=7.6 Hz), 3.51 (q, 2H, J=12.2 Hz), 3.15 (t, 2H, J=7.6 Hz), 1.59 (t, 3H, J=12.3 Hz)

Example 8

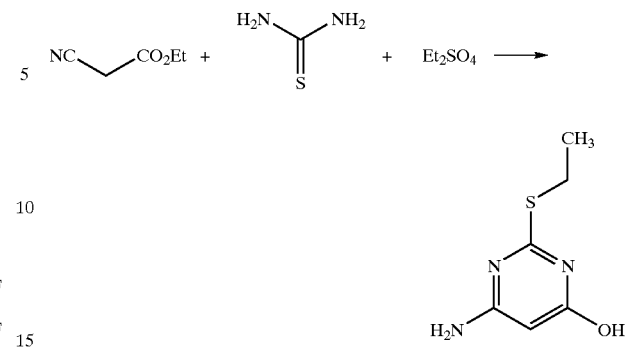

Sodium (3.92 g, 0.1 mol) was dissolved in 150 ml of ethanol. Ethyl cyanoacetate (17.5 g, 0.15 mol) and thiourea (12.8 g, 0.17 mol) were added and the mixture was refluxed for 2 h. After cooling to room temperature, 30 ml of water was added. Diethyl sulfate (23.9 g, 0.16 mol) was added at room temperature and the reaction mixture was refluxed for 15 min. After cooling to room temperature, the reaction mixture was concentrated in vacuo. The residue was recrystallized from water/MeOH to give the product (13 g, 50%) as a white solid.

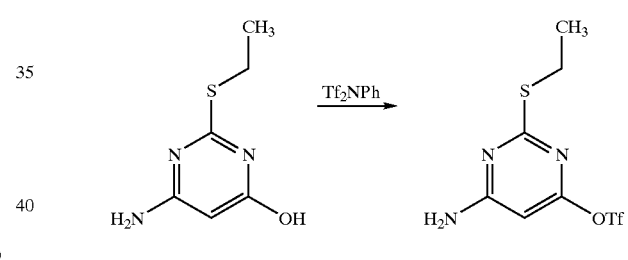

To a solution of 6-Amino-2-ethylsulfanyl-pyrimidin-4-ol (1.1 g, 6.42 mmol) in 3 ml of THF was added NaH (0.23 g, 9.64 mmol) at 0° C. After 15 min. at 0° C., N-phenyltrifluromethane sulfonamide (3.4 g, 9.64 mmol) was added. The reaction mixture was stirred at 0° C. for 1 h and warmed to room temperature. After 3 h, the reaction mixture was quenched with 0.5 ml of water and concentrated in vacuo. The residue was purified by column chromatography to give the product (1.7 g, 7%) as a white solid.

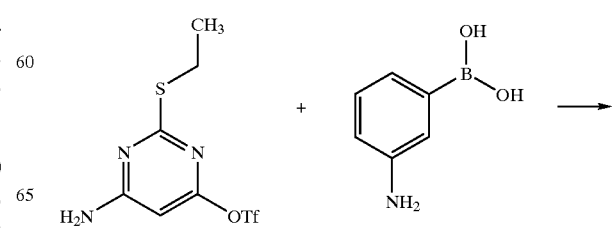

59
-continued

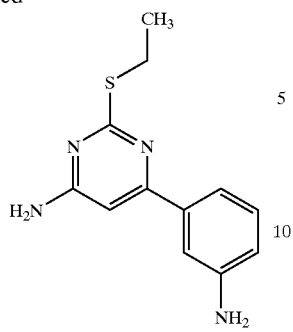

A mixture of triflate (100 mg, 0.33 mmol), aryl boronic acid (63 mg, 0.46 mmol), tri-o-tolylphosphine (24 mg, 0.08 mmol), Pd$_2$(dba)$_3$ (34 mg, 0.03 mmol) and cesium carbonate (183 mg, 0.56 mmol) in dioxane (5 ml) was degassed with vigorous stirring and filled with Ar atmosphere. The mixture was heated to 80° C. for 1 day. Cooled to room temperature, the mixture was diluted with 30 ml of CHCl$_3$ and filtered through a Celite pad. The filtrate was concentrated and the residue was purified by preparative thin layer chromatography to give the coupled product (40 mg, 49%).

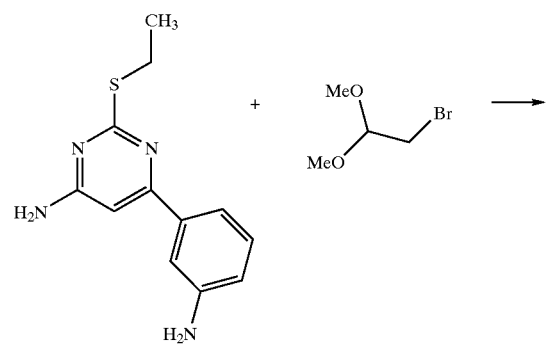

60
-continued

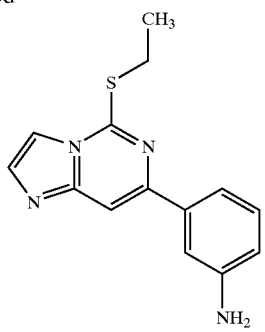

A mixture of aminopyrimidine (20 mg, 0.08 mmol) and dimethyl bromoacetal (27 mg, 0.16 mmol) in 1,4-dioxane/water (4 ml/1 ml) was refluxed for 1 day. The reaction mixture was concentrated, and the residue was diluted with 5 ml of MeOH. The mixture was treated with K$_2$CO$_3$ (2 mg) and diisopropylethylamine (0.5 ml). The mixture was filtered and the filtrate was concentrated. The residue was purified by preparative thin layer chromatography to give 3-(5-Ethylsulfanyl-imidazo[1,2-c]pyrimidin-7-yl)-phenylamine (7 mg, 32%).

Molecular weight: 270.3586 Mass spectrometry: 271 Activity grade: A $^1$H-NMR: CDCl3 7.60 (s, 1H), 7.58 (d, 1H, J=1.4 Hz), 7.42 (s, 1H), 7.39 (d, 1H, J=8.0 Hz), 7.33 (t, 1H, J=1.9 Hz), 7.19 (t, 1H, J=7.8 Hz), 6.97 (dd, 1H, J=7.8, 1.8 Hz), 3.72 (br s, 2H), 3.44 (q, 2H, J=7.3 Hz), 1.49 (t, 3H, J=7.3 Hz According to the procedure that is similar to that described above, following compounds shown in Table 8 below were prepared.

TABLE 8

| Ex. No. | MOLSTRUCTURE | MOLWEIGH | Activity grade | MS | NMR |
|---|---|---|---|---|---|
| 8-1 | | 285.3703 | B | 286 | CDCl3 7.72–7.66 (m, 4H), 7.50 (s, 1H), 7.40 (t, 1H, J = 7.9 Hz), 6.97 (dd, 1H, J = 8.3, 2.4 Hz), 3.90 (s, 3H), 3.52 (q, 2H, J = 7.3 Hz), 1.58 (t, 3H, J = 7.3 Hz) |
| 8-2 | | 256.3314 | C | 257 | CDCl3 9.35 (s, 1H), 8.65 (dd, 1H, J = 4.8, 1.4 Hz), 8.33 (dd, 1H, J = 7.9, 1.8 Hz), 7.77 (s, 1H), 7.70 (s, 1H), 7.54 (s, 1H), 7.43 (dd, 1H, J = 8.0, 4.9 Hz), 3.53 (q, 2H, J = 7.4 Hz), 1.58 (t, 3H, J = 7.3 Hz) |

TABLE 8-continued

| Ex. No. | MOLSTRUCTURE | MOLWEIGH | Activity grade | MS | NMR |
|---|---|---|---|---|---|
| 8-3 | | 261.3696 | B | 262 | CDCl3 7.63 (d, 1H, J = 1.3 Hz), 7.61 (d, 1H, J = 1.1 Hz), 7.57 (s, 1H), 7.60 (d, 1H, J = 0.6 Hz), 7.39 (dd, 1H, J = 5.0, 1.0 Hz), 7.12 (dd, 1H, J = 5.0, 3.7 Hz), 3.48 (q, 2H, J = 7.3 Hz), 1.57 (t, 3H, J = 7.3 Hz) |
| 8-5 | | 261.3719 | B | 262 | CDCl3 7.98 (d, 1H, J = 1.0 Hz), 7.63 (s, 1H), 7.61 (d, 1H, J = 1.0 Hz), 7.54 (s, 1H), 7.48 (s, 1H), 7.41 (dd, 1H, J = 4.9, 1.9 Hz), 3.50 (q, 2H, J = 7.3 Hz), 1.57 (t, 3H, J = 7.3 Hz) |
| 8-6 | | 299.3538 | B | | CDCl3 8.99 (t, 1H, J = 2.0 Hz), 8.35 (dd, 1H, J = 7.9, 1.0 Hz), 7.82 (s, 1H), 7.72 (d, 1H, J = 1.3 Hz), 7.66 (t, 1H, J = 2.0 Hz), 7.56 (s, 1H), 3.56 (q, 2H, J = 7.4 Hz), 1.61 (t, 3H, J = 7.3 Hz) |
| 8-7 | | 291.3247 | C-D | 292 | CDCl3 7.93 (td, 1H, J = 10.8, 2.2 Hz), 8.35 (dt, 1H, J = 8.8, 2.0 Hz), 7.68 (s, 1H), 7.66 (s, 1H), 7.51 (s, 1H), 7.25 (q, 1H, J = 8.8 Hz), 3.52 (q, 2H, J = 7.3 Hz), 1.58 (t, 3H, J = 7.4 Hz) |
| 8-8 | | 330.3666 | C | | CDCl3 7.95 (d, 1H, J = 8.2 Hz), 7.59–7.30 (m, 3H), 7.02 (s, 1H), 6.96 (d, 1H, J = 5.6 Hz), 3.97 (s, 3H), 3.33 (q, 2H, J = 7.2 Hz), 1.58 (t, 3 H, J = 7.3 Hz) |

63
(Preparation of Intermidiates I)

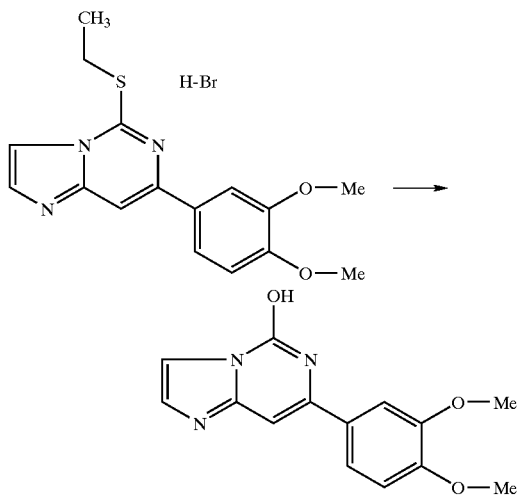

To a solution of 7-(3,4-dimethoxyphenyl)-5-ethylthioimidazo[1,2-c])pyrimidine (25.5 g, 64 mmol) (prepared in Example 1) in MeOH (500 ml) was added aquous KOH solution (2N, 135 ml, 270 mmol) and the resulting solution was heated under reflux overnight. The resulting mixture was cooled to room temperature and was partially concentrated under reduced pressure. The precipitate that emerged was collected, washed with water and then MeOH. This potassium salt was suspended in water and the suspension was neutralized with 1N HCl to obtain the free (non-salt) form of the product. The precipitate was collected and washed with water and then MeOH, and then dried in vacuo. (13 g, 75%)

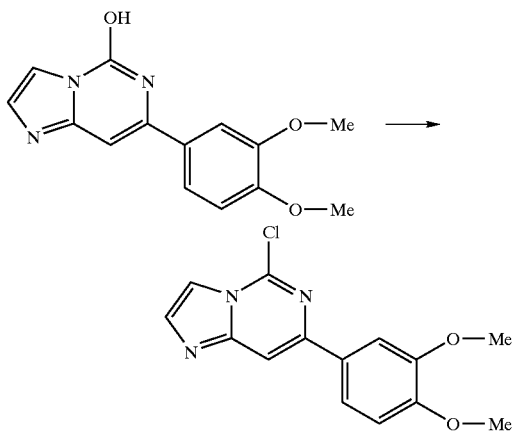

A solution of 5-hydroxy-7-(3,4-dimethoxyphenyl)-imidazo[1,2-c]pyrimidine (44 g, 162 mmol) and POCl₃ (500 g) was heated under ref lux for 4 hr. The reaction mixture was concentrated in vacuo, followed by the addition of ice-water. The solid was collected by filtration. The solid was then suspended in water and washed with saturated NaHCO₃ solution. The collected solid was dried in vacuo (47 g, 92%).

With the use of various compounds obtained by the same method as any of Examples 1–8 or by the similar method to any of Examples 1–8 above, various imidazopyrimidine intermediates having various C-7 substituents can be prepared.

64
(Preparation of Intermidiates II)

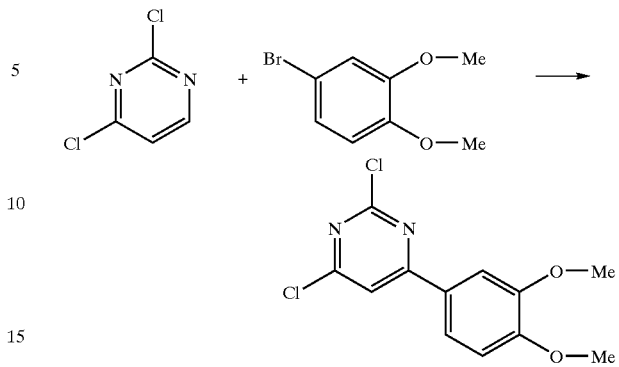

To the solution of 4-bromoveratrole (27.8, 128 mmol) in 160 ml of dry THF was added 75 ml of n-butyl lithium solution in hexane (1.59M) within 30 min. at −70° C. under Ar with stirring. The resulting white slurry was stirred at −70° C. for 1 hr. The solution of 2,4-dichloropyrimidine (14.9 g, 100 mmol) in 50 ml dry THF was added to the slurry at −30° C. under Ar with stirring within 30 min. The resulting solution was stirred at −30° C. for 1 h then 0° C. for 45 min. The reaction was quenched with a solution of acetic acid (6.4 ml, 104 mmol) and water(1 ml, 56 mmol) in THF. The mixture was stirred at room temperature for 5 min, cooled to 0° C., and treated with the solution of DDQ (2,3-dichloro-5,6-dicyano-p-benzoquinone, 22.7 g, 100 mmol) in 30 ml of THF. The mixture was stirred at room temperature for 10 min, cooled to 0° C., treated with 40 ml of 3M sodium hydroxide aqueous solution and stirred at 0° C. for 10 min, 300 ml of ethyl acetate was added to the mixture, the organic layer was separated, and dried with MgSO₄. After the solvent was evaporated, the residue was purified by column chromatography (Ethyl acetate/Hexane 1:4) to give the product (13.8 g, 48.4%).

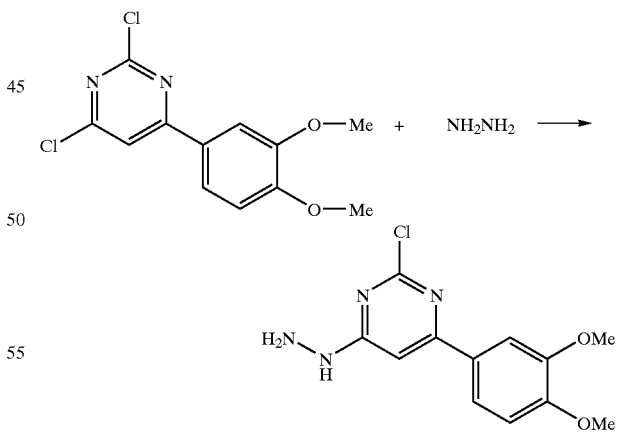

To 45 ml anhydrous hydrazine was added 2,4-dichloro-6-(3,4-dimethoxy-phenyl)-pyrimidine (7 g, 24.55 mmol) at 0° C. and the resulting slight yellow suspension was stirred for 30 min. The slight yellow precipitate was collected by filtration. The crude product was purified by column chromatography (EtOAc/Hex/Methanol 2:1:0.1) to give the product (3.9 g, 56.6%).

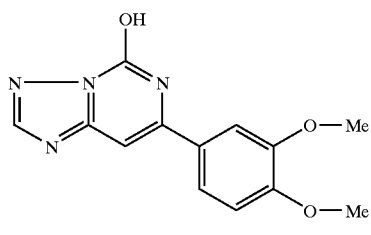

[2-Chloro-6-(3,4-dimethoxy-phenyl)-pyrimidin-4-yl]-hydrazine (1123 mg, 4 mmol) was added to 10 ml of formic acid and the mixture was stirred at 85° C. overnight, the resulting yellow solution was poured into 50 ml of ice water with stirring. The precipitate was collected by filtration and washed with water and ethanol to give product (1010 mg, 92.7%).

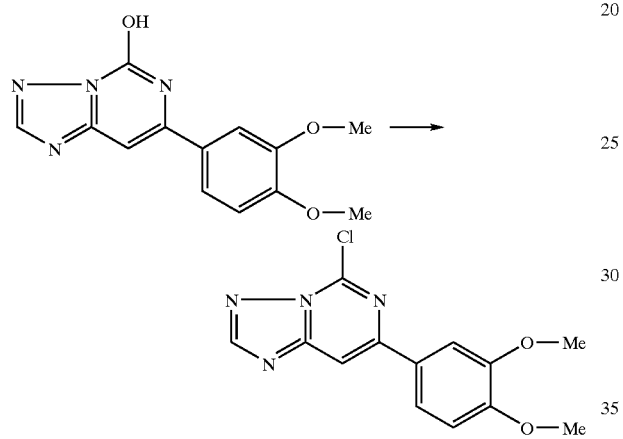

The suspension of 7-(3,4-dimethoxyphenyl)-[1,2,4]triazolo[1,5-c]pyrimidin-5-ol (1010 mg, 3.71 mmol) in 10 ml phosphorus oxychloride and N,N-diethylaniline (0.5 ml) was heated at 120° C. for 3 h. The phosphorus oxychloride was evaporated at vacuum and the residue was added to the mixture of 20 ml of crush ice and 15 ml of saturated NaHCO₃ aqueous solution. The mixture was extracted with 2×150 ml ethyl acetate and the combined extract was dried with MgSO₄. The solvent was evaporated at vacuum to give product as slight yellow solid (850 mg, 78.8%).

With the use of various compounds obtained by the same method as any of Examples 1–8 or by the similar method to any of Examples 1–8 above, various triazolopyrimidine intermediates having various C-7 substituents can be prepared.

Example 9

The mixture of 5-chloro-7-(3,4-dimethoxyphenyl)imidazo[1,2-c]pyrimidine (57.94 mg, 0.2 mmol), 1-(4-fluorophenyl)piperazine.2HCl (55.69 mg, 0.22 mmol), and diisopropylethylamine (85.31 mg, 0.66 mmol) in 3 ml of 2-propanol was stirred at 90° C. for 3 h, and cooled to room temperature. To the obtained mixture, 3 ml of ice water was added, the produced white solid was collected by filtration, and dried to give the pure product (56 mg, 64.6%) of 7-(3,4-Dimethoxyphenyl)-5-[4-(4-fluorophenyl)piperazin-1-yl]-imidazo[-1,2-c]pyrimidine.

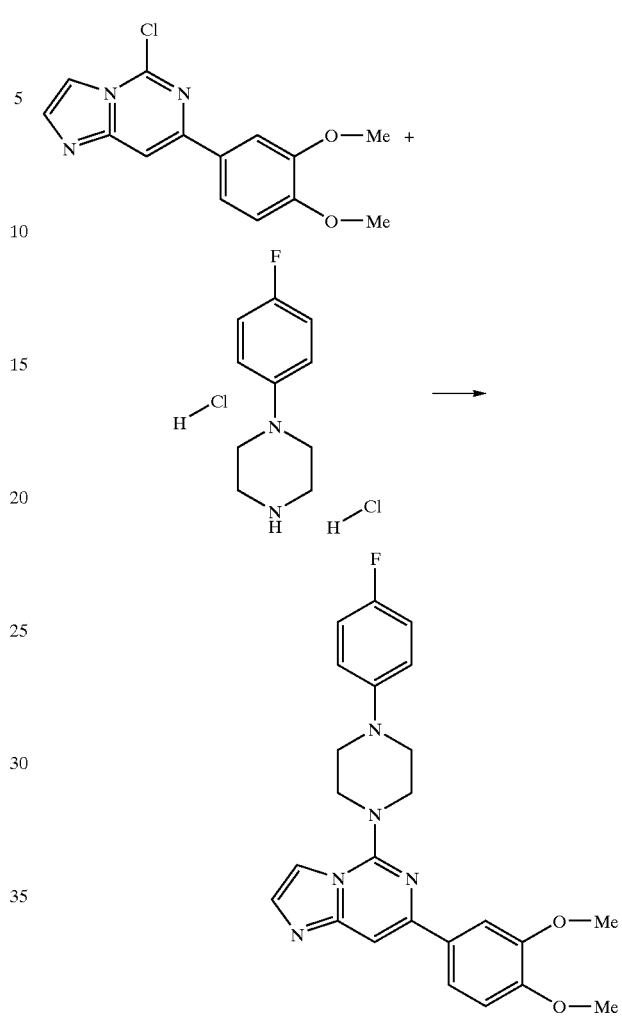

Molecular weight: 433.4846 Mass spectrometry: 434
Activity grade: C.

Example 10

The mixture of 5-chloro-7-(3,4-dimethoxyphenyl)-imidazo[1,2-c]pyrimidine (57.94 mg, 0.2 mmol), 4-aminomethylpyridine (23.79 mg, 0.22 mmol), and diisopropylethylamine (38.78, 0.3 mmol) in 2-propanol was stirred at 90° C. for 20 h, and cooled to room temperature. The solvent was evaporated, and 5 ml of ice water was added. Then the resulting product was extracted with 2×10 ml of ethyl acetate. The combined extract was dried over MgSO₄. Then the solvent was evaporated and 2 ml of ether was added. The produced solid was collected by filtration and dried to give pure product (38 mg, 52.6%) of [7-(3,4-dimethoxy-phenyl)-imidazo[1,2-c]pyrimidin-5-yl]pyridin-4-ylmethyl-amine.

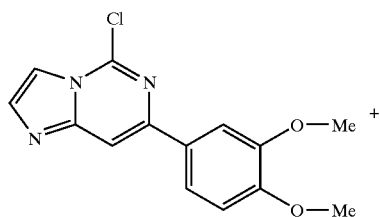
+
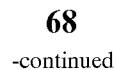
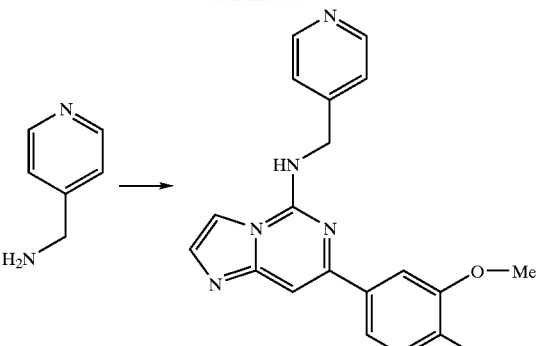
Molecular weight 361.4031 Mass spectrometry: 362
Activity grade: A
With the use of any of the intermediates I or II and according to the procedure that is similar to that of Example 9 or 10, following compounds shown in Table 9 below were prepared.
TABLE 9
| Ex. No. | MOLSTRUCTURE | MOLWEIGHT | Activity grade | MS | NMR |
|---|---|---|---|---|---|
| 9-1 | | 383.454 | B | 384 | |
| 9-2 | | 448.4827 | C | 449 | |
| 9-3 | | 341.4163 | C | 342 | |

TABLE 9-continued
| Ex. No. | MOLSTRUCTURE | MOLWEIGHT | Activity grade | MS | NMR |
|---|---|---|---|---|---|
| 9-4 | 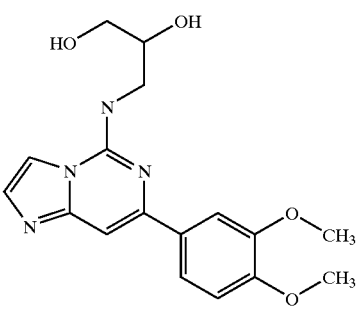 | 344.3733 | B | 345 | |
| 9-5 | 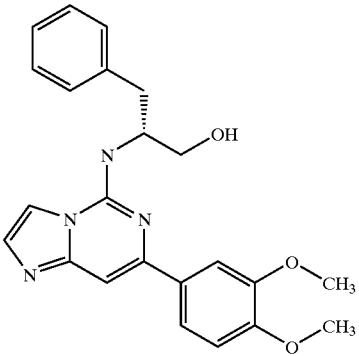 | 404.4727 | B | 405 | |
| 9-6 | 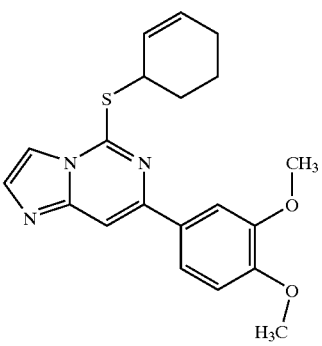 | 367.4733 | A | | |
| 9-7 | 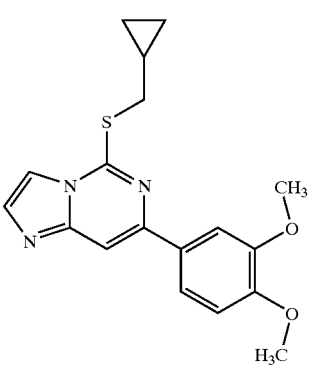 | 341.4351 | A | | |

TABLE 9-continued

| Ex. No. | MOLSTRUCTURE | MOLWEIGHT | Activity grade | MS | NMR |
|---|---|---|---|---|---|
| 9-8 | | 327.408 | A | | |
| 9-9 | | 329.4239 | A | | |
| 9-10 | | 360.4192 | B | | |
| 9-11 | | 298.3475 | A | | |
| 9-12 | | 284.3204 | B | | |

TABLE 9-continued

| Ex. No. | MOLSTRUCTURE | MOLWEIGHT | Activity grade | MS | NMR |
|---|---|---|---|---|---|
| 9-13 | | 372.4303 | B | | |
| 9-14 | | 381.8247 | | 382 | (CDCl3) 3.97 (3H, s), 4.06 (3H, s), 6.99 (1H, d, J = 8.5 Hz), 7.17 (1H, d, J = 7.9 Hz), 7.32–7.66 (3H, m), 7.80 (1H, d, J = 1.9 Hz), 8.18 (1H, br), 8.32 (2H, s), 8.37–8.39 (1H, m) |
| 9-15 | | 377.4062 | | 378 | (DMSO d-6) 2.09 (3H, s), 3.76 (3H, s), 3.77 (3H, s), 6.77–6.80 (1H, m), 6.99–7.14 (3H, m), 7.60–7.63 (2H, m), 7.72 (1H, s), 8.56 (1H, s), 9.42 (1H, s), 9.62 (1H, br) |
| 9-16 | | 363.3819 | A | 364 | (DMSO d-6) 3.85 (3H, s), 3.90 (3H, s), 6.29 (1H, d, J = 7.9 Hz), 7.12 (1H, d, J = 8.3 Hz), 7.52–7.67 (2H, m), 7.81–7.84 (2H, m), 7.92 (1H, s), 8.58 (1H, s), 8.62 (1H, br) |

TABLE 9-continued

| Ex. No. | MOLSTRUCTURE | MOLWEIGHT | Activity grade | MS | NMR |
|---|---|---|---|---|---|
| 9-17 | | 364.3666 | C | 365 | (DMSO d-6) 3.78 (3H, s), 3.80 (3H, s), 7.00 (1H, d, J = 8.4 Hz), 7.19–7.23 (1H, m), 7.34–7.37 (1H, m), 7.64–7.69 (2H, m), 7.78 (1H, s), 7.97 (1H, d, J = 3.6 Hz), 8.55 (1H, s), 9.80 (1H, br), 10.12 (1H, br) |
| 9-18 | | 398.4278 | C–D | 399 | (DMSO d-6) 3.84 (3H, s), 3.86 (3H, s), 7.12 (1H, d, J = 8.3 Hz), 7.52–7.56 (1H, m), 7.82–7.91 (3H, m), 8.07 (1H, d, J = 9.0 Hz), 8.32–8.35 (2H, m), 8.64–8.68 (2H, m), 8.83–8.86 (1H, m), 10.56 (1H, s) |
| 9-19 | | 439.4097 | A | 418 | (DMSO d-6) 3.83 (3H, s), 3.89 (3H, s), 6.36 (1H, d, J = 15.9 Hz), 7.13 (1H, d, J = 15.6 Hz), 7.09 (1H, d, J = 8.2 Hz), 7.53 (2H, d, J = 8.6 Hz), 7.77, 7.81, 7.99 (2H, d, J = 8.6 Hz), 8.55 (1H, s) |
| 9-20 | | 441.4256 | A | 420 | (DMSO d-6) 2.17 (2H, t, J = 8.3 Hz), 2.77 (2H, t, J = 7.45 Hz), 3.83 (3H, s), 3.87 (3H, s), 7.07 (1H, d, J = 8.3 Hz), 7.23 (2H, d, J = 8.4 Hz), 7.74–7.85 (5H, m), 8.54 (1H, s), 10.07 (1H, br) |

TABLE 9-continued

| Ex. No. | MOLSTRUCTURE | MOLWEIGHT | Activity grade | MS | NMR |
| --- | --- | --- | --- | --- | --- |
| 9-21 | | 435.446 | | 436 | |
| 9-22 | | 471.5639 | A | 472 | |
| 9-23 | | 432.4833 | A | 433 | |
| 9-24 | | 432.4833 | A | 433 | |

TABLE 9-continued

| Ex. No. | MOLSTRUCTURE | MOLWEIGHT | Activity grade | MS | NMR |
|---|---|---|---|---|---|
| 9-25 | | 446.5103 | B | 447 | |
| 9-26 | | 519.5649 | B | 520 | |
| 9-27 | | 411.9135 | A | 412 | (DMSO) 3.83 (3H, s), 3.85 (3H, s), 4.95 (2H, s), 7.09 (1H, d, J = 8.5 Hz), 7.28–7.39 (2H, m), 7.54 (1H, dd, J = 1.6 Hz, 7.7 Hz), 7.69–7.87 (5H, m), 8.03 (1H, s). |
| 9-28 | | 387.4609 | A | 388 | (DMSO) 1.17 (3H, t, J = 4.1 Hz), 2.99 (2H, t, J = 6.9 Hz), 3.72 (2H, t, J = 6.9 Hz), 3.83 (3H, s), 3.87 (3H, s), 4.10 (2H, q, J = 7.1 Hz), 7.07 (1H, d, J = 8.3 Hz), 7.69 (1H, d, J = 1.4 Hz), 7.76–7.82 (3H, m), 8.00 (1H, s). |

TABLE 9-continued

| Ex. No. | MOLSTRUCTURE | MOLWEIGHT | Activity grade | MS | NMR |
| --- | --- | --- | --- | --- | --- |
| 9-29 | | 404.4727 | A | 405 | |
| 9-30 | | 340.3851 | C | 341 | |
| 9-31 | | 396.4498 | B | 397 | |
| 9-32 | | 473.5362 | C | 474 | 2.58–2.69 (4H, m), 3.46–3.57 (6H, m), 3.81 (3H, s), 3.86 (3H, s), 6.00 (2H, s), 6.79–6.92 (3H, m), 7.04 (1H, d, J = 8.2 Hz), 7.59 (1H, s), 7.73–7.76 (4H, m) |

TABLE 9-continued

| Ex. No. | MOLSTRUCTURE | MOLWEIGHT | Activity grade | MS | NMR |
|---|---|---|---|---|---|
| 9-33 | | 415.4992 | C | 416 | (DMSO d-6) 3.42 (4H, t, J = 4.5 Hz), 3.67 (4H, t, J = 4.5 Hz), 3.82 (3H, s), 3.88 (3H, s), 6.83 (1H, t, J = 7.2 Hz), 7.02–7.07 (3H, m), 7.24–7.29 (2H, m), 7.63 (1H, s), 7.75–7.81 (3H, m), 7.85 (1H, s) |
| 9-34 | | 445.5256 | C | 446 | |
| 9-35 | | 460.4967 | C | 461 | |

TABLE 9-continued

| Ex. No. | MOLSTRUCTURE | MOLWEIGHT | Activity grade | MS | NMR |
|---|---|---|---|---|---|
| 9-36 | | 457.5368 | C | 458 | |
| 9-37 | | 353.4275 | B | 354 | (DMSO d-6) 2.33 (3H, s), 2.65 (4H, s), 3.53 (4H, s), 3.81 (3H, s), 3.87 (3H, s), 7.05 (1H, d, J = 8.4 Hz), 7.60 (1H, s), 7.73, 7.77 (4H, m) |
| 9-38 | | 416.4868 | B | 417 | |

TABLE 9-continued
| Ex. No. | MOLSTRUCTURE | MOLWEIGHT | Activity grade | MS | NMR |
|---|---|---|---|---|---|
| 9-39 | 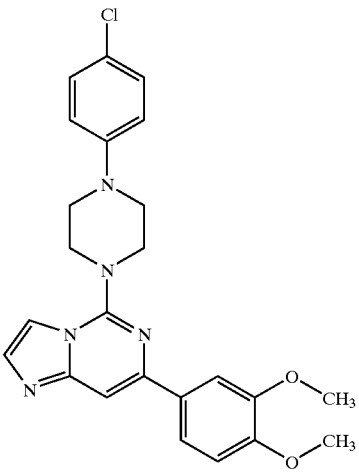 | 449.9442 | C | 450 | |
| 9-40 | 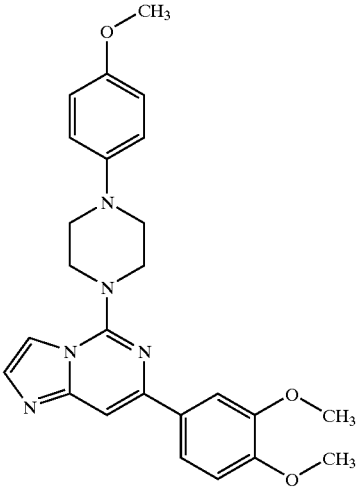 | 445.5256 | C | 446 | |
| 9-41 | 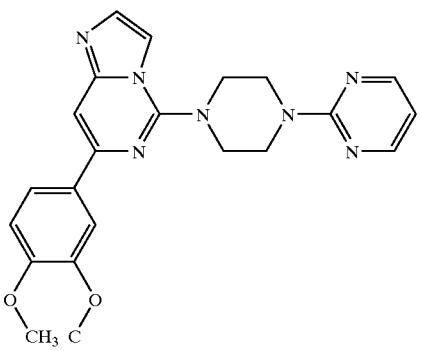 | 417.4743 | B | 418 | |

TABLE 9-continued

| Ex. No. | MOLSTRUCTURE | MOLWEIGHT | Activity grade | MS | NMR |
|---|---|---|---|---|---|
| 9-42 | | 484.3893 | C–D | 484, 486 | |
| 9-43 | | 445.5256 | C | 446 | (DMSO d-6) 3.43 (4H, t, J = 4.9 Hz), 3.70 (4H, t, J = 4.9 Hz), 3.74 (3H, s), 3.83 (3H, s), 3.89 (3H, s), 6.43 (1H, d, J = 8.1 Hz), 6.56 (1H, s), 6.62 (1H, d, J = 8.2 Hz), 7.09 (1H, d, J = 8.6 Hz), 7.16 (1H, t, J = 8.2 Hz), 7.76–7.84 (4H, m), 7.99 (1H, s) |
| 9-44 | | 429.5262 | C | 430 | |
| 9-45 | | 41.606 | C–D | 542 | |

TABLE 9-continued

| Ex. No. | MOLSTRUCTURE | MOLWEIGHT | Activity grade | MS | NMR |
|---|---|---|---|---|---|
| 9-46 | | 433.4709 | C | 434 | |
| 9-47 | | 433.4896 | C | 434 | (DMSO d-6) 3.30 (4H, t, J = 4.7 Hz), 3.67 (4H, t, J = 4.7 Hz), 3.82 (3H, s), 3.88 (3H, s), 6.99–7.21 (5H, m), 7.63 (1H, s), 7.75–7.84 (4H, m) |
| 9-48 | | 421.547 | C-D | 422 | |
| 9-49 | | 381.438 | B | 382 | |

TABLE 9-continued

| Ex. No. | MOLSTRUCTURE | MOLWEIGHT | Activity grade | MS | NMR |
|---|---|---|---|---|---|
| 9-50 | | 484.4851 | C–D | 485 | |
| 9-51 | | 383.454 | C | 384 | |
| 9-52 | | 389.4609 | B | 390 | (DMSO d-6) 1.32 (3H, t, J = 7.1 Hz), 3.61 (2H, q, J = 7.1 Hz), 3.79 (6H, s), 4.84 (2H, s), 6.99 (1H, d, J = 8.5 Hz), 7.42 (2H, d, J = 8.5 Hz), 7.56–7.67 (5H, m), 8.49 (2H, d, J = 8.5 Hz) |

TABLE 9-continued

| Ex. No. | MOLSTRUCTURE | MOLWEIGHT | Activity grade | MS | NMR |
|---|---|---|---|---|---|
| 9-53 | | 418.4998 | A | 419 | 2.50 (2H, p, J = 1.8 Hz), 3.30 (3H, s), 3.60 (2H, t, J = 7.2 Hz), 3.81 (3H, s), 3.85 (3H, s), 4.68 (1H, t, J = 4 Hz), 5.37 (1H, d, J = 4 Hz), 7.03 (1H, d, J = 9 Hz), 7.27–7.36 (5H, m), 7.53 (1H, s), 7.63 (1H, s), 7.70–7.74 (2H, m), 7.80 (1H, s) |
| 9-54 | | 338.4128 | B | 339 | |
| 9-55 | | 324.3857 | B | 325 | |
| 9-56 | | 326.4017 | B | 327 | (DMSO d-6) 1.27 (6H, t, J = 7.0 Hz), 3.57 (4H, q, J = 7.0 Hz), 7.05 (1H, d, J = 7.0 Hz), 7.57 (1H, s), 7.66 (2H, s), 7.73–7.75 (2H, m) |

TABLE 9-continued

| Ex. No. | MOLSTRUCTURE | MOLWEIGHT | Activity grade | MS | NMR |
|---|---|---|---|---|---|
| 9-57 | | 381.438 | A | 382 | |
| 9-58 | | 352.3962 | B | 353 | (DMSO d-6) 2.67 (4H, t, J = 6 Hz), 3.81 (3H, s), 3.85–3.89 (7H, m), 7.05 (1H, d, J = 8.3 Hz), 7.63 (1H, s), 7.73–7.80 (3H, m), 7.87 (1H, s) |
| 9-59 | | 428.5387 | C–D | 429 | |

TABLE 9-continued
| Ex. No. | MOLSTRUCTURE | MOLWEIGHT | Activity grade | MS | NMR |
|---|---|---|---|---|---|
| 9-60 | 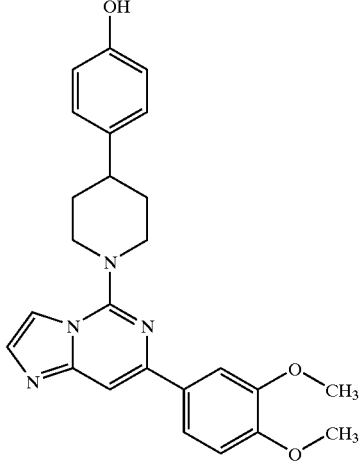 | 430.511 | B | 431 | |
| 9-61 | 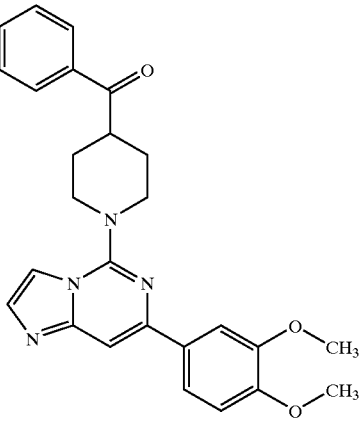 | 460.5126 | C–D | 461 | |
| 9-62 | 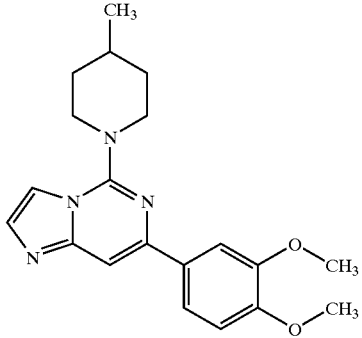 | 352.4399 | C | 353 | |

TABLE 9-continued

| Ex. No. | MOLSTRUCTURE | MOLWEIGHT | Activity grade | MS | NMR |
|---|---|---|---|---|---|
| 9-63 | | 421.547 | C | 422 | |
| 9-64 | | 464.956 | C | 465 | |
| 9-65 | | 368.4393 | B | 369 | |

TABLE 9-continued

| Ex. No. | MOLSTRUCTURE | MOLWEIGHT | Activity grade | MS | NMR |
|---|---|---|---|---|---|
| 9-66 | | 396.4498 | C | 397 | |
| 9-67 | | 396.4498 | C | 397 | (DMSO d-6) 1.90 (4H, t, J = 5.5 Hz), 3.57 (4H, t, J = 5.5 Hz), 3.81 (3H, s), 3.87 (3H, s), 3.96 (4H, s), 7.05 (1H, d, J = 8.3 Hz), 7.60 (1H, s), 7.73–7.77 (4H, m) |
| 9-68 | | 439.5215 | C | 440 | |
| 9-69 | | 354.4122 | B | 355 | |

TABLE 9-continued

| Ex. No. | MOLSTRUCTURE | MOLWEIGHT | Activity grade | MS | NMR |
|---------|--------------|-----------|----------------|-----|-----|
| 9-70 | Chiral | 435.4093 | C | 436 | |
| 9-71 | | 382.4227 | C–D | 383 | |
| 9-72 | | 411.4645 | C | 412 | |

TABLE 9-continued

| Ex. No. | MOLSTRUCTURE | MOLWEIGHT | Activity grade | MS | NMR |
|---|---|---|---|---|---|
| 9-73 | | 425.4916 | C–D | 426 | |
| 9-74 | | 367.4546 | B | 0 | |
| 9-75 | | 356.4497 | B | 357 | |
| 9-76 | | 355.4434 | C | 356 | |

TABLE 9-continued

| Ex. No. | MOLSTRUCTURE | MOLWEIGHT | Activity grade | MS | NMR |
|---|---|---|---|---|---|
| 9-77 | | 370.4116 | C | 371 | |
| 9-78 | Chiral | 367.4546 | C | 368 | |
| 9-79 | | 347.3797 | A | 347 | (CDCl3) d 3.96 (3H, s), 4.00 (3H, s), 6.99 (1H, d, J = 8.4 Hz), 7.20 (1H, t, J = 8 Hz), 7.44 (1H, t, J = 8 Hz), 7.51 (1H, s), 7.67 (1H, dd, J = 2 Hz, 8.4 Hz), 7.75 (1H, d, J = 2 Hz), 7.92 (1H, d, J = 8 Hz), 8.13 (1H, s), 8.31 (1H, s) |

TABLE 9-continued

| Ex. No. | MOLSTRUCTURE | MOLWEIGHT | Activity grade | MS | NMR |
| --- | --- | --- | --- | --- | --- |
| 9-80 | | 420.4721 | B | 420 | (DMSO-d6) d 3.73 (3H, s), 3.81 (3H, s), 3.83 (3H, s), 3.84 (3H, s), 4.77 (2H, d, J = 5.2 Hz), 6.47 (1H, dd, J = 2.4 Hz, 8.4 Hz), 6.61 (1H, d, J = 2.4 Hz), 7.09 (1H, d, J = 8.5 Hz), 7.32 (1H, d, J = 8.4 Hz), 7.51 (1H, s), 7.67 (1H, d, J = 2 Hz), 7.78 (1H, dd, J = 2 Hz, 8.5 Hz), 7.99 (1H, s), 8.42 (1H, s), 9.10 (1H, s) |
| 9-81 | | 313.3591 | B | 314 | |
| 9-82 | | 381.4773 | C | 382 | |
| 9-83 | | 413.4787 | A | 414 | |

TABLE 9-continued

| Ex. No. | MOLSTRUCTURE | MOLWEIGHT | Activity grade | MS | NMR |
|---|---|---|---|---|---|
| 9-84 | | 375.4299 | B | 376 | |
| 9-85 | | 471.5145 | C | 472 | |
| 9-86 | | 367.4505 | B | 368 | |
| 9-87 | | 312.3746 | A | 313 | (CD3OD) 1.06 (3H, t, J = 7.2), 1.84 (2H, q, J = 7.2), 3.67 (2H, t, J = 7.2), 3.89 (3H, s), 3.92 (3H, s), 7.03 (1H, d, J = 8.4), 7.22 (1H, s), 7.46 (1H, s), 7.69 (1H, dd, J = 2.1 and 6.3), 7.75 (2H, d, J = 2.1) |
| 9-88 | | 359.4067 | A | 360 | (DMSO) 3.67 (3H, s), 3.83 (3H, s), 3.90 (3H, s), 7.07 (1H, d, J = 9.0 Hz), 7.72 (3H, m), 7.91 (1H, s), 8.01 (1H, s). |

TABLE 9-continued

| Ex. No. | MOLSTRUCTURE | MOLWEIGHT | Activity grade | MS | NMR |
|---|---|---|---|---|---|
| 9-89 | | 373.4338 | B | 374 | (DMSO) 1.12 (3H, t, J = 7.1 Hz), 3.82 (3H, s), 3.90 (3H, s), 4.12 (2H, q, J = 7.1 Hz), 4.42 (2H, s), 7.05 (1H, d, J = 9.1 Hz), 7.72 (1H, d, J = 1.5 Hz), 7.75–7.78 (2H, m), 7.91 (1H, s), 8.01 (1H, s). |
| 9-90 | | 373.4338 | A | 374 | (DMSO) 3.01 (2H, t, J = 6.9 Hz), 3.64 (3H, s), 3.73 (2H, t, J = 6.9 Hz), 3.83 (3H, s), 3.87 (3H, s), 7.07 (1H, d, J = 8.3 Hz), 7.70 (1H, d, J = 1.4 Hz), 7.77 (1H, s), 7.80–7.82 (2H, m), 8.00 (1H, s). |
| 9-91 | | 373.4338 | B | 374 | (DMSO) 1.31 (3H, d, J = 7.1 Hz), 2.97–3.04 (1H, m), 3.65 (1H, dd, J = 6.3 Hz, 13.6 Hz), 3.76 (1H, dd, J = 7.3 Hz, 13.6 Hz), 3.83 (3H, s), 3.88 (3H, s), 7.07 (1H, d, J = 8.4 Hz), 7.69 (1H, d, J = 1.4 Hz), 7.77–7.82 (2H, m), 7.84 (1H, s), 7.99 (1H, s). |

TABLE 9-continued

| Ex. No. | MOLSTRUCTURE | MOLWEIGHT | Activity grade | MS | NMR |
|---|---|---|---|---|---|
| 9-92 | | 401.488 | B | 402 | (DMSO) 0.67 (3H, t, d = 7.3 Hz), 1.12 (2H, h, J = 7.6 Hz), 1.45 (2H, p, J = 6.8 Hz), 3.82 (3H, s), 3.90 (3H, s), 4.06 (2H, t, J = 6.8 Hz), 4.42 (2H, s), 7.03 (1H, d, J = 9.0 Hz), 7.73–7.77 (3H, m), 7.92 (1H, s), 8.01 (1H, s). |
| 9-93 | | 407.4514 | B | | (DMSO) 3.57 (3H, s), 3.77 (3H, s), 5.77 (1H, s), 6.92 (1H, d, J = 8.5 Hz), 7.25 (1H, s), 7.37 (1H, t, J = 7.9 Hz), 7.67 (1H, s), 7.68 (1H, s), 7.74 (1H, d, J = 7.9 Hz), 8.03 (2H, d, J = 8.2 Hz), 8.16 (1H, d, J = 8.2 Hz), 8.32 (1H, s). |
| 9-94 | | 465.5277 | A | | (CDCl3) 2.76 (2H, t, J = 7.6 Hz), 3.05 (2H, t, J = 7.6 Hz), 3.76 (3H, s), 3.78 (3H, s), 3.89 (3H, s), 6.71 (1H, s), 6.72 (1H, s), 6.83–6.85 (2H, m), 6.93 (1H, s), 6.96 (1H, d, 7.3 Hz), 7.61–7.67 (3H, m). |

TABLE 9-continued

| Ex. No. | MOLSTRUCTURE | MOLWEIGHT | Activity grade | MS | NMR |
|---|---|---|---|---|---|
| 9-95 | | 518.571 | A | | (CDCl3) d 2.62 (2H, broad t), 2.88 (2H, t, J = 6.5 Hz), 3.76 (4H, t, J = 4.7 Hz), 3.87 (3H, s), 3.98 (3H, s), 4.23 (2H, t, J = 5.8 Hz), 5.76 (1 H, broad s), 6.34 (1H, broad s), 6.99 (1H, d, J = 8.5 Hz), 7.14 (1H, s), 7.18 (1H, dd, J = 2.8, 9.2 Hz), 7.47 (1H, s), 7.60–7.67 (4H, m), 9.09 (1H, d, J = 9.2 Hz), 11.69 (1H, s). |
| 9-96 | | 475.5461 | A | | (CDCl3) d 2.60 (2H, broad t), 2.86 (2H, t, J = 6.0 Hz), 3.74 (4H, t, J = 4.7 Hz), 3.84 (3H, s), 3.92 (3H, s), 4.21 (2H, t, J = 6.0 Hz), 6.74 (1H, s), 6.96 (3H, m), 7.42 (1H, s), 7.47 (1H, s), 7.54–7.67 (5H, m). |
| 9-97 | | 524.5992 | C–D | | (DMSO d-6) d 2.58 (4H, broad t), 2.79 (2H, broad t), 3.61 (4H, t, J = 4.7 Hz), 3.85 (3H, s), 4.15 (2H, t, J = 5.4 Hz), 5.71 (2H, broad s), 6.55 (2H, m), 7.03 (2H, m), 7.21 (1H, s), 7.53–7.83 (5H, m). |

… TABLE 9-continued

| Ex. No. | MOLSTRUCTURE | MOLWEIGHT | Activity grade | MS | NMR |
|---|---|---|---|---|---|
| 9-98 | | 474.5184 | A | 475 | CDCl3 9.06 (d, 1H, J = 9.2 Hz), 7.68–7.65 (m, 3H), 7.46 (s, 1H), 7.25 (d, 2H, J = 2.9 Hz), 7.18 (dd, 1H, J = 9.1, 2.8 Hz), 7.02 (d, 1H, J = 7.9 Hz), 4.00 (s, 3H), 3.93 (t, 4H, J = 4.6 Hz), 3.88 (s, 3H), 3.16 (t, 4H, J = 4.4 Hz) |
| 9-99 | | 444.4973 | A | 445 | DMSO 12.93 (s, 1H), 9.06 (d, 1H, J = 8.5 Hz), 8052 (s, 1H), 7.99 (d, 1H, J = 8.2 Hz), 7.97 (s, 1H), 7.77 (s, 1H), 7.75–7.67 (m, 5H), 7.19 (t, 1H, J = 8.2 Hz), 6.99 (d, 1H, J = 8.5 Hz), 3.94 (s, 3H), 3.75 (t, 4H, J = 4.4 Hz), 3.05 (t, 4H, J = 4.4 Hz) |

Example 11

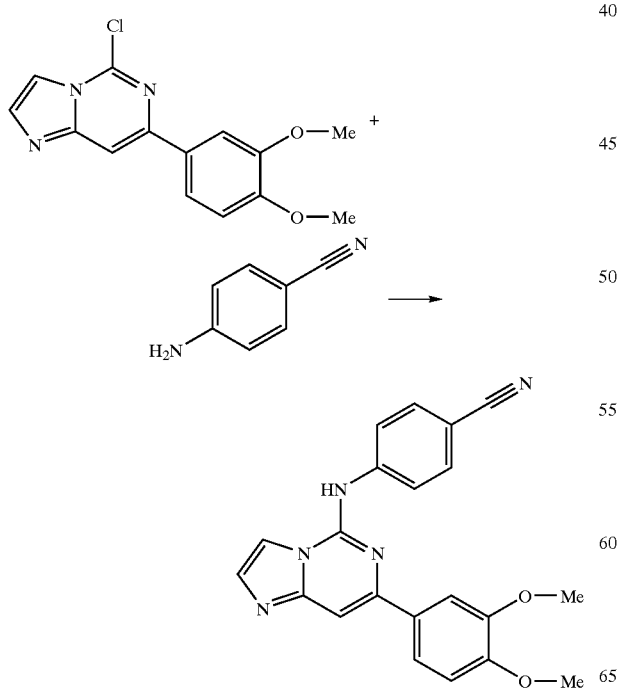

To the suspension of 5-chloro-7-(3,4-dimethoxyphenyl)imidazo[1,2-c]pyrimidine (57.94 mg, 0.2 mmol) and 4-aminobenzonitrile (35.44 mg, 0.3 mmol) in the mixture of 2.5 ml 2-propanol and 1.5 ml H$_2$O was added conc.HCl. Then the mixture was stirred at 85 to 90° C. overnight, and cooled to room temperature. The produced solid was collected by filtration and purified by preparative TLC to give the desired product of 4-[7-(3,4-dimethoxy-phenyl)-imidazo[1,2-c]pyrimidin-5-ylamino]-benzonitrile. (38 mg, 51.2%).

Molecular weight 371.3983 Mass spectrometry: 372
Activity grade: A

With the use of any of the intermediates I or II and according to the procedure that is similar to that of Example 11, following compounds shown in Table 10 below were prepared.

TABLE 10

| Ex. No. | MOLSTRUCTURE | MOLWEIGHT | grade | MS | NMR |
|---|---|---|---|---|---|
| 11-1 | | 417.4715 | B | | (MeOD) 2.88 (3H, s), 2.90 (3H, s), 3.79 (3H, s), 3.88 (3H, s), 7.04 (1H, d, J = 8.3 Hz), 7.43–7.53 (2H, m), 7.57–7.66 (4H, m), 7.86 (1H, d, J = 8.3 Hz), 7.95 (1H, d, J = 2.3 Hz), 8.16 (1H, d, J = 2.3 Hz) |
| 11-2 | | 390.4456 | A | | (MeOD) 2.28 (3H, s), 3.74 (3H, s), 3.82 (3H, s), 3.84 (3H, s), 6.85 (1H, dd, J = 2.9, 8.6 Hz), 6.92 (2H, m), 7.34 (2H, m), 7.49–7.56 (3H, m), 7.93 (1H, s) |
| 11-3 | | 415.4119 | A | | (DMSO) 3.88 (3H, s), 3.94 (3H, s), 7.17 (1H, d, J = 8.3 Hz), 7.73 (1H, d, J = 7.9 Hz), 7.80 (1H, d, J = 1.9 Hz), 7.85 (1H, s), 7.86 (1H, dd, J = 1.9, 8.3 Hz), 7.94 (1H, d, J = 1.5 Hz), 8.08 (1H, d, J = 7.9 Hz), 8.13 (1H, m), 9.27 (1H, d, J = 8.3 Hz), 12.35 (1H, s), 12.28 |
| 11-4 | | 460.5375 | A | | (d8-DMSO) 1.11 (6H, s), 2.84 (2H, s), 3.39 (1H, m), 3.83 (3H, s), 3.85 (3H, s), 7.11 (1H, d, J = 9.0 Hz), 7.27 (2H, d, J = 8.3 Hz), 7.68–7.83 (5H, m), 8.07 (1H, m), 8.75 (1H, m), 10.49 (1H, s) |

TABLE 10-continued

| Ex. No. | MOLSTRUCTURE | MOLWEIGHT | grade | MS | NMR |
|---|---|---|---|---|---|
| 11-5 | | 444.4944 | A | | (d8-DMSO) 1.72–1.85 (1H, m), 2.10–2.19 (1H, m), 2.42–2.58 (1H, m), 2.66–2.75 (1H, m), 2.81–2.91 (2H, m), 2.93–3.01 (1H, m), 3.31 (2H, m), 3.83 (3H, s), 3.85 (3H, s), 7.08 (1H, d, J = 8.2 Hz), 7.20 (1H, d, J = 8.2 Hz), 7.55–7.85 (6H, m), 8.39 (1H, s) |
| 11-6 | | 440.4814 | C | 441 | |
| 11-7 | | 360.4192 | A | 361 | |
| 11-8 | | 376.4185 | A | 377 | |

TABLE 10-continued

| Ex. No. | MOLSTRUCTURE | MOLWEIGHT | grade | MS | NMR |
|---|---|---|---|---|---|
| 11-9 | | 360.4192 | A | | (DMSO d-6) 2.31 (3H, s), 3.81 (3H, s), 3.86 (3H, s), 7.03 (1H, d, J = 8.6 Hz), 7.25 (2H, d, J = 8.7 Hz), 7.60 (2H, s), 7.67–7.80 (4H, m), 8.26 (1H, s), 9.45 (1H, s) |
| 11-10 | | 430.3898 | B | 431 | |
| 11-11 | | 389.4173 | A | | (DMSO d-6) 3.81 (3H, s), 3.83 (3H, s), 7.01 (1H, d, J = 8.5 Hz), 7.39 (1H, s), 7.51 (1H, t, J = 7.9 Hz), 7.63–7.65 (3H, m), 7.73 (1H, s), 7.74 (1H, s), 7.99 (1H, s), 8.06 (1H, d, 7.9 Hz), 8.30 (1H, s), 8.44 (1H, s), 9.67 (1H, s) |
| 11-12 | | 387.4042 | A | | (DMSO d-6) 3.82 (3H, s), 3.85 (3H, s), 7.12 (1H, d, J = 8.5 Hz), 7.76–7.80 (3H, m), 7.93 (1H, d, J = 8 Hz), 8.04 (1H, s), 8.13 (1H, s), 8.51 (1H, s), 8.95 (1H, s), 10.95 (1H, s) |

TABLE 10-continued

| Ex. No. | MOLSTRUCTURE | MOLWEIGHT | grade | MS | NMR |
|---|---|---|---|---|---|
| 11-13 | | 404.432 | C | 405 | |
| 11-14 | | 515.5738 | A | 516 | |
| 11-15 | | 377.4061 | A | 378 | |
| 11-16 | | 346.3921 | A | 347 | |

TABLE 10-continued

| Ex. No. | MOLSTRUCTURE | MOLWEIGHT | grade | MS | NMR |
|---|---|---|---|---|---|
| 11-17 | | 376.4185 | A | 377 | |
| 11-18 | | 360.4192 | A | | |
| 11-19 | | 404.4291 | ND | 405 | |
| 11-20 | | 436.4931 | A | 437 | |
| 11-21 | | 432.4833 | A | 433 | |

TABLE 10-continued

| Ex. No. | MOLSTRUCTURE | MOLWEIGHT | grade | MS | NMR |
|---|---|---|---|---|---|
| 11-22 | | 404.4291 | A | 405 | |
| 11-23 | | 447.4543 | A | 448 | |
| 11-24 | | 418.4562 | A | 419 | (DMSO-d6) 2.58 (2H, t, J = 7.5 Hz), 2.87 (2H, t, J = 7.4 Hz), 3.85 (6H, s),7.11 (1H, d, J = 8.21 Hz), 7.34 (2H, d, J = 8.2 Hz), 7.70–7.80 (5H, m), 8.07 (1H, d, J = 1.4 Hz), 8.77 (1H, ), 10.51 (1H, s) |
| 11-25 | | 390.4456 | B | 377 | (DMSO-d6) 3.56 (3H, s), 3.58 (3H, s), 3.83 (3H, s), 3.89 (3H, s), 6.28 (1H, s), 7.07 (2H, d, J = 8.5 Hz), 7.16 (1H, d, J = 8.3 Hz), 7.25 (1H, d, J = 1.5 Hz), 7.29–7.32 (1H, m), 7.36–7.42 (1H, m), 7.67 (1H, s), 7.79–7.84 (2H, m) |

TABLE 10-continued

| Ex. No. | MOLSTRUCTURE | MOLWEIGHT | grade | MS | NMR |
|---|---|---|---|---|---|
| 11-26 | | 404.4291 | A | 405 | (DMSO-d6) 3.85 (3H, s), 3.88 (6H, s), 7.14 (1H, d, J = 8.5 Hz), 7.75–7.81 (3H, m), 8.06–8.13 (5H, m), 8.77 (1H, d, J = 1.6 Hz), 10.71 (1H, s) |
| 11-27 | | 454.5085 | A | 455 | (DMSO d-6) 3.49 (2H, t, J = 6.4Hz), 3.73 (2H, q, J = 6.4 Hz), 3.82 (3H, s), 3.87 (3H, s), 7.03 (1H, d, J = 8.5 Hz), 7.64–7.79 (6H, m), 8.31 (2H, s), 8.55 (1H, s), 9.88 (1H, s) |
| 11-28 | | 390.402 | A | 391 | |
| 11-29 | | 362.3914 | A | 363 | (DMSO d-6) 3.82 (3H, s), 3.83 (3H, s), 6.85 (1H, s), 6.88 (1H, s), 7.07 (1H, d, J = 9.1 Hz), 7.58–7.61 (3H, m), 7.71–7.73 (2H, m), 7.88 (1H, s), 8.48 (1H, s), 9.94 (1H, s) |

TABLE 10-continued

| Ex. No. | MOLSTRUCTURE | MOLWEIGHT | grade | MS | NMR |
|---|---|---|---|---|---|
| 11-30 | | 362.3914 | A | 363 | (DMSOd-6) 3.85 (3H, s), 3.86 (3H, s), 6.67 (1H, d, J = 7.8 Hz), 7.11 (1H, d, J = 8.6 Hz), 7.24 (1H, t, J = 8.6 Hz), 7.31 (1H, d, J = 7.8 Hz), 7.44 (1H, s), 7.71 (1H, s), 7.79 (1H, s), 8.07 (1H, s), 8.91 (1H, s), 10.52 (1H, s) |
| 11-31 | | 362.3914 | A | 363 | (DMSO d-6) 3.75 (3H, s), 3.77 (3H, s), 6.91 (1H, t, J = 7.6 Hz), 6.96–7.00 (2H, m), 7.13 (1H, t, 7.9 Hz), 7.52 (1H, s), 7.55–7.61 (4H, m), 8.23 (1H, s) |
| 11-32 | | 431.4986 | A | 432 | |
| 11-33 | | 391.3896 | A | 392 | (DMSO d-6) 3.84 (3H, s), 3.89 (3H, s), 7.12 (1H, d, J = 8.3 Hz), 7.74–7.80 (2H, m), 7.83 (1H, s), 7.90 (1H, s), 8.24 (1H, s), 8.25 (2H, d, J = 9.4 Hz), 8.32 (2H, d, J = 9.4 Hz), 8.67 (1H, s), 8.88 (1H, brs), 10.3 (1H. brs) |

TABLE 10-continued

| Ex. No. | MOLSTRUCTURE | MOLWEIGHT | grade | MS | NMR |
|---|---|---|---|---|---|
| 11-34 | | 389.4609 | A | 390 | (DMSO d-6) 3.80 (3H, s), 3.84 (3H, s), 6.82 (1H, d, J = 9.2 Hz), 7.02 (1H, d, J = 8.6 Hz), 7.54 (1H, s), 7.60 (1H, s), 7.63–7.68 (3H, m), 7.72 (1H, s), 8.23 (1H, s), 9.36 (1H, s) |
| 11-35 | | 402.4568 | A | 403 | |
| 11-36 | | 389.4173 | A | 390 | |
| 11-37 | | 376.4185 | A | 377 | (DMSO d-6) 3.84 (6H, s), 4.58 82H, s), 7.11 (1H, d, J = 8.7 Hz), 7.17 (1H, d, J = 7.9 Hz), 7.40 (1H, t, J = 7.9 Hz), 7.71–81 (3H, m), 7.89 (1H, s), 8.08 (1H, s), 8.92 (1H, s), 10.28 (1H, brs), 10.64 (1H, s) |

TABLE 10-continued

| Ex. No. | MOLSTRUCTURE | MOLWEIGHT | grade | MS | NMR |
|---|---|---|---|---|---|
| 11-38 | | 422.8776 | A | 387 | (DMSO d-6) 3.80 (3H, s), 3.85 (3H, s), 7.12 (1H, J = 8.6 Hz), 7.60 (1H, d, J = 8.7 Hz), 7.75 (1H, s), 7.79–7.86 (3H, m), 8.08–8.15 (3H, m), 8.84 (1H, s), 10.66 (1H, s), 13.10 (1H, brs) |
| 11-39 | | 382.3729 | A | 383 | |
| 11-40 | | 400.3634 | A | 401 | |
| 11-41 | | 444.8534 | A | 445 | (DMSO d-6) 3.83 (6H, s), 7.09 (1H, 8.7 Hz), 7.64–7.82 (5H, m), 8.11 (1H, s), 8.16 (1H, q, J = 4.1 Hz), 8.34 (1H, s), 11.36 (1H, brs) |

TABLE 10-continued

| Ex. No. | MOLSTRUCTURE | MOLWEIGHT | grade | MS | NMR |
|---|---|---|---|---|---|
| 11-42 | | 404.4291 | C–D | 405 | (DMSO d-6) 3.70 (3H, s), 3.83 (3H, s), 3.88 (3H, s), 6.69 (1H, s), 7.06–7.14 (3H, m), 7.45 (1H, s), 7.78–7.83 (2H, m), 7.91 (1H, s), 7.94 (1H, s) |
| 11-43 | | 405.4167 | A | 406 | (DMSO d-6) 3.73 (3H, s), 3.82 (3H, s), 3.88 (3H, s), 7.05–7.09 (2H, m), 7.16 (2H, d, J = 9.4 Hz), 7.58 (1H, s), 7.75–7.77 (2H, m), 8.09 (1H, s), 8.19 (2H, d, J = 9.4 Hz) |
| 11-44 | | 396.4 | A | 397 | |
| 11-45 | | 394.8642 | B | 395 | |

TABLE 10-continued

| Ex. No. | MOLSTRUCTURE | MOLWEIGHT | grade | MS | NMR |
|---|---|---|---|---|---|
| 11-46 | | 444.4169 | B | 445 | (DMSO d-6) 3.66 (3H, s), 3.83 (3H, s), 3.88 (3H, s), 8.59 (1H, s), 7.08 (1H, d, J = 8.3 Hz), 7.25–7.28 (2H, m), 7.38–7.45 (3H, m), 7.78–7.84 (2H, m), 7.88 (1H, s) |
| 11-47 | | 386.4574 | A | 387 | |
| 11-48 | | 399.4561 | A | 400 | |
| 11-49 | | 390.4456 | B | 391 | |
| 11-50 | | 394.8642 | A | 395 | (DMSO d-6) 3.66 (3H, s), 3.83 (3H, s), 3.88 (3H, s), 6.63 (1H, s), 6.99–7.09 (2H, m), 7.31–7.43 (4H, m), 7.88–7.83 (2H, m), 7.88 (1H, s) |

TABLE 10-continued

| Ex. No. | MOLSTRUCTURE | MOLWEIGHT | grade | MS | NMR |
|---|---|---|---|---|---|
| 11-51 | | 404.4291 | B | 405 | |
| 11-52 | | 461.7491 | A | 425 | (DMSO d-6) 3.82 (3H, s), 3.88 (3H, s), 7.05 (1H, d, J = 8.3 Hz), 7.34 (1H, d, J = 7.9 Hz), 7.42 (1H, t, J = 7.9 Hz), 7.63 (1H, s), 7.68–7.72 (3H, m), 7.87 (1H, d, J = 6.8 Hz), 8.27 (1H, s), 8.32 (1H, s), 9.65 (1H, s) |
| 11-53 | | 364.3825 | A | 365 | (DMSO d-6) 3.74 (3H, s), 3.77 (3H, s), 6.96 (1H, d, J = 8.3 Hz), 7.36–7.40 (3H, m), 7.53–7.62 (2H, m), 8.19 (1H, s), 9.57 (1H, s) |
| 11-54 | | 382.3729 | A | 383 | (DMSO d-6) 3.75 (3H, s), 3.77 (3H, s), 6.97 (1H, d, J = 9 Hz), 7.22 (1H, d, J = 7.5 Hz), 7.18–7.25 (2H, m), 7.55 (1H, s), 7.57 (1H, s), 7.72 (1H, d, J = 7.7 Hz), 8.15 (1H, s), 9.58 (1H, s) |

TABLE 10-continued

| Ex. No. | MOLSTRUCTURE | MOLWEIGHT | grade | MS | NMR |
|---|---|---|---|---|---|
| 11-55 | | 380.8371 | A | 381 | (DMSO d-6) 3.71 (3H, s), 3.76 (3H, s), 6.95 (1H, d, J = 8.3 Hz), 7.38 (1H, d, J = 7.8 Hz), 7.37–7.51 (2H, m), 7.56 (1H, s), 7.62 (1H, s), 7.73 (1h, d, J = 7.9 Hz), 8.18 (1H, s), 9.59 (1H, brs) |
| 11-56 | | 391.3896 | A | 392 | (DMSO d-6) 3.83 (3H, s), 3.88 (3H, s), 6.97 (1H, J = 8.3 Hz), 7.50 (2H, s), 7.66 (2H, s), 7.69 ( 1H, s), 7.753 (1H, s), 8.03 (2H, s), 8.25 (1H, s), 10.17 (1H, brs) |
| 11-57 | | 382.3729 | A | 383 | (DMSO d-6) 3.82 (3H, s), 3.87 (3H, s), 7.05 (1H, d, J = 8.3 Hz), 7.49–7.73 (6H, m), 8.12–8.24 (2H, m), 9.71 (1H, s) |
| 11-58 | | 412.8795 | A | 377 | (DMSO d-6) 3.81 (3H, s), 3.85 (3H, s), 3.86 (3H, s), 6.83 (1H, d, J = 8.7 Hz), 7.12 (1H, J = 8.3 Hz), 7.37–7.46 (2H, m), 7.62 (1H, s), 7.73–7.77 (3H, m), 8.08 (1H, s), 10.48 (1H, s) |

TABLE 10-continued

| Ex. No. | MOLSTRUCTURE | MOLWEIGHT | grade | MS | NMR |
|---|---|---|---|---|---|
| 11-59 | | 388.4297 | A | 389 | (DMSO d-6) 2.63 (3H, s), 3.82 (3H, s), 3.83 (3H, s), 7.03 (1H, d, J = 8.7 Hz), 7.63–7.78 (6H, m), 822 (1H, d, J = 6.2 Hz), 8.29 (1H, s), 8.50 (1H, s), 9.72 (1H, s) |
| 11-60 | | 364.3825 | A | 365 | (DMSO d-6) 3.81 (3H, s), 3.85 (3H, s), 7.03 (1H, d, J = 8.7 Hz), 7.26–7.32 (2H, m), 7.62 (2H, s), 7.65–7.71 (2H, m), 7.87–7.92 (2H, m), 8.24 (s, 1H), 9.57 (1H, s) |
| 11-61 | | 380.8371 | A | 381 | (DMSO d-6) 3.81 (3H, s), 3.86 (3H, s), 7.05 (1H, d, J = 8.3 Hz), 7.50 (2H, d, J = 9 Hz), 7.62–7.72 (4H, m), 7.94 (2H, d, J = 9 Hz), 8.25 (1H, s) |
| 11-62 | | 434.3287 | A | 362 | (DMSO d-6) 3.85 (3H, s), 3.86 (3H, s), 7.11 (1H, d, J = 8.5 Hz), 7.37 (2H, d, J = 8.7 Hz), 7.72–7.77 (2H, m), 7.94 (2H, d, J = 8.7 Hz), 8.10 (1H, s), 8.92 (1H, s), 10.85 (1H, s) |

TABLE 10-continued

| Ex. No. | MOLSTRUCTURE | MOLWEIGHT | grade | MS | NMR |
|---|---|---|---|---|---|
| 11-63 | | 385.429 | A | 386 | (DMSO d-6) 3.81 (3H, s), 3.86 (3H, s), 4.05 (2H, s), 7.05 (1H, d, J = 8.4 Hz), 7.42 (2H, d, J = 8.5 Hz), 7.62–7.73 (4H, m), 7.92 (2H, d, 8.5 Hz), 8.28 (1H, s), 9.61 (1H, s) |
| 11-64 | | 389.4173 | A | 390 | (DMSO d-6) 3.86 (3H, s), 3.89 (3H, s), 7.13 (1H, d, J = 8.5 Hz), 7.30 (1H, t, J = 7.6 Hz), 7.72–7.82 (4H, m), 7.97–8.04 (3H, m), 8.14 (1H, s), 8.55 (1H, s), 8.72 (1H, d, J = 8.3 Hz), 13.16 (1H, s) |
| 11-65 | | 406.445 | A | 407 | 3.74 (3H, s), 3.77 (3H, s), 3.78 (3H, s), 3.81 (3H, s), 6.63 (1H, d, J = 8.6 Hz), 6.74 (1H, d, J = 2.6 Hz), 6.95 (1H, d, J = 8.3 Hz), 7.50–7.57 (5H, m), 8.18 (1H, s), 8.98 (1H, s) |
| 11-66 | | 388.4326 | A | 389 | (DMSO d-6) 3.94 (3H, s), 3.97 (3H, s), 6.98 (1H, d, J = 8.9 Hz), 7.36 (1H, d, J = 8.7 Hz), 7.46 (1H, s), 7.58–7.63 (3H, m), 8.15 (1H, s), 8.47 (1H, d, J = 8.7 Hz), 8.93 (1H, s), 9.50 (1H, s) |

TABLE 10-continued

| Ex. No. | MOLSTRUCTURE | MOLWEIGHT | grade | MS | NMR |
|---|---|---|---|---|---|
| 11-67 | | 461.3545 | A | 389 | (DMSO d-6) 3.86 (3H, s), 3.90 (3H, s), 7.12 (1H, J = 8.5 Hz), 7.75–7.83 (3H, m), 7.98 (2H, d, J = 8.7 Hz), 8.09 (1H, s), 829 (2H, 8.7 Hz), 9.05 (1H, s), 9.12 (1H, s), 9.34 (2H, s), 11.20 (1H, s) |
| 11-68 | | 506.4365 | A | 434 | |
| 11-69 | | 430.3899 | A | 431 | (DMSO d-6) 3.82 (3H, s), 3.87 (3H, s), 7.03 (1H, d, J = 8.3 Hz), 7.14 (1H, d, J = 7.2 Hz), 7.57 (1H, t, J = 8.3 Hz), 7.64 (1H, s), 7.69–7.72 (3H, m), 7.90 (1H, d, J = 7.2 Hz), 8.13 (1H, s), 8.29 (1H, s), 9.76 (1H, s) |
| 11-70 | | 427.8506 | A | 392 | |

TABLE 10-continued

| Ex. No. | MOLSTRUCTURE | MOLWEIGHT | grade | MS | NMR |
|---|---|---|---|---|---|
| 11-71 | | 414.3905 | A | 415 | (DMSO d-6) 3.82 (3H, s), 3.87 (3H, s), 7.07 (1H, d, J = 9 Hz), 7.64 (1H, s), 7.71–7.73 (3H, m), 7.80 (2H, d, J = 8.7 Hz), 8.16 (2H, d, J = 8.7 Hz), 8.30 (1H, s), 9.89 (1H, brs) |
| 11-72 | | 439.9054 | A | 404 | |
| 11-73 | | 481.5779 | A | 482 | (DMSO d-6) 0.78 (3H, t, J = 7.5 Hz), 1.22 (2H, h, J = 7.5 Hz), 2.79 (2H, q, J = 6 Hz), 3.81 (3H, s), 3.87 (3H, s), 7.01 (1H, d, J = 8.7 Hz), 7.53–7.56 (2H, m), 7.64–7.70 (4H, m), 7.77 (1H, d, J = 8.5 Hz), 8.22 (1H, d, J = 8.5 Hz), 8.30 (1H, s), 8.44 (1H, |
| 11-74 | | 541.9079 | A | 433 | (DD3OD) 2.97 (6H, s), 3.43 (2H, t, J = 6.0), 3.62 (2H, t, J = 6.0), 3.87 (3H, s), 3.90 (3H, s), 6.96 (2H, d, J = 8.7), 7.06 (1H, d, J = 8.1), 7.57 (1H, s), 7.64 (2H, d, J = 8.7), 7.72–7.77 (2H, m), 7.93 (1H, d, J = 2.1), 8.33 (1H, s) |

TABLE 10-continued

| Ex. No. | MOLSTRUCTURE | MOLWEIGHT | grade | MS | NMR |
|---|---|---|---|---|---|
| 11-75 | | 456.8839 | A | 421 | (DMSO-d6) 3.81 (3H, s), 3.83 (3H, s), 3.88 (3H, s), 7.08 (1H, d, J = 8.4), 7.35 (1H, dd, J = 3.0 and 8.7), 7.53 (1H, d, J = 3.0), 7.63–7.71 (3H, m), 7.98 (1H, d, J = 8.7), 8.11 (1H, d, J = 1.8), 8.36 (1H, d, J = 1.8), 11.06 (1H, s) |
| 11-76 | | 461.928 | A | 426 | (DMSO-d6) 3.85 (3H, s), 3.87 (3H, s), 7.14 (1H, d, J = 8.4), 7.37 (2H, s(br)), 7.73–8.97 (3H, m), 7.93 (2H, d, J = 8.4), 8.10–8.15 (3H, m), 8.97 (1H, s), 11.02 (1H, s) |
| 11-77 | | 390.3972 | A | 391 | |
| 11-78 | | 551.7661 | A | | (DMSO d-6) 3.86 (3H, s), 3.90 (3H, s), 7.13 (1H, d, J = 8.6 Hz), 7.72 (1H, s), 7.79–7.81 (2H, m), 7.97 (1H, s), 8.04–8.10 (3H, m), 8.33 (1H, s), 8.52 (1H, d, J = 8.7 Kz), 8.59 (1H, brs), 12.95 (1H, brs) |

TABLE 10-continued

| Ex. No. | MOLSTRUCTURE | MOLWEIGHT | grade | MS | NMR |
|---|---|---|---|---|---|
| 11-79 | | 515.5671 | A | 516 | |
| 11-80 | | 497.9366 | A | | |
| 11-81 | | 425.9176 | A | | (DMSO) 3.83 (3H, s), 3.85 (3H, s), 4.29–4.51 (6H, broad s), 6.75 (1H, s), 7.12 (1H, d, J = 8.4 Hz), 7.33 (3H, s), 7.73 (2H, m), 7.80 (1H, d, J = 8.4 Hz), 8.11 (1H, d, J = 1.4 Hz), 8.78 (1H, s), 10.44 (1H, s) |
| 11-82 | | 511.0229 | A | | (DMSO) 3.30 (6H, m), 3.53 (2H, t, J = 6.1 Hz), 3.84 (3H, s), 3.85 (3H, s), 3.91 (4H, m), 6.79 (2H, AB, J = 8.9 Hz), 7.10 (1H, d, J = 8.9 Hz), 7.58 (2H, AB, J = 8.9 Hz), 7.62 (1H, s), 7.73 (1H, s), 7.76 (1H, m), 8.09 (1H, d, J = 2.3 Hz), 8.75 (1H, d, J = 2.3 Hz), 10.41 (1H, s) |

TABLE 10-continued
| Ex. No. | MOLSTRUCTURE | MOLWEIGHT | grade | MS | NMR |
|---|---|---|---|---|---|
| 11-83 | 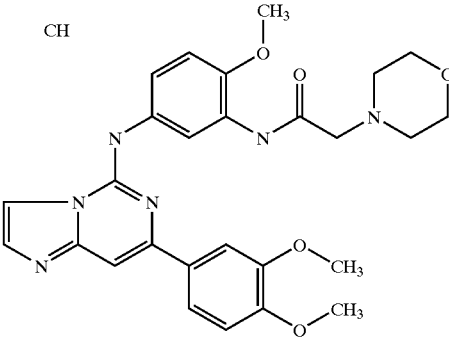 | 555.0319 | B | | (DMSO) 3.46 (4H, broad s), 3.81 (3H, s), 3.83 (4H, m), 3.84 (3H, s), 3.90 (3H, s), 4.17 (2H, broad s), 7.10 (1H, d, J = 8.5 Hz), 7.22 (1H, d, J = 9.0 Hz), 7.68 (3H, m), 7.80 (1H, dd, J = 2.0, 8.5 Hz), 8.08 (1H, d, J = 2.0 Hz), 8.43 (1H, s), 8.85 (1H, s), 10.05 (1H, s), 10.66 (1H, s) |
| 11-84 | 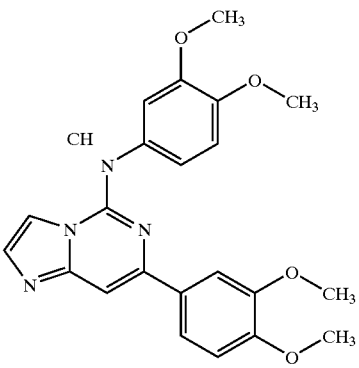 | 442.906 | A | 407 | (CD3OD) 3.85 (3H, s), 3.87 (3H, s), 3.88 (3H, s), 3.90 (3H, s), 7.06 (1H, dd, J = 3.6 and 8.4), 7.31 (1H, dd, J = 2.4 and 8.4), 7.43 (1H, d, J = 2.4), 7.56 (1H, s), 7.74–7.79 (2H, m), 7.92 (1H, d, J = 2.1), 8.29 (1H, d, J = 1.8) |
| 11-85 | 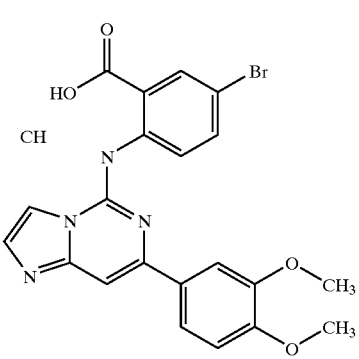 | 505.759 | A | 469 | (DMSO-d6) 3.84 (3H, s), 3.85 (3H, s), 7.11 (1H, d, J = 8.4), 7.67 (1H, d, J = 1.8), 7.72–7.78 (2H, m), 7.97 (1H, dd, J = 2.4 and 8.7), 8.13 (2H, dd, J = 2.1 and 13.2), 8.24–8.30 (2H, m), 11.68 (1H, s) |
| 11-86 | 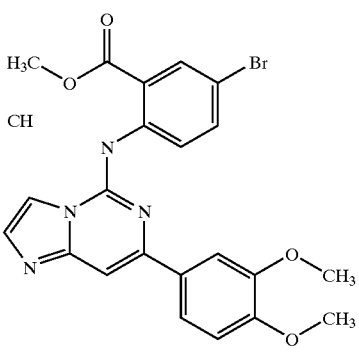 | 519.7861 | A | 485 | (DMSO-d6) 3.61 (3H, s), 3.82 (3H, s), 3.83 (3H, s), 7.08 (1H, d, J = 8.4), 7.60 (1H, d, J = 1.8), 7.68 (1H, dd, J = 2.1 and 8.7), 7.76 (1H, s), 7.98–8.10 (4H, m), 8.35 (1H, s), 10.87 (1H, s) |

TABLE 10-continued

| Ex. No. | MOLSTRUCTURE | MOLWEIGHT | grade | MS | NMR |
|---|---|---|---|---|---|
| 11-87 | | 479.7395 | A | 445 | (CD3OD) 3.81 (3H, s), 3.88 (3H, s), 7.32 (1H, d, J = 8.4), 7.51 (1H, m), 7.53–7.60 (2H, m), 7.61–7.71 (2H, m), 7.99 (1H, d, J = 2.4), 8.28 (1H, d, J = 2.1) |
| 11-88 | | 496.1941 | A | 461 | (CD3OD) 3.79 (3H, s), 3.85 (3H, s), 6.98 (1H, d, J = 9.0), 7.42 (1H, s), 7.53–7.61 (4H, m), 7.71–7.79 (2H, m), 7.99 (1H, s) |
| 11-89 | | 438.877 | A | 403 | (DMSO) 3.81 (3H, s), 3.84 (3H, s), 7.02 (1H, d, J = 8.4 Hz), 7.11 (1H, d, J = 8.4 Hz), 7.33 (1H, dd, J = 1.9, 8.4 Hz), 7.49 (1 H, d, J= 1.6 Hz), 7.67 (1H, s), 7.71 (1H, d, J = 1.9 Hz), 7.76 (1H, dd, J = 1.9, 8.4 Hz), 8.06 (1H, d, J = 2.1 Hz), 8.62 (1H, d, J = 1.9 Hz), 10.29 (1H, s), 10.65 (1H, s), 10.73 (1H, s) |
| 11-90 | | 525.0554 | A | 489 | (DMSO) 2.04 (2H, quint., J = 7.7 Hz), 3.20 (6H, m), 3.84 (3H, s), 3.85 (3H, s), 3.90 (6H, m), 6.83 (2H, d, J = 7.4 Hz), 7.11 (1H, d, J = 9.0 Hz), 7.62 (3H, m), 7.75 (2H, m), 8.08 (1H, d, J = 2.2 Hz), 8.81 (1H, d, J = 2.2 Hz), 10.48 (1H, s) |

TABLE 10-continued

| Ex. No. | MOLSTRUCTURE | MOLWEIGHT | grade | MS | NMR |
|---|---|---|---|---|---|
| 11-91 | | 475.5522 | A | 476 | (DMSO d-6) 2.58 (4H, t, J = 4.4 Hz), 2.81 (2H, t, J = 5.6 Hz), 3.74 (4H, t, J = 4.4Hz), 3.91 (6H, s), 4.11 (2H, t, J = 5.6 Hz), 6.90–6.94 (3H, m), 7.40 (1H, s), 7.54–7.68 (6H, m), 7.87 (1H, s) |
| 11-92 | | 428.8789 | A | 393 | (CD3OD) 3.90 (9H, s(br)), 6.99–7.13 (3H, m), 7.43 (1H, d, J = 2.4), 7.56 (1H, s), 7.74 (1H, dd, J = 1.8 and 6.3), 7.85 (1H, d, J = 1.8), 7.93 (1H, d, J = 2.1), 8.31 (1H, s) |
| 11-93 | | 428.8789 | A | 393 | (CD3OD) 3.78 (3H, s), 3.80 (3H, s), 3.87 (3H, s), 6.57–6.59 (2H, m), 7.02 (1H, d, J = 8.4), 7.42 (1H, d, J = 8.4), 7.49 (1H, s), 7.64–7.67 (m, 2H), 7.87 (1H, d, J = 2.1), 8.20 (2H, d, J = 1.5) |
| 11-94 | | 418.4998 | C | 419 | (CDCl3) 1.00 (3H, t, J = 7.4 Hz), 1.48–1.58 (2H, m), 1.80 (2H, quint., J = 6.5 Hz), 3.93 (3H, s), 3.95 (3H, s), 3.99 (2H, t, J = 6.5 Hz), 6.55 (1H, s), 6.91–6.98 (3H, m), 7.37 (1H, s), 7.48 (1H, s), 7.57–7.61 (3H, m), 7.64 (1H, d, J = 1.5 Hz), 7.68 (1H, d, J = 2.0 Hz) |
| 11-95 | | 430.3899 | A | 431 | (CDCl3) 3.94 (6H, s), 6.76 (1H, s), 6.97 (1H, d, J = 8.4 Hz), 7.29 (1H, AB, J = 8.9 Hz), 7.46 (1H, s), 7.54 (1H, s), 7.60 (1H, dd, J = 2.0, 8.4 Hz), 7.65 (1H, d, J = 2.0 Hz), 7.69 (1H, d, J = 1.4 Hz), 7.79 (2H, AB, J = 8.9 Hz) |

TABLE 10-continued

| Ex. No. | MOLSTRUCTURE | MOLWEIGHT | grade | MS | NMR |
|---|---|---|---|---|---|
| 11-96 | | 455.9048 | A | 420 | (MeOD) 3.90 (3H, s), 3.92 (6H, s), 7.09 (1H, d, J = 8.2 Hz), 7.22 (1H, dd, J = 2.9, 9.2 Hz), 7.48 (1H, d, J = 2.9 Hz), 7.58 (1H, s), 7.75 (1H, s), 7.76 (1H, m), 7.96 (2H, m), 8.68 (1H, d, J = 9.2 Hz) |
| 11-97 | | 504.7743 | A | 468, 469 | (DMSO) 3.85 (3H, s), 3.90 (3H, s), 7.13 (1H, d, J = 8.5 Hz), 7.73 (1H, s), 7.80 (2H, m), 7.90–7.95 (2H, m), 8.07 (2H, s), 8.20 (1H, s), 8.59 (1H, s), 8.70 (1H, d, J = 8.9 Hz), 12.9 (1H, s) |
| 11-98 | | 404.4727 | A | 405 | (DMSO) 1.29 (6H, d, J = 6.0 Hz), 3.80 (3H, s), 3.83 (3H, s), 4.61 (1H, sept., J = 6.0 Hz), 7.00 (2H, AB, J = 8.9 Hz), 7.03 (1H, m), 7.58 (2H, AB, J = 8.9 Hz), 7.67 (1H, dd, J = 1.9, 8.4 Hz), 7.74 (3H, m), 8.22 (1H, s), 9.39 (1H, s) |
| 11-99 | | 439.9054 | A | 404 | (MeOD) 2.93 (3H, s), 3.85 (3H, s), 3.90 (3H, s), 6.99 (1H, d, J = 7.4 Hz), 7.20 (1H, t, J = 6.9 Hz), 7.47–7.54 (2H, m), 7.61–7.66 (2H, m), 7.81 (1H, d, J = 7.7 Hz), 7.85 (1H, s), 7.95 (1H, s), 8.73 (1H, d, J = 7.7 Hz) |

TABLE 10-continued

| Ex. No. | MOLSTRUCTURE | MOLWEIGHT | grade | MS | NMR |
|---|---|---|---|---|---|
| 11-100 | | 394.409 | A | 395 | (DMSO) 3.81 (3H, s), 3.86 (3H, s), 3.86 (3H, s), 7.05 (1H, d, J = 8.5 Hz), 7.24 (1H, t, J = 9.3 Hz), 7.54 (1H, d, J = 8.9 Hz), 7.61 (2H, s), 7.68 (1H, dd, J = 1.9, 8.5 Hz), 7.74 (1H, d, J = 1.9 Hz), 7.99 (1H, dd, J = 2.5, 13.9 Hz), 8.23 (1H, s), 9.54 (1H, s) |
| 11-101 | | 535.3856 | A | | (DMSO d-6) 2.63 (2H, t, J = 4.7 Hz), 2.88 (2H, t, J = 7.7 Hz), 3.85 (3H, s), 3.92 (3H, s), 7.12 (1H, d, J = 9 Hz), 7.55 (1H, d, J = 8.7 Hz), 7.72 (1H, brs), 7.81–7.84 (3H, m), 7.88 (1H, s), 8.33 (1H, brs), 8.56 (1H, s), 8.96 (1H, s, 8.6 Hz) |
| 11-102 | | 463.323 | A | | (DMSO d-6) 3.85 (3H, s), 3.92 (3H, s), 7.12 (1H, d, J = 9 Hz), 7.22 (1H, t, J = 7.3 Hz), 7.66 (1H, t, J = 7.3 Hz), 7.75 (1H, brs), 7.82–7.85 (2H, m), 7.90–7.95 (2H, m), 8.36 (1H, brs), 8.58 (1H, s), 9.07 (1H, d, 8.2 Hz) |
| 11-103 | | 496.784 | A | | (DMSO d-6) 3.84 (3H, s), 3.86 (3H, s), 7.10 (1H, d, J = 8.4 Hz), 7.70 (1H, d, J = 8.7 Hz), 7.76–7.86 (4H, m), 8.05 (1H, s), 8.33 (1H, s), 8.63 (1H, s), 10.30 (1H, s) |

TABLE 10-continued

| Ex. No. | MOLSTRUCTURE | MOLWEIGHT | grade | MS | NMR |
|---|---|---|---|---|---|
| 11-104 | | 483.4578 | A | | (DMSO d-6) 2.64 (2H, t, J = 7.8 Hz), 2.89 (2H, t, J = 4.8 Hz), 3.85 (3H, s), 3.90 (3H, s), 7.12 (1H, d, J = 8.3 Hz), 7.57 (1H, d, J = 8.6 Hz), 7.73–7.80 (3H, m), 7.87–7.94 (4H, m), 8.48 (1H, s), 8.75 (1H, d, J = 8.5 Hz) |
| 11-105 | | 475.5025 | A | | (DMSO d-6) 1.89 (2H, p, J = 7.4 Hz), 2.27 (2H, t, J = 4.4 Hz), 2.65 (2H, t, J = 7.4 Hz), 3.83 (3H, s), 3.90 (3H, s), 7.08 (1H, d, J = 8.5 Hz), 7.51 (1H, d, J = 7.0 Hz), 7.68–7.78 (5H, m), 7.83 (1H, s), 7.91 (1H, s), 8.49 (1H, s), 8.93 (1H, d, J = 6.8 Hz), 12.06 (1H, brs), |
| 11-106 | | 549.4124 | A | | |
| 11-107 | | 497.4846 | A | | |

TABLE 10-continued

| Ex. No. | MOLSTRUCTURE | MOLWEIGHT | grade | MS | NMR |
|---|---|---|---|---|---|
| 11-108 | | 498.4727 | A | | (DMSO d-6) 1.81 (2H, p, J = 7.3 Hz), 2.02 (2H, t, J = 7.3 Hz), 2.58 (2H, t, J = 7.3 Hz), 3.83 (3H, s), 3.90 (3H, s), 7.09 (1H, d, J = 8.3 Hz), 7.36–7.67 (3H, m), 7.79–7.83 (3H, m), 8.39 (1H, brs), 8.87 (1H, d, J = 8.5 Hz) |
| 11-109 | | 434.4102 | A | | (DMSO d-6) 3.86 (3H, a), 3.87 (3H, s), 7.11 (1H, d, J = 8.8 Hz), 7.71 (1H, s), 7.85–7.88 (2H, m), 7.90 (1H, s), 7.98 (1H, s), 8.11–8.12 (2H, m), 8.23–8.26 (2H, m), 8.82 (1H, s), 13.10 (1H, brs) |
| 11-110 | | 503.9688 | A | | (DMSO-d6) 3.85 (3H, s), 3.86 (3H, s), 6.74 (4H, m(br)), 7.14 (1H, d, J = 8.4), 7.74–7.87 (5H, m), 7.99–8.07 (2H, m), 8.07 (1H, d, J = 2.1), 8.67 (1H, d, J = 1.8), 10.63 (1H, s) |
| 11-111 | | 504.5878 | C | | (CDCl3) 2.45 (4H, t, J = 4.6 Hz), 2.65 (2H, t, J = 6.1 Hz), 3.19 (2H, t, J = 6.1 Hz), 3.70 (4H, t, J = 4.6 Hz), 3.89 (3H, s), 3.92 (3H, s), 3.93 (3H, s), 4.84 (1H, s), 6.78 (2H, m), 6.91 (1H, d, J = 2.6 Hz), 6.95 (2H, m), 7.41 (1H, s), 7.45 (1H, s), 7.61 (1H, d, J = 1.3 Hz), 7.63 (1H, d, J = 2.0 Hz), 7.66 (1H, s) |

TABLE 10-continued

| Ex. No. | MOLSTRUCTURE | MOLWEIGHT | grade | MS | NMR |
|---|---|---|---|---|---|
| 11-112 | | 492.5768 | B | | (CDCl3) 2.31 (3H, s), 2.59 (2H, t, J = 5.3 Hz), 2.70 (2H, t, J = 6.1 Hz), 3.26 (2H, t, J = 6.1 Hz), 3.63 (2H, t, J = 5.3 Hz), 3.87 (3H, s), 3.93 (3H, s), 3.94 (3H, s), 6.76 (1H, d, J = 8.5 Hz), 6.92 (1H, s), 6.95 (1H, m), 7.02 (1H, s), 7.09 (1H, dd, J = 2.4, 8.5 Hz), |
| 11-113 | CH | 461.928 | A | | (CD3OD) 3.98 (3H, s), 4.02 (s, 3H), 7.20 (1H, d, J = 8.5), 7.59 (1H, t, J = 7.5), 7.79–7.88 (4H, m), 8.08 (1H, d, J = 2.0), 8.16–8.22 (2H, m), 8.59 (1H, d, J = 8.0) |
| 11-114 | CH | 461.928 | A | | (DMSO-d6) 3.85 (3H, s), 3.86 (3H, s), 7.09 (1H, d, J = 8.5), 7.44 (2H, s), 7.70 (3H, d, J = 5.0), 7.78–7.84 (2H, m), 8.06–8.15 (2H, m), 8.38 (1H, s), 8.65 (1H, s), 10.58 (1H, s) |
| 11-115 | CH | 516.0194 | A | | (DMSO-d6) 1.66–1.69 (4H, m), 3.17–3.18 (4H, m), 3.85 (3H, s), 3.87 (3H, s), 7.14 (1H, d, J = 8.5), 7.75–7.82 (3H, m), 7.93 (2H, d, J = 8.5), 8.07 (1H, d, J = 2.0), 8.18 (2H, d, J = 8.5), 8.76 (1H, s), 10.79 (1H, |

TABLE 10-continued

| Ex. No. | MOLSTRUCTURE | MOLWEIGHT | grade | MS | NMR |
|---|---|---|---|---|---|
| 11-116 | CH | 532.0184 | A | | (DMSO-d6) 2.91 (4H, t(br), J = 4.5), 3.66 (4H, t(br), J = 4.5), 7.15 (1H, d, J = 8.5), 7.76–7.88 (5H, m), 8.11–8.22 (3H, m), 8.76–8.79 (1H, s(br)), 10.86–10.98 (1H, s(br)) |
| 11-117 | CH | 466.9267 | A | | (DMSO) 3.37 (3H, s), 3.38 (3H, s), 3.80 (3H, s), 3.83 (3H, s), 7.11 (1H, d, J = 8.3 Hz), 7.26 (1H, d, J = 8.3 Hz), 7.51 (1H, dd, J = 1.9, 8.3 Hz), 7.63 (1H, d, J = 1.5 Hz), 7.68 (1H, d, J = 1.9 Hz), 7.70 (1H, s), 7.77 (1H, dd, J = 1.9, 8.3 Hz), 8.08 (1H, d, J = 1.9 Hz) |
| 11-118 | CH | 452.8999 | A | | (DMSO) 3.32 (3H, s), 3.81 (3H, s), 3.84 (3H, s), 7.10 (1H, d, J = 8.3 Hz), 7.18 (1H, d, J = 8.3 Hz), 7.42 (1H, dd, J = 1.9, 8.3 Hz), 7.56 (1H, d, J = 1.9 Hz), 7.68 (1H, s), 7.71 (1H, d, J = 1.9 Hz), 7.76 (1H, dd, J = 1.9, 8.3 Hz), 8.07 (1H, d, J = 1.9 Hz), 8.64 (1H, d, |
| 11-119 | | 424.479 | A | | (DMSO d-6) 3.82 (6H, s), 7.01 (1H, d, J = 9.0 Hz), 7.50 (1H, br), 7.58–7.75 (4H, m), 7.88 (2H, s), 8.02 (1H, d, J = 7.6 Hz), 8.43 (1H, d, J = 7.9 Hz), 9.73 (1H, br) |

TABLE 10-continued

| Ex. No. | MOLSTRUCTURE | MOLWEIGHT | grade | MS | NMR |
|---------|--------------|-----------|-------|-----|-----|
| 11-120 | | 424.479 | A | | (DMSO d-6) 3.25 (3H, s), 3.82 (3H, s), 3.87 (3H, s), 7.02 (1H, d, J = 8.6 Hz), 7.64–7.79 (5H, m), 8.28–8.30 (3H, m), 8.57 (1H, br), 9.88 (1H, br) |
| 11-121 | | 407.8592 | B | | (CDCl3) 3.74 (3H, s), 3.81 (3H, s), 7.08 (1H, d, J = 8.5 Hz), 7.54–7.58 (2H, m), 7.63–7.65 (1H, m), 7.75–7.78 (2H, m), 7.87–7.90 (1H, m), 8.04 (1H, d, J = 7.9 Hz), 8.09 (1H, s), 8.51 (1H, s), 10.94 (1H, bs). |
| 11-122 | | 439.4939 | A | | (DMSO) 3.57 (3H, s), 3.80 (3H, s), 3.82 (3H, s), 7.03 (1H, d, J = 8.1 Hz), 7.40 (1H, s), 7.66 (3H, m), 7.72 (1H, s), 7.80 (3H, s), 7.90 (1H, d, J = 5.4 Hz), 8.57 (1H, d, J = 8.1 Hz), 9.46 (1H, s) |
| 11-123 | | 453.5207 | A | | (DMSO d-6) 2.58 (6H, s), 3.78 (3H, s), 3.79 (3H, s), 7.00 (1H, d, J = 9.0 Hz), 7.45–7.50 (1H, m), 8.43 (1H, d, J = 8.3 Hz), 9.61 (1H, br) |

TABLE 10-continued

| Ex. No. | MOLSTRUCTURE | MOLWEIGHT | grade | MS | NMR |
|---|---|---|---|---|---|
| 11-124 | CH | 397.864 | A | | |
| 11-125 | | 460.5312 | B | | (DMSO d-6) 1.76–1.86 (2H, m), 2.27 (2H, t, 7.5 Hz), 2.62 (2H, t, J = 7.5 Hz), 3.62 (3H, s), 3.83 (3H, s), 3.88 (3H, s), 6.40 (1H, s), 7.06–7.11 (3H, m), 7.24–7.26 (2H, m), 7.32 (1H, d, J = 1.5 Hz), 7.78–7.85 (3H, m), 12.04 (1H, br) |
| 11-126 | | 474.558 | 10000 | | (DMSO d-6) 1.35 (3H, t, J = 4.2 Hz), 1.78–1.85 (2H, m), 2.20–2.28 (2H, m), 3.82 (3H, s), 3.88 (3H, s), 4.11–4.18 (2H, m), 6.31 (1H, s), 7.08–7.10 (3H, m), 7.25–7.26 (2H, m), 7.30 (1H, s), 7.76 (1H, s), 7.79–7.82 (2H, m), 12.00 (1H, br) |
| 11-127 | | 424.479 | A | | (DMSO), 3.22 (3H, s), 3.82 (3H, s), 3.88 (3H, s), 7.08 (1H, d, J = 9.0 Hz), 7.23 (1H, s), 7.65 (1H, d, J = 1.5 Hz), 7.74 (2H, s), 7.98 (2H, d, J = 8.7 Hz), 8.21 (2H, d, J = 8.7 Hz), 8.30 (1H, s), 9.94 (1H, s) |

TABLE 10-continued

| Ex. No. | MOLSTRUCTURE | MOLWEIGHT | grade | MS | NMR |
|---|---|---|---|---|---|
| 11-128 | | 432.4816 | A | | (DMSOd-6) 3.11 (36H, s), 3.83 (3H, s), 3.88 (3H, s), 6.47 (1H, d, J = 9 Hz), 7.05 (1H, d, J = 8.5 Hz), 7.52 (1H, brs), 7.69–7.84 (6H, m), 8.18 (1H, brs), 8.47 (1H, s) |
| 11-129 | | 404.432 | A | 405 | |

Example 12

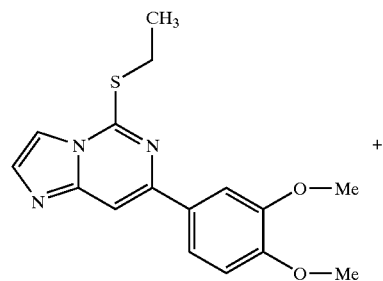

+

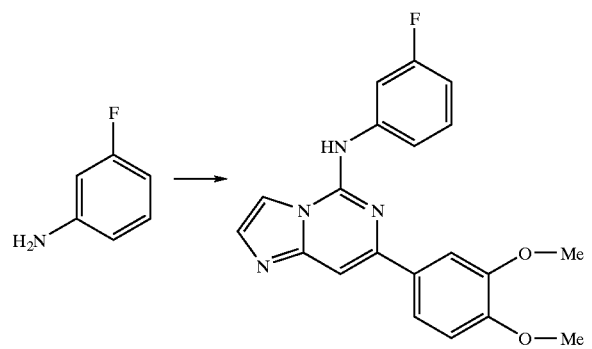

To the solution of m-fluoroaniline (88.90 mg, 0.8 mmol) in 1.5 ml of dry DMSO was added, potassium tert-butoxide (94.26 mg, 0.84 mmol), and 5-ethylsulfenyl-7-(3,4-dimethoxyphenyl)-imidazo[1,2-c]pyrimidin (126.16 mg, 0.4 mmol). The resulting solution was stirred overnight and 3 ml of ice water was added. The produced precipitate was collected by filtration, and washed with water, 2-propanol, and ether to give crude product of (3-fluorophenyl)-[7-(3,4-dimethoxyphenyl)-imidazo[1,2-c]pyrimidin-5-yl]amine. The crude product was purified by preparative TLC to give the pure product (127.000 mg, 87.1%).

Mass spectrometry: 365 Activity grade: A

With the use of any of the intermediates I or II and according to the procedure that is similar to that of Example 12, following compounds shown in Table 11 below were prepared.

TABLE 11

| Ex. No. | MOLSTRUCTURE | MOLWEIGHT | Activity grade | MS | NMR |
|---|---|---|---|---|---|
| 12-1 | | 459.5527 | B | | (CDCl3) 2.54 (4H, bs), 2.59–2.64 (2H, m), 2.79–2.87 (2H, m), 3.68–3.77 (4H, m) 3.94 (3H, S), 3.97 (3H, s), 6.78 (1 H, bs), 6.95 (1H, d, J = 7.5 Hz), 7.22–7.28 (3H, m), 7.45 (1H, s), 7.49 (1H, s), 7.59–7.62 (1H, m), 7.65–7.71 (4H, m) |
| 12-2 | | 386.4166 | A | 387 | |
| 12-3 | | 347.3796 | A | 348 | |
| 12-4 | | 377.4061 | A | | (DMSO d-6) 3.80 (3H, s), 3.83 (3H, s), 3.88 (3H, s), 6.94 (1H, d, J = 8.9 Hz), 7.02 (1H, d, 8.5 Hz), 7.61–7.68 (4H, m), 8.17 (1H, s), 8.19 (1H, s), 8.56 (1H, s), 9.59 (1H, s) |

TABLE 11-continued
| Ex. No. | MOLSTRUCTURE | MOLWEIGHT | Activity grade | MS | NMR |
|---|---|---|---|---|---|
| 12-5 | 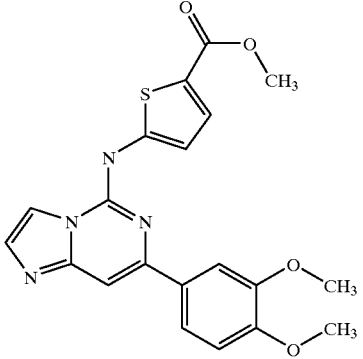 | 410.4549 | B | 411 | |
| 12-6 | 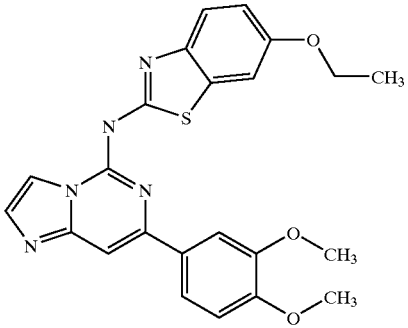 | 447.5195 | B | 448 | |
| 12-7 | 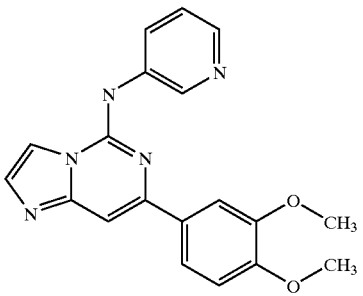 | 347.3796 | A | 348 | |
| 12-8 | 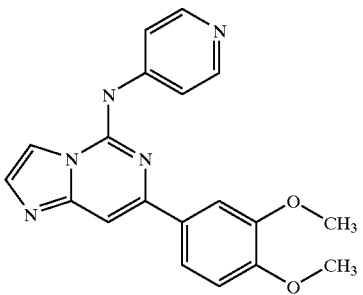 | 347.3796 | A | | (DMSO d-6) 3.83 (3H, s), 3.89 (3H, s), 7.08 (1H, d, J = 8.2 Hz), 7.65 (1H, s), 7.73–7.76 (3H, m), 7.97 (2H, d, J = 5.9 Hz), 8.29 (1H, s), 8.53 (2H, d, J = 5.9 Hz), 9.95 (1H, brs) |

TABLE 11-continued

| Ex. No. | MOLSTRUCTURE | MOLWEIGHT | Activity grade | MS | NMR |
|---|---|---|---|---|---|
| 12-9 | | 426.2757 | A | | (DMSO d-6) 3.82 (3H, s), 3.88 (3H, s), 7.06 (1H, s, J = 8.6 Hz), 7.57 (1H, s), 7.65 (1H, s), 7.68 (1H, s), 7.70 (1H, s), 8.09 (1H, d, J = 9.0 Hz), 8.35 (2H, m), 8.51 (1H, s), 10.64 (1H, brs) |
| 12-10 | | 332.365 | A | | (DMSO d-6) d 3.85 (3H, s), 7.07 (1H, d, J = 8.6 Hz), 7.27 (1H, m), 7.49–7.64 (5H, m), 7.81 (1H, s), 7.83 (1H, s), 8.06 (1H, d, J = 2.2 Hz), 8.49 (1H, d, J = 1.9 Hz), 9.30 (1H, broad s), 10.15 (1H, s). |
| 12-11 | | 380.8371 | A | | |
| 12-12 | | 425.2881 | A | 425 | |

TABLE 11-continued

| Ex. No. | MOLSTRUCTURE | MOLWEIGHT | Activity grade | MS | NMR |
|---|---|---|---|---|---|
| 12-13 | | 414.3905 | B | 415 | |
| 12-14 | | 436.4716 | A | | |
| 12-15 | | 377.4061 | A | | (CDCl3) d 3.95 (3H, s), 3.98 (3H, s), 6.97 (3H, d, J = 9Hz), 7.47(1H, s), 7.65 (1H, dd, J = 2 Hz, 8.4 Hz), 7.72 (1H, d, J = 2 Hz), 7.78 (2H, d, J = 9 Hz), 7.99 (1H, s), 8.29 (1H, s) |
| 12-16 | | 459.5471 | A | 460 | (CDCl3) d 2.05 (2H, quint, J = 6.8 Hz), 2.48 (4H, t, J = 4.4 Hz), 2.56 (2H, t, J = 7.1 Hz), 3.73 (4H, t, J = 4.6 Hz), 3.94 (3H, s), 4.16 (2H, t, J = 6.6 Hz), 6.76 (1H, s), 6.98 (1H, d, J = 8.4 Hz), 7.20 (1H, t, J = 7.4 Hz), 7.39–7.46 (3H, m), 7.51 (1H, s), |

TABLE 11-continued

| Ex. No. | MOLSTRUCTURE | MOLWEIGHT | Activity grade | MS | NMR |
|---|---|---|---|---|---|
| 12-17 | | 374.3982 | A | 375 | (CDCl3) d 2.37 (3H, s), 3.87 (3H, s), 6.93 (1H, s), 6.98 (1H, d, J = 8.7 Hz), 7.18 (1H, t, J = 7.4 Hz), 7.25–7.45 (4H, m), 7.61–7.71 (4H, m), 7.87 (1H, dd, J = 2.2, 8.6 Hz). |
| 12-18 | | 422.4858 | B | 423 | (DMSO d-6) d 3.94 (3H, s), 5.22 (2H, s), 6.85 (1H, s), 6.95 (1H, d, J = 8.3 Hz), 7.19 (1H, t, J = 7.4 Hz), 7.28–7.55 (8H, m), 7.65 (1H, d, J = 1.5 Hz), 7.72–7.76 (3H, m). |
| 12-19 | | 332.3614 | A | 333 | (DMSO d-6) d 3.86 (3H, s), 6.84 (1H, d, J = 8.3 Hz), 7.15 (1H, t, J = 7.3 Hz), 7.45 (2H, m), 7.55–7.60 (3H, m), 7.33 (1H, d, J = 1.9 Hz), 7.91 (1H, d, J = 7.7 Hz), 8.26 (1H, s), 9.25 (1H, s), 9.50 (1H, s). |
| 12-20 | | 404.4676 | A | 405 | (CDCl3) d 1.24 (3H, t, J = 7.0 Hz), 3.61 (H, q, J = 7.0 Hz), 3.85 (2H, t, J = 5.3 Hz), 4.24 (2H, t, J = 5.3 Hz), 6.68 (1H, s), 6.99 (1H, d, J = 8.4 Hz), 7.20 (1H, t, J = 7.5 Hz), 7.40–7.45 (3H, m), 7.52 (1H, s), 7.58 (1H, dd, J = 2.1, 8.4 Hz), 7.60–7.76 (4H, m). |
| 12-21 | | 344.3724 | B | 345 | (CDCl3) d 4.30 (3H, s), 6.93 (1H, d, J = 8.4 Hz), 7.04 (1H, broad s), 7.19 (1H, t, J = 7.4 Hz), 7.44 (3H, m), 7.52–7.64 (4H, m), 7.73 (2H, d, J = 7.8 Hz). |

TABLE 11-continued
| Ex. No. | MOLSTRUCTURE | MOLWEIGHT | Activity grade | MS | NMR |
|---|---|---|---|---|---|
| 12-22 | 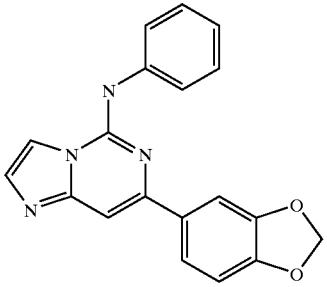 | 330.3456 | B | 331 | (CDCl3) d 6.00 (2H, s), 6.70(1H, broad s), 6.89 (1H, d, J = 8.2 Hz), 7.21 (1H, t, J = 7.4 Hz), 7.42–7.48 (4H, m), 7.52 (1H, d, J = 1.7 Hz), 7.58 (1H, dd, J = 1.7, 8.2 Hz), 7.66–7.71 (3H, m). |
| 12-23 | 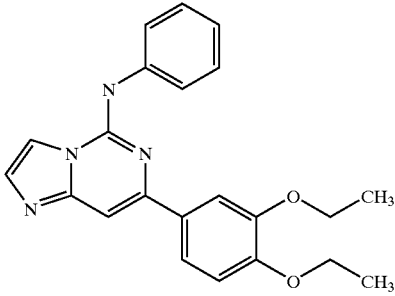 | 374.4418 | A | 375 | (CDCl3) d 1.47 (6H, t, J = 7.0 Hz), 1.49 (3H, t, J = 7.0 Hz), 4.17 (4H, m), 6.95 (1H, d, J = 8.4 Hz), 7.18 (1H, t, J = 7.4 Hz), 7.38–7.48 (4H, m), 7.55–7.71 (4H, m), 7.79 (2H, d, J = 8.0 Hz). |
| 12-24 | 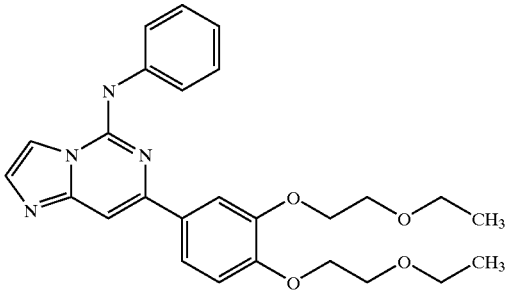 | 462.547 | B | 463 | (CDCl3) d 1.24 (6H, t, J = 7.0 Hz), 3.62 (4H, m), 3.84 (4H, q, J = 5.1 Hz), 4.23 (4H, m), 6.75 (1H, s), 6.99 (1H, d, J = 8.5 Hz), 7.19(1H, t, J = 7.4 Hz), 7.40–7.49 (4H, m), 7.60 (1H, dd, J = 2.1, 8.4 Hz), 7.65 (1H, d, J = 21.3 Hz), 7.72–7.75 (3H, m). |
| 12-25 | 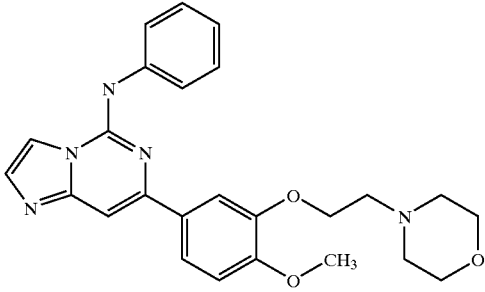 | 445.5203 | A | 446 | (CDCl3) d 2.59 (4H, t, J = 4.6 Hz), 2.87 (2H, t, J = 6.1 Hz), 3.73 (4H, t, J = 4.6 Hz), 3.90 (3H, s), 4.23 (2H, t, J = 6.1 Hz), 6.95 (1H, d, J = 8.5 Hz), 7.18 (2H, s), 7.39–7.76 (9H, m). |
| 12-26 | 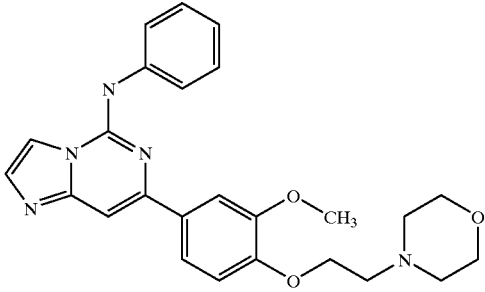 | 445.5203 | A | 446 | (CDCl3) d 2.61 (4H, t, J = 4.6 Hz), 2.87 (2H, t, J = 6.0 Hz), 3.74 (4H, t, J = 4.6 Hz), 3.93 (3H, s), 4.22 (2H, t, J = 6.0 Hz), 6.83 (1H, s), 6.97 (1H, d, J = 8.5 Hz), 7.19 (1H, t, J = 7.4 Hz), 7.39–7.76 (9H, m). |

TABLE 11-continued

| Ex. No. | MOLSTRUCTURE | MOLWEIGHT | Activity grade | MS | NMR |
|---|---|---|---|---|---|
| 12-27 | | 422.4858 | C | 423 | (CDCl3) d 3.94 (3H, s), 5.21 (2H, s), 6.72 (1H, broad s), 6.98 (1H, d, J = 8.6 Hz), 725–7.44 (10H, m), 7.64 (2H, m), 7.72 (3H, m). |
| 12-28 | | 404.4676 | A | 405 | (CDCl3) d 1.24 (3H, t, J = 7.0 Hz), 3.62 (2H, q, J = 7.0 Hz), 3.87 (2H, t, J = 5.3 Hz), 4.27 (2H, t, J = 5.3 Hz), 6.70 (1H, s), 6.95 (1H, d, J = 8.5 Hz), 7.20 (1H, t, J = 7.4 Hz), 7.32–7.50 (4H, m), 7.60–7.75 (5H, m) |
| 12-29 | | 362.3912 | A | 363 | |
| 12-30 | | 381.8214 | A | 382 | |
| 12-31 | | 354.393 | B | 355 | |

TABLE 11-continued

| Ex. No. | MOLSTRUCTURE | MOLWEIGHT | Activity grade | MS | NMR |
| --- | --- | --- | --- | --- | --- |
| 12-32 | | 361.3595 | A | | (d8-DMSO) 3.99 (3H, s), 7.12–7.22 (1H, m), 7.38–7.50 (3H, m), 7.65 (1H, s), 7.75 (1H, s), 7.85 (2H, d, J = 7.9 Hz), 8.31 (1H, s), 8.40 (1H, dd, J = 2.3, 8.7 Hz), 8.60 (1H, d, J = 2.3 Hz), 9.63 (1H, s) |
| 12-33 | | 374.3982 | A | | (CDCl3) d 2.41 (3H, s), 3.65 (3H, s), 6.84 (1H, d, J = 8.3 Hz), 7.12–7.21 (3H, m), 7.28–7.43 (4H, m), 7.60 (2H, m), 7.74 (2H, d, J = 7.7 Hz). |
| 12-34 | | 475.6141 | A | | (CDCl3) d 2.02 (2H, quint, J = 6.8 Hz), 2.57 (2H, t, J = 7.1 Hz), 2.67–2.75 (8H, m), 3.94 (3H, s), 4.14 (2H, t, J = 6.8 Hz), 6.70 (1H, s), 6.98 (1H, d, J = 8.3 Hz), 7.20 (1H, t, J = 7.1 Hz), 7.33–7.58 (9H, m). |
| 12-35 | | 431.5371 | C | | (CDCl3) d 0.96(6H, t, J = 7.2 Hz), 2.57 (4H, q, J = 7.2 Hz), 2.89 (2H, t, J = 5.8 Hz), 3.96 (3H, s), 4.25 (2H, t, J = 5.1 Hz), 6.98 (1H, d, J = 8.6 Hz), 7.16–7.60 (6H, m), 7.77 (1H, d, J = 1.9 Hz), 8.05 (2H, d, J = 7.6 Hz), 9.96 (1H, s). |

TABLE 11-continued
| Ex. No. | MOLSTRUCTURE | MOLWEIGHT | Activity grade | MS | NMR |
|---|---|---|---|---|---|
| 12-36 | 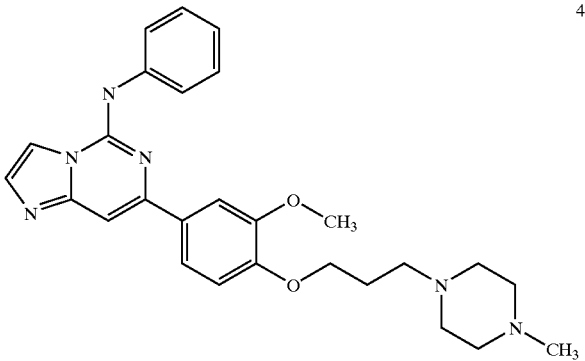 | 472.5898 | A | | (CDCl3) d 2.05 (2H, quint, J = 6.8 Hz), 2.29 (3H, s), 2.31–2.58 (10H, m), 3.94 (3H, s), 4.15 (2H, t, J = 6.8 Hz), 6.74 (1H, s), 6.98 (1H, d, J = 8.6 Hz), 7.20 (1H, t, J = 7.1 Hz), 7.40–7.76 (9H, m). |
| 12-37 | 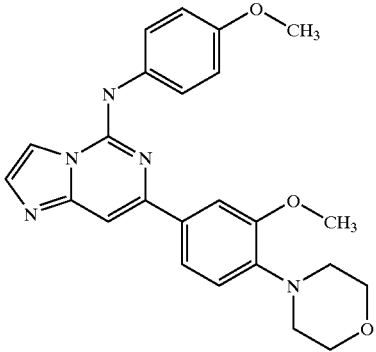 | 431.4935 | A | | CDCl3 7.64–7.61 (m, 4H), 7.57 (dd, 1H, J = 13.8, 3.2 Hz), 7.47 (s, 1H), 7.00 (s, 1H), 6.91 (d, 1H, J = 15.1 Hz), 3.92 (s, 3H), 3.91 (t, 4H, J = 8.2 Hz), 3.84 (s, 3H), 3.13 (t, 4H, J = 7.6 Hz) |
| 12-38 | 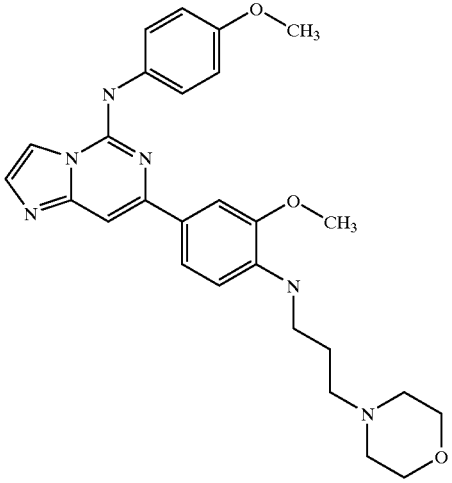 | 488.5888 | A | | CDCl3 7.67 (d, 2H, J = 9.1 Hz), 7.62 (s, 1H), 7.56 (s, 1H), 7.54 (s, 2H), 7.38 (s, 1H), 6.93 (d, 2H, J = 9.1 Hz), 6.60 (d, 1H, J = 8.6 Hz), 3.91 (s, 3H), 3.83 (s, 3H), 3.76 (m, 4H), 3.27 (t, 2H, J = 6.4 Hz), 2.51 (m, 4H), 1.86 (t, 2H, J = 6.4 Hz) |

TABLE 11-continued

| Ex. No. | MOLSTRUCTURE | MOLWEIGHT | Activity grade | MS | NMR |
|---|---|---|---|---|---|
| 12-39 | | 471.6057 | A | | CDCl3 7.77 (d, 2H, J = 7.5 Hz), 7.58 (s, 3H), 7.52 (s, 1H), 7.41 (d, 2H, J = 7.9 Hz), 7.37 (s, 1H), 7.16 (t, 1H, J = 7.9 Hz), 6.62 (d, 2H, J = 8.7 Hz), 3.92 (s, 3H), 3.26 (d, 2H, J = 6.2 Hz), 2.55 (m, 10H), 2.32 (s, 3H), 1.85 (1, 2H, J = 6.4 Hz) |
| 12-40 | | 456.5472 | A | | MeOD-d4 8.08 (s, 1H), 7.86 (d, 2H, J = 7.6 Hz), 7.68–7.26 (m, 8H), 7.19 (d, 1H, J = 7.7 Hz), 3.93 (s, 3H), 3.49–3.22 (m, 6H), 2.42 (t, 2H, J = 8.1 Hz), 1.88 (m, 2H) |
| 12-41 | | 403.4835 | A | | (CDCl3), 2.94 (3H, s), 3.34 (3H, s), 3.38 (2H, t, J = 6.0 Hz), 3.58 (2H, t, J = 6.0 Hz), 3.94 (3H, s), 6.77 (1H, s), 7.00 (1H, d, J = 8.5 Hz), 7.19 (1H, t, J = 7.6 Hz), 7.43 (1H, t, J = 7.6 Hz), 7.46 (1H, s), 7.52 (1H, s), 7.58 (1H, dd, J = 1.9 Hz, J = 8.2 Hz), 7.67 (1H, dd, J = 1.9 Hz, J = 8.2 Hz), 7.76 (2H, d, J = 7.6 Hz) |
| 12-42 | | 417.5103 | A | | (CDCl3), 2.38 (3H, s), 2.95 (3H, s), 3.34 (3H, s), 3.39 (2H, t, J = 6.0 Hz), 3.57 (2H, t, J = 6.0 Hz), 3.96 (3H, s), 6.85 (1H, s), 7.00 (1H, d, J = 8.2 Hz), 7.21 (2H, d, J = 8.2 Hz), 7.48 (2H, d, J = 11.0 Hz), 7.57 (1H, dd, J = 2.2 Hz, J = 8.5 Hz), 7.64 (2H, d, J = 8.5 Hz), 7.65 (2H, d, J = 1.9 Hz) |

TABLE 11-continued

| Ex. No. | MOLSTRUCTURE | MOLWEIGHT | Activity grade | MS | NMR |
|---|---|---|---|---|---|
| 12-43 | | 471.4806 | A | | (CDCl3), 2.95 (3H, s), 3.35 (3H, s), 3.39 (2H, t, J = 6.0 Hz), 3.59 (2H, t, J = 6.0 Hz), 3.95 (3H, s), 7.02 (2H, d, J = 8.5 Hz), 7.04 (1H, s), 7.53 (1H, s), 7.56 (1H, s), 7.60 (1H, s), 7.68 (1H, d, J = 3.7 Hz), 7.69 (1H, d, J = 3.5 Hz), 7.93 (2H, d, J = 8.5 Hz) |
| 12-44 | | 481.5743 | A | | (CDCl3), 2.94 (3H, s), 3.06 (3H, s), 3.35 (3H, s), 3.40 (2H, t, J = 5.9 Hz), 3.60 (2H, t, J = 6.3 Hz), 3.97 (3H, s), 7.03 (1H, d, J = 8.2 Hz), 7.29 (1H, t, J = 7.3 Hz), 7.58 (2H, d, J = 8.8 Hz), 7.62 (1H, s), 7.68 (1H, s), 7.74 (1H, td, J = 1.6 Hz, J = 7.3 Hz), 8.01 (1H, dd, J = 1.3 Hz, J = 7.9 Hz), 9.11 (1H, d, J = 8.2 Hz), 9.85 (1H, s) |
| 12-45 | | 390.4012 | A | | (DMSO d-6) 3.82 (3H, s), 3.88 (3H, s), 7.07 (1H, s), 7.70–7.79 (6H, m), 8.18 (1H, s), 8.47 (1H, s), 8.65 (1H, s), 10.04 (1H, s), 11.97 (1H, s) |
| 12-46 | | 482.3796 | A | | (CDCl3), 2.95 (3H, s), 3.35 (3H, s), 3.40 (2H, t, J = 6.0 Hz), 3.59 (2H, t, J = 5.9 Hz), 3.95 (3H, s), 7.01 (1H, d, J = 8.2 Hz), 7.20 (1H, s), 7.50 (1H, s), 7.52 (2H, d, J = 6.9 Hz), 7.54 (1H, d, J = 1.9 Hz), 7.56 (1H, s), 7.59 (1H, d, J = 1.9 Hz), 7.64 (1H, d, J = 1.0 Hz), 7.71 (2H, d, J = 6.9 Hz) |

TABLE 11-continued

| Ex. No. | MOLSTRUCTURE | MOLWEIGHT | Activity grade | MS | NMR |
|---|---|---|---|---|---|
| 12-47 | | 415.4945 | A | | (MeOD) 2.36 (3H, s), 3.09 (4H, t, J = 4.3 Hz), 3.84 (4H, t, J = 4.3 Hz), 3.91 (3H, s), 7.00 (1H, d, J = 8.3 Hz), 7.23 (2H, AB, J = 8.3 Hz), 7.40 (1H, s), 7.55 (1H, s), 7.62 (1H, dd, J = 1.5, 8.3 Hz), 7.74 (2H, AB, J = 8.3 Hz), 7.76 (1H, s), 8.05 (1H, s) |
| 12-48 | | 436.9009 | A | | (CDCl3) 3.17 (4H, t, J = 4.5 Hz), 3.93 (4H, t, J = 4.5 Hz), 4.00 (3H, s), 6.91 (1H, s), 7.06 (1H, d, J = 8.5 Hz), 7.23 (2H, m), 7.36 (1H, dd, J = 1.9, 8.5 Hz), 7.48 (1H, d, J = 1.5 Hz), 7.66 (1H, dd, J = 2.6, 8.5 Hz), 7.96 (1H, s), 8.27 (1H, d, J = 2.6 Hz) |
| 12-49 | | 469.4648 | A | | (MeOD) 3.11 (4H, t, J = 4.5 Hz), 3.85 (4H, t, J = 4.5 Hz), 3.93 (3H, s), 7.03 (1H, d, J = 8.3 Hz), 7.49 (1H, s), 7.60 (1H, d, J = 1.5 Hz), 7.65 (1H, dd, J = 1.9, 8.3 Hz), 7.69 (1H, s), 7.73 (2H, AB, J = 4.5 Hz), 8.10 (3H, m) |
| 12-50 | | 372.4906 | A | | CDCl3 7.65 (s, 1H), 7.63 (s, 2H), 7.63 (s, 2H), 7.47 (s, 1H), 7.26 (m, 1H), 7.02 (d, 1H, J = 8.9 Hz), 3.96 (s, 3H), 3.59 (t, 1H, J = 6.0 Hz), 3.51 (q, 2H, J = 7.3 Hz), 3.40 (t, 2H, J = 6.2 Hz), 3.35 (s, 3H), 2.95 (s, 1.59 (t, 3H, J = 7.3 Hz) |

TABLE 11-continued

| Ex. No. | MOLSTRUCTURE | MOLWEIGHT | Activity grade | MS | NMR |
|---|---|---|---|---|---|
| 12-51 | | 433.5093 | A | | CDCl3 7.64 (d, 2H, J = 9.3 Hz), 7.62 (s, 2H), 7.63 (s, 1H), 7.59 (s, 1H), 7.52 (s, 1H), 7.43 (s, 1H), 6.97 (d, 1H, J = 8.2 Hz), 6.94 (d, 2H, J = 9.3 Hz), 3.90 (s, 3H), 3.83 (s, 3H), 3.57 (1, 2H, J = 6.0 Hz), 3.36 (q, 2H, J = 6.0 Hz), 3.34 (s, 3H), 2.92 (s, 3H) |
| 12-52 | | 389.4567 | A | | CDCl3 7.72 (s, 1H), 7.68 (d, 2H, J = 8.8 Hz), 7.63 (s, 1H), 7.58 (s, 1H), 7.54 (d, 1H, J = 8.5 Hz), 7.43 (s, 1H), 6.96 (d, 1H, J = 8.5 Hz), 6.93 (d, 2H, J = 8.9 Hz), 3.98 (s, 3H), 3.83 (s, 3H), 2.89 (s, 6H) |
| 12-53 | | 480.3638 | A | | CDCl3 7.94 (br s, 1H), 7.77 (s, 2H), 7.74 (s, 1H), 7.62 (s, 2H), 7.59 (d, 1H, J = 13.8 Hz), 7.52 s), 7.48 (s, 2H), 6.97 (d, 1H, J = 13.8 Hz), 3.95 (s, 3H), 3.91 (t, 4H, J = 7.6 Hz), 3.14 (t, 4H, J = 7.6 Hz) |
| 12-54 | | 401.4677 | A | | CDCl3 7.80 (d, 2H, J = 7.9 Hz), 7.69 (s, 1H), 7.67 (s, 1H), 7.63 (s, 1H), 7.59 (dd, 1H, J = 8.2, 1.9 Hz), 7.50 s), 7.40 (t, 2H, J = 8.1 Hz), 7.18 (t, 1H, J = 7.4 Hz), 6.97 (d, 1H, J = 8.2 Hz), 3.94 (s, 3H), 3.91 (t, 4H, J = 4.6 Hz), 3.14 (t, 4H, J = 4.5 Hz) |

TABLE 11-continued

| Ex. No. | MOLSTRUCTURE | MOLWEIGHT | Activity grade | MS | NMR |
|---|---|---|---|---|---|
| 12-55 | | 502.6156 | A | | CDCl3 7.74–7.52 (m, 6H), 7.44 (s, 1H), 7.20 (brs, 1H), 6.93 (d, 3H, J = 15.0 Hz), 3.90 (s, 3H), 3.83 (s, 3H), 3.70 (t, 4H, J = 7.7 Hz), 3.18 (t, 2H, J = 12.6 Hz), 2.83 (s, 3H), 2.43–2.33 (m, 6H) |
| 12-56 | | 447.5361 | A | | CDCl3 7.65 (d, 2H, J = 8.9 Hz), 7.61 (s, 1H), 7.58 (d, 1H, J = 6.0 Hz), 7.52 (d, 1H, J = 8.2 Hz), 7.43 (s, 1H), 6.98–6.92 (m, 3H), 3.95 (m, 4H), 3.83 (s, 3H), 3.41 (t, 2H, J = 6.3 Hz), 3.31 (s, 3H), 3.22 (t, 2H, J = 7.6 Hz), 2.84 (s, 3H), 1.84 (m, 2H) |
| 12-57 | | 479.562 | A | | CDCl3 9.87 (s, 1H), 9.10 (d, 1H, J = 8.5 Hz), 8.01 (d, 1H, J = 7.9 Hz), 7.26 (t, 1H, J = 8.5 Hz), 7.69 (s, 1H), 7.64–7.59 (m, 4H), 7.30 (t, 1H, J = 6.9 Hz), 7.02 (d, 1H, J = 7.9 Hz), 3.99 (s, 3H), 3.92 (t, 4H, J = 4.1 Hz), 3.17 (s, 7H) |

TABLE 11-continued

| Ex. No. | MOLSTRUCTURE | MOLWEIGHT | Activity grade | MS | NMR |
|---|---|---|---|---|---|
| 12-58 | | 417.4715 | | 418 | DMSO 10.44 (s, 1H), 8.74 (d, 1H, J = 2.2 Hz), 8.09 (d, 1H, J = 2.2 Hz), 7.70 (m, 2H, ), 7.69 (s, 1H), 7.64–7.59 (m, 3H), 7.010 (d, 1H, J = 8.9 Hz), 6.88 (d, 1H, J = 8.8 Hz), 3.87 (s, 3H), 3.75 (f, 4H, J = 4.1 Hz), 3.09 (t, 4H, J = 4.2 Hz) |
| 12-59 | | 441.4927 | A | 442 | (MeOD) 3.14 (4H, t, J = 4.4 Hz), 3.87 (4H, t, J = 4.4 Hz), 4.01 (3H, s), 6.85 (1H, dd, J = 1.9, 8.5 Hz), 7.10 (1H, d, J = 8.5 Hz), 761 (1H, d, J = 8.5 Hz), 7.65 (1H, d, J = 1.3 Hz), 7.78 (1H, dd, J = 1.9, 8.5 Hz), 7.80 (1H, s), 7.85 (1H, s), 7.88 (1H, d, J = 1.9 Hz), 8.22 (1H, s), 8.91 (1H, s) |
| 12-60 | | 479.5585 | A | 480 | (MeOD) 3.09 (4H, t, J = 4.7 Hz), 3.16 (3H, s), 3.85 (4H, t, J = 4.7 Hz), 3.94 (3H, s), 7.02 (1H, d, J = 8.5 Hz), 7.49 (1H, d, J = 0.6 Hz), 7.60 (1H, d, J = 1.6 Hz), 7.67 (2H, m), 7.72 (2H, m), 8.12 (1H, d, J = 0.6 Hz), 8.16 (1H, m), 8.72 (1H, t, J = 1.9 Hz) |
| 12-61 | | 390.4049 | B | 391 | |

Example 13

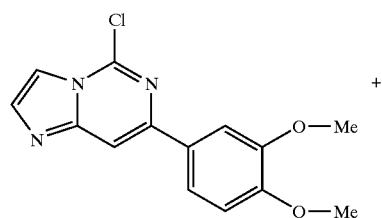

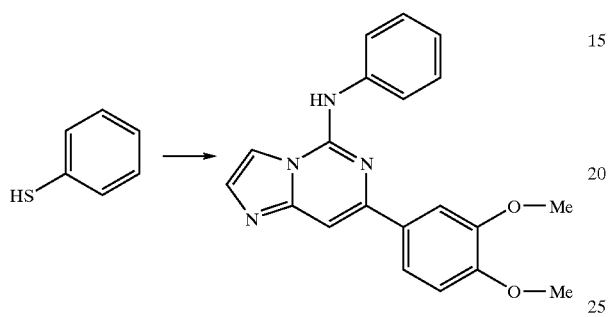

A solution of 5-chloro-7-(3,4-dimethoxyphenyl)-imidazo[1,2-c]pyrimidine 0.26 mmol and thiophenol 0.52 mmol in DMSO was stirred overnight at room temperature. The reaction mixture was neutralized with sat. NaHCO$_3$ solution and diluted with water and extracted with CHCl$_3$. The organic extracts were washed with brine, and dried over Na$_2$SO$_4$. The resulting product, 5-phenylsulfenyl-7-(3,4-dimethoxyphenyl)imidazo[1,2-c]pyrimidine, was concentrated and purified by column chromatography.

Molecular weight 363.4414 Mass spectrometry: 364
Activity grade: A

With the use of any of the intermediates I or II and according to the procedure that is similar to that of Example 13, following compounds shown in Table 12 below were prepared.

TABLE 12

| Ex. No. | MOLSTRUCTURE | MOLWEIGHT | Activity grade | MS | NMR |
|---|---|---|---|---|---|
| 13-1 | | 391.4956 | B | | |
| 13-2 | | 393.4679 | A | | |

TABLE 12-continued

| Ex. No. | MOLSTRUCTURE | MOLWEIGHT | Activity grade | MS | NMR |
|---|---|---|---|---|---|
| 13-3 | | 378.4561 | A | | |
| 13-4 | | 378.4561 | A | | |
| 13-5 | | 432.3315 | C | | |
| 13-6 | | 442.3374 | A | | |

TABLE 12-continued

| Ex. No. | MOLSTRUCTURE | MOLWEIGHT | Activity grade | MS | NMR |
|---|---|---|---|---|---|
| 13-7 | | 393.4679 | A | | |
| 13-8 | | 453.5209 | A | 454 | (DMSO-d6) 3.63 (s, 3H), 3.76 (s, 3H), 3.77 (s, 3H), 3.80 (s, 3H), 6.95 (d, 1H, J = 8.53 Hz), 7.14 (s, 2H), 7.41 (d, 2H, J = 1.99 Hz), 7.57 (dd, 1H), 7.75 (d, 1H, J = 1.40 Hz), 7.97 (d, 2H, J = 8.02 Hz). |
| 13-9 | | 391.4956 | C | | (CDCl3) 2.48 (s, 6H), 3.65 (s, 3H), 3.88 (s, 3H), 6.84 (d, 1H, J = 8.464 Hz), 7.21–7.37 (m, 5H), 7.65–7.71 (m, 3H). |
| 13-10 | | 432.3315 | B | | (CDCl3) 3.73 (s, 3H), 3.89 (s, 3H), 6.85 (d, 1H, J = 8.45 Hz), 7.24 (d, 1H, J = 2.09 Hz), 7.32–7.35 (m, 1H), 7.38–7.44 (m, 1H), 7.54–7.57 (m, 2H), 7.65–7.67 (m, 2H), 7.72 (d, 1H, J = 1.43 Hz). |

TABLE 12-continued

| Ex. No. | MOLSTRUCTURE | MOLWEIGHT | Activity grade | MS | NMR |
|---|---|---|---|---|---|
| 13-11 | | 420.5153 | A | 421 | (CDCl3) 3.60 (3H, s), 3.92 (3H, s), 6.92 (1H, d, J = 8.2 Hz), 7.45–7.58 (4H, m), 7.64 (1H, s), 7.76 (2H, d, J = 12.6 Hz), 7.89 (1H, d, J = 7.3 hz), 8.12 (2H, d, J = 7.3 Hz). |
| 13-12 | | 367.4325 | A | 368 | (CDCl3) 3.78 (3H, s), 3.85 (3H, s), 3.91 (3H, s), 6.88 (1H, d, J = 8.5 Hz), 7.25 (1H, s), 7.35 (1H, d, J = 8.5 Hz), 7.61 (1H, s), 7.68 (1H, s), 7.71 (1H, s). |
| 13-13 | | 365.4166 | A | 366 | (CDCl3) 3.94 (3H, s), 3.98 (3H, s), 6.97 (1H, d, J = 8.9 Hz), 7.10 (1H, t, J = 4.9 Hz), 7.58 (1H, s), 7.62–7.66 (2H, m), 7.96 (1H, s), 8.50 (1H, d, J = 4.9 Hz). |
| 13-14 | | 418.5214 | A | 419 | (DMSO) 2.58 (1H, bs), 2.75 (2H, t, J = 5.3 Hz), 2.98 (2H, t, J = 5.3 Hz), 3.61 (3H, s), 3.78 (3H, s), 3.89 (2H, s), 6.95 (1H, d, J = 8.5 Hz), 7.29 (1H, d, J = 7.9 Hz), 7.34 (1H, s), 7.45 (1H, s), 7.51 (1H, d, J = 7.9 Hz), 7.56 (1H, d, J = 8.5 Hz), 7.96 (2H, d, J = 6.3 Hz). |

TABLE 12-continued

| Ex. No. | MOLSTRUCTURE | MOLWEIGHT | Activity grade | MS | NMR |
|---|---|---|---|---|---|
| 13-15 | | 363.4414 | | 364 | (DMSO-d6) 3.78 (3H, s), 3.87 (3H, s), 7.16 (1H, d, J = 8.4 Hz), 7.32–7.40 (5H, m), 7.75 (1H, d, J = 1.4 Hz), 7.89–7.92 (2H, m), 7.99–8.03 (2H, m) |
| 13-16 | | 461.5902 | A | | (CDCl3) 2.37 (3H, s), 2.58 (4H, t, J = 5.1 Hz), 3.31 (4H, t, J = 5.0 Hz), 3.70 (3H, s), 3.89 (3H, s), 6.85 (1H, d, J = 8.5 Hz), 6.98 (2H, d, J = 8.9 Hz), 7.35–7.42 (2H, m), 7.55–7.67 (5H, m) |
| 13-17 | | 303.3884 | | 304 | (DMSO-d6) 7.35–7.37 (3H, m), 7.59–7.65 (3H, m), 7.79–7.85 (5H, m), 8.06 (2H, s) |
| 13-18 | | 333.4149 | | 334 | (DMSO-d6) 3.77 (3H, s), 6.89 (2H, d, J = 8.9 Hz), 7.58–7.64 (3H, m), 7.74–7.80 (5H, m), 7.95 (2H, d, J = 12.3) |

TABLE 12-continued

| Ex. No. | MOLSTRUCTURE | MOLWEIGHT | Activity grade | MS | NMR |
|---|---|---|---|---|---|
| 13-19 | | 421.4751 | C–D | | (DMSO-d6) d 3.51 (3H, s), 3.54 (2H, s), 3.73 (3H, s), 6.82 (1H, s), 6.89 (2H, s), 7.12–7.23 (4H, m), 7.55 (1H, d, J = 1 Hz), 8.19 (1H, d, J = 1 Hz), 12.28 (1H, s) |
| 13-20 | | 421.4784 | A | 422 | |
| 13-21 | | 449.5287 | C | | (DMSO-d6) d 1.72–1.86 (2H, m), 2.14–2.27 (2H, m), 2.56–2.62 (2H, m), 3.53 (3H, s), 3.73 (3H, s), 6.82–6.90 (3H, m), 7.11 (2H, d, J = 8 Hz), 7.18 (2H, d, J = 8 Hz), 7.55 (1H, s), 8.19 (1H, s), 12.01 (1H, s), 13.43 (1H, s) |
| 13-22 | | 447.5167 | A | 448 | |

TABLE 12-continued

| Ex. No. | MOLSTRUCTURE | MOLWEIGHT | Activity grade | MS | NMR |
|---|---|---|---|---|---|
| 13-23 | | 475.5709 | B | 476 | (CDCl3) 1.83 (1H, m), 2.22–2.27 (1H, m), 2.70–2.99 (3H, m), 3.07 (2H, d, J = 7.7 Hz), 3.74 (3H, s), 3.75 (3H, s), 3.90 (3H, s), 6.87 (1H, d, J = 8.4 Hz), 7.34 (1H, s, J = 2.0 Hz), 7.36–7.51 (3H, m), 7.60 (1H, s), 7.67 (1H, s), 7.68 (1H, s). |
| 13-24 | | 421.4751 | A | 422 | (DMSO d-6) d 2.64 (2H, t, J = 7.5 Hz), 2.96 (2H, t, J = 7.5 Hz), 3.80 (3H, s), 6.91 (1H, d, J = 8.5 Hz), 7.24 (1H, dd, J = 2.2, 8.5 Hz), 7.29 (1H, d, J = 2.2 Hz), 7.47 (2H, d, J = 8.2 Hz), 7.67 (1H, d, J = 8.2 Hz), 7.83 (1H, s), 7.89 (1H, d, J = 1.6 Hz), |
| 13-25 | | 463.5119 | A | 464 | (CDCl3) d 2.36 (3H, s), 2.82 (2H, t, J = 7.0 Hz), 3.10 (2H, t, J = 7.0 Hz), 3.80 (3H, s), 6.72 (1H, d, J = 8.6 Hz), 722–7.28 (3H, m), 7.45 (3H, m), 7.62 (3H, m). |
| 13-26 | | 511.5995 | A | 512 | (CDCl3) d 2.76 (2H, t, J = 7.5 Hz), 3.06 (2H, t, J = 7.5 Hz), 3.78 (3H, s), 5.16 (2H, s), 6.83 (1H, d, J = 8.5 Hz), 6.90–7.45 (9H, m), 7.53 (2H, d, J = 2.0 Hz), 7.64–7.68 (3H, m). |

TABLE 12-continued
| Ex. No. | MOLSTRUCTURE | MOLWEIGHT | Activity grade | MS | NMR |
|---|---|---|---|---|---|
| 13-27 | | 421.4751 | A | 422 | (CDCl3) d 2.77 (2H, t, J = 7.5 Hz), 3.06 (2H, t, J = 7.5 Hz), 3.78 (3H, s), 6.86 (1H, d, J = 8.0 Hz), 7.15–7.32 (3H, m), 7.39 (2H, d, J = 8.2 Hz), 7.53 (2H, d), 7.68 (3H, m). |
| 13-28 | | 534.634 | A | | (DMSO d-6) d 2.62 (2H, t, J = 7.5 Hz), 2.92 (2H, t, J = 7.5 Hz), 3.15–3.55 (6H, m), 3.68 (3H, s), 3.77 (2H, broad 1), 3.97 (2H, broad t), 4.41 (2H, t, J = 4.7 Hz), 7.06 (1H, d, J = 8.5 Hz), 7.41 (1H, d, J = 1.9 Hz), 7.47 (2H, d, J = 8.2 Hz), 7.54 (1H, dd, |
| 13-29 | | 354.393 | A | | (DMSO) 3.74 (3H, s), 3.79 (3H, s), 6.97 (1H, d, J = 8.5 Hz), 7.06 (1H, d, J = 8.2 Hz), 7.36 (1H, d, J = 1.9 Hz), 7.40 (1H, s), 7.41–7.44 (1H, m), 7.51 (1H, d, J = 1.9 Hz), 7.80 (1H, s), 8.06 (1H, s). |
Example 14
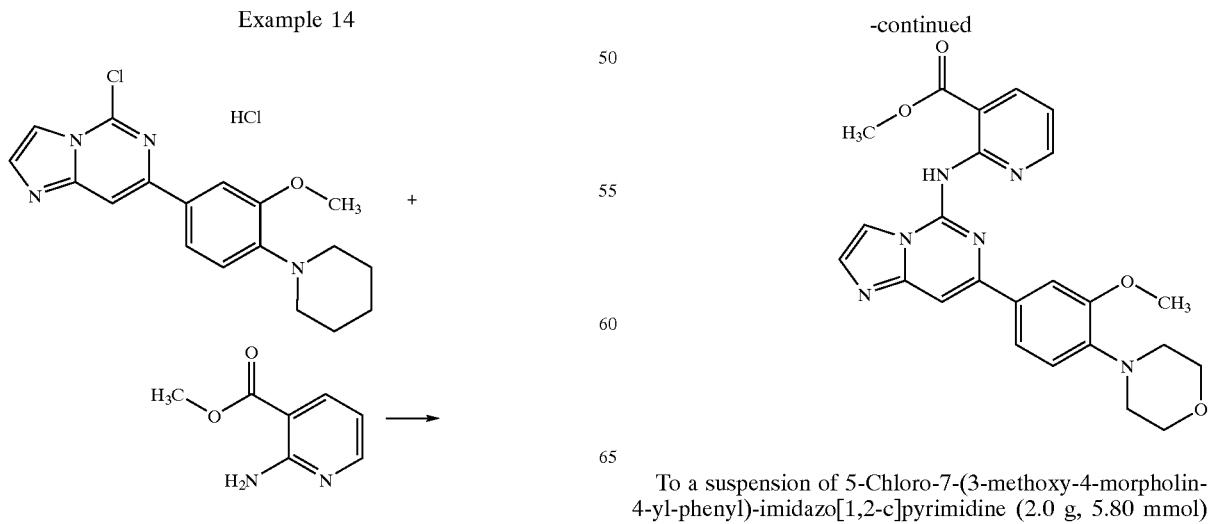
To a suspension of 5-Chloro-7-(3-methoxy-4-morpholin-4-yl-phenyl)-imidazo[1,2-c]pyrimidine (2.0 g, 5.80 mmol)

in DMF was added NaH (60% in mineral oil, 197 mg, 4.93 mmol) at 0° C. under an Ar atmosphere. After 10 min, 2-aminonicitinic methyl ester (1.06 g, 6.96 mmol) was added, followed by another portion of NaH (60% in mineral oil, 197 mg, 4.93 mmol). Then the reaction mixture was stirred at room temperature overnight. After quenching with 0.3 ml of acetic acid, the reaction mixture was poured into water. The organic layer was extracted with $CH_2Cl_2$ and the combined organic layer was dried over $MgSO_4$. After concentration in vacuo, the mixture containing 2-[7-(3-Methoxy-4-morpholin-4-yl-phenyl)-imidazo[1,2-c]pyrimidin-5-ylamino]-nicotinic acid methyl ester was used for the next step without further purification.

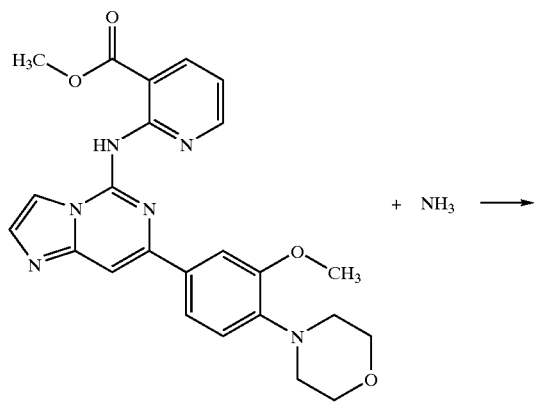

The mixture of the above methyl ester in saturated ammonia in EtOH (20 mL) was stirred for 3 days. The incoming solid was collected by filtration and eluted with MeOH. Vacuum oven dry gave 2-[7-(3-Methoxy-4-morpholin-4-yl-phenyl)-imidazo[1,2-c]pyrimidin-5-ylamino]-nicotinamide as a pale yellow solid (780 mg, 40%).

Activity grade: A

With the use of any of the intermediates I or II and according to the procedure that is similar to that of Example 14, following compounds shown in Table 13 below were prepared.

TABLE 13

| Ex. No. | MOLSTRUCTURE | MOLWEIGHT | Activity grade | MS | NMR |
|---|---|---|---|---|---|
| 14-1 | | 407.495 | B | | (DMSO) 3.72 (3H, s), 3.83 (3H, s), 3.86 (3H, s), 4.80 (2H, s), 6.89 (2H, d, 8.6 Hz), 7.09 (1H, d, J = 8.4 Hz), 7.47 (2H, d, J = 8.6 Hz), 7.69 (1H, s), 7.81 (1H, s), 7.84 (1H, dd, J = 2.0 Hz, 8.4 Hz), 8.01 (1H, s). |

TABLE 13-continued

| Ex. No. | MOLSTRUCTURE | MOLWEIGHT | Activity grade | MS | NMR |
|---|---|---|---|---|---|
| 14-2 | | 377.4685 | A | | (DMSO) 3.83 (3H, s), 3.84 (3H, s), 4.85 (2H, s), 7.08 (1H, d, J = 8.5 Hz), 7.28–7.37 (3H, m), 7.56 (2H, d, J = 8.4 Hz), 7.71 (1H, s), 7.78 (1H, s), 7.78–7.86 (2H, m), 8.01 (1H, s). |
| 14-3 | | 361.4039 | B | | |
| 14-4 | | 426.2728 | B | | |
| 14-5 | | 426.2728 | B | | |

TABLE 13-continued

| Ex. No. | MOLSTRUCTURE | MOLWEIGHT | Activity grade | MS | NMR |
| --- | --- | --- | --- | --- | --- |
| 14-6 | | 426.2728 | B | | |
| 14-7 | | 304.376 | C | 305 | (CDCl3) 7.30–7.40 (3H, m), 7.70–7.60 (4H, m), 7.65–7.81 (5h, m), 8.43 (1H, s) |
| 14-8 | | 320.3754 | C | 321 | (DMSO d-6) 6.98 (2H, d, J = 8.6 Hz), 7.36–7.43 (3H, m), 7.58 (2H, d, J = 8.6 Hz), 7.90–7.93 (2H, m), 8.23 (1h, s), 8.70 (1H, s) |
| 14-9 | | 339.8086 | C–D | 340 | |

TABLE 13-continued

| Ex. No. | MOLSTRUCTURE | MOLWEIGHT | Activity grade | MS | NMR |
|---|---|---|---|---|---|
| 14-10 | | 434.4771 | A | 435 | (DMSO d-6) 3.53 (3H, s), 3.78 (3H, s), 6.6.70 (1H, d, J = 16.0 Hz), 6.97 (1H, d, J = 8.6 Hz), 7.31 (1H, d, J = 2.0 Hz), 7.60–7.95 (6H, m), 8.32 (1H, s), 8.68 (1H, s), 12.53 (1H, br) |
| 14-11 | | 437.4807 | A | 438 | (CDCl3) 3.63 (3H, s), 3.79 (3H, s), 3.89 (2H, s), 6.74 (2H, d, J = 8.7 Hz), 6.98 (1H, d, J = 8.5 Hz), 8.16 (1H, s), 8.64 (1H, s), 12.66 (1H, br) |
| 14-12 | | 420.4285 | B | 421 | (DMSO d-6) 2.59 (2H, t, J = 7.5 Hz), 2.91 (2H, t, J = 7.5 Hz), 3.83 (3H, s), 3.88 (3H, s), 7.00 (1H, d, J = 8.5 Hz), 7.09 (1H, d, J = 8.3 Hz), 7.14 (1H, s), 7.47–7.59 (m), 8.40 (1H, s), 8.63 (1H, s), 12.13 (1H, br) |

TABLE 13-continued

| Ex. No. | MOLSTRUCTURE | MOLWEIGHT | Activity grade | MS | NMR |
|---|---|---|---|---|---|
| 14-13 | | 445.4669 | C | 446 | (DMSO) 3.82 (3H, s), 3.83, (3H, s), 4.94 (2H, s), 7.06 (1H, d, J = 8.5 Hz), 7.54–7.65 (2H, m), 7.70 (1H, s), 7.75 (1H, d, J = 2.1 Hz), 7.81 (1H, dd, J = 2.1 Hz, 8.5 Hz), 7.85 (2H, m), 7.96 (1H, s), 8.01 (1H, s). |
| 14-14 | | 387.4609 | B | 388 | (DMSO) 1.06 (3H, t, d = 7.1 Hz), 1.75 (3H, d, J = 7.3 Hz), 3.83 (3H, s), 3.91 (3H, s), 4.05–4.15 (2H, m), 4.84 (1H, q, J = 7.3 Hz), 7.06 (1H, d, J = 8.2 Hz), 7.71 (1H, d, J = 1.5 Hz), 7.76–7.79 (2H, m), 7.86 (1H, s), 8.02 (1H, s). |
| 14-15 | | 411.9135 | B | 412 | (DMSO) 3.83 (3H, s), 3.84 (3H, s), 4.85 (2H, s), 7.41 (2H, d, J = 8.4 Hz), 7.58 (2H, d, J = 8.4 Hz), 7.75 (2H, s), 7.81–7.88 (2H, m), 8.03 (1H, s). |

TABLE 13-continued

| Ex. No. | MOLSTRUCTURE | MOLWEIGHT | Activity grade | MS | NMR |
|---|---|---|---|---|---|
| 14-16 | | 369.3681 | A | 370 | (DMSO) 3.83 (3H, s), 3.88 (3H, s), 4.67 (2H, q, J = 10.2 Hz), 7.09 (1H, d, J = 8.2 Hz), 7.76–7.82 (3H, m), 7.98 (1H, s), 8.08 (1H, s). |
| 14-17 | | 329.4239 | A | 330 | (DMSO) 1.08 (3H, t, J = 7.3 Hz), 1.91 (2H, h, J = 7.3 Hz), 3.50 (2H, t, J = 7.3 Hz), 3.83 (3H, s), 3.88 (3H, s), 7.09 (1H, d, 8.3 Hz), 7.69 (1H, d, J = 1.4 Hz), 7.78–7.81 (3H, m), 7.99 (1H, s). |
| 14-18 | | 371.5052 | C–D | 372 | (DMSO) 0.86 (3H, t, J = 6.9 Hz), 1.25–1.35 (4H, m), 1.44–1.52 (2H, m), 1.86 (2H, p, J = 7.3 Hz), 3.52 (2H, t, J = 7.3 Hz), 3.83 (3H, s), 3.88 (3H, s), 7.07 (1H, d, J = 8.3 Hz), 7.69 (1H, d, J = 1.5 Hz), 7.77–7.82 (3H, m), 7.98 (1H, s). |
| 14-19 | | 414.574 | B | 415 | (DMSO) 0.98 (12H, d, J = 6.6 Hz), 2.87 (2H, t, J = 7.1 Hz), 3.04–3.08 (2H, m), 3.57 (2H, t, J = 7.1 Hz), 3.82 (3H, s), 3.88 (3H, s), 7.06 (1H, d, J = 8.5 Hz), 7.68 (1H, s), 7.74 (1H, s), 7.78–7.82 (2H, m), 7.96 (1H, s). |

TABLE 13-continued

| Ex. No. | MOLSTRUCTURE | MOLWEIGHT | Activity grade | MS | NMR |
|---|---|---|---|---|---|
| 14-20 | | 343.451 | A | 344 | (DMSO) 1.08 (3H, t, J = 7.4 Hz), 1.57 (3H, d, J = 6.9 Hz), 1.86–1.95 (2H, m), 3.83 (3H, s), 3.88 (3H, s), 4.22–4.25 (1H, m), 4.23 (1H, d, J = 8.4 Hz), 7.68 (1H, d, J = 1.5 Hz), 7.76–7.81 (3H, m), 7.99 (1H, s). |
| 14-21 | | 355.4621 | A | 356 | (DMSO) 1.72–1.82 (6H, ), 2.34–2.42 (2H, m), 3.83 (3H, s), 3.88 (3H, s), 4.37–4.42 (1H, m), 7.09 (1H, d, J = 9.0 Hz), 7.68 (1H, d, J = 1.4 Hz), 7.77–7.82 (3H, m), 7.98 (1H, s). |
| 14-22 | | 343.451 | A | 344 | (DMSO) 1.09 (6H, d, J = 6.7 Hz), 2.12–2.20 (1H, m), 3.46 (2H, d, J = 6.7 Hz), 3.83 (3H, s), 3.89 (3H, s), 7.09 (1H, d, J = 8.4 Hz), 7.70 (1H, d, J = 1.5 Hz), 7.77–7.82 (2H, m), 7.84 (1H, s), 7.99 (1H, s). |
| 14-23 | | 357.4781 | B | 358 | (DMSO) 0.93 (3H, t, J = 7.4 Hz), 1.06 (3H, d, J = 6.7 Hz), 3.42 (1H, dd, J = 7.3 Hz, 13.2 Hz), 3.59 (1H, dd, (3H, s), 7.08 (1H, d, J = 8.3 Hz), 7.69 (1H, s), 7.77–7.84 (3H, m), 7.98 (1H, s). |

TABLE 13-continued

| Ex. No. | MOLSTRUCTURE | MOLWEIGHT | Activity grade | MS | NMR |
|---|---|---|---|---|---|
| 14-24 | | 430.5298 | B | 431 | (DMSO) 1.36 (9H, s), 3.47 (2H, bq), 3.59(2H, bt), 3.82 (3H, s), 3.89 (3H, s), 7.06 (1H, d, J = 8.5 Hz), 7.14 (1H, bt), 7.69 (1H, d, J = 1.4 Hz), 7.76–7.85 (3H, m), 7.99 (1H, s). |
| 14-25 | | 391.4956 | B | 392 | (DMSO) 3.17 (2H, t, J = 7.9 Hz), 3.15–3.20 (8H, m), 7.08 (1H, d, J = 8.5 Hz), 7.20–7.36 (5H, m), 7.69 (1H, s), 7.78 (1H, d, J = 2.0 Hz), 7.82 (1H, s), 7.84 (1H, d, J = 2.0 Hz), 7.99 (1H, s). |
| 14-26 | | 357.4781 | B | 358 | (DMSO) 0.88 (3H, t, J = 7.2 Hz), 1.25–1.50 (4H, m), 1.87 (2H, p, J = 7.3 Hz), 3.52 (2H, t, J = 7.2 Hz), 3.83 (3H, s), 3.88 (3H, s), 7.08 (1H, d, J = 8.3 Hz), 7.69(1H, s), 7.77–7.82 (3H, m), 7.98 (1H, s). |

TABLE 13-continued

| Ex. No. | MOLSTRUCTURE | MOLWEIGHT | Activity grade | MS | NMR |
|---|---|---|---|---|---|
| 14-27 | | 358.4657 | A | 359 | (DMSO) 2.75 (2H, t, J = 6.8 Hz), 3.68 (2H, t, J = 6.8 Hz), 3.82 (3H, s), 3.88 (3H, s), 7.07 (1H, d, J = 8.5 Hz), 7.69 (1H, s), 7.77–7.84 (3H, m), 7.98 (1H, s). |
| 14-28 | | 357.4781 | B | 358 | (DMSO) 0.97 (6H, d, J = 6.2 Hz), 1.73–1.80 (3H, m), 3.54 (2H, t, J = 7.4 Hz), 3.83 (3H, s), 3.88 (3H, s), 7.07 (1H, d, J = 8.4 Hz), 7.69 (1H, d, J = 1.4 Hz), 7.76–7.83 (3H, m), 7.98 (1H, s). |
| 14-29 | | 369.4892 | A | 370 | (DMSO) 1.47–1.98 (8H, m), 2.23–2.28 (2H, m), 3.83 (3H, s), 3.89 (3H, s), 4.21–4.25 (1H, m), 7.09 (1H, d, J = 9.0 Hz), 7.68 (1H, d, J = 1.5 Hz), 7.77–7.80 (3H, m), 7.98 (1H, s). |
| 14-30 | | 395.459 | B | 396 | (DMSO) 3.83 (3H, s), 3.85 (3H, s), 4.85 (2H, s), 7.08 (1H, d, J = 8.5 Hz), 7.14–7.20 (2H, m), 7.57–7.62 (2H, m), 7.69 (1H, s), 7.77 (1H, s), 7.85 (2H, d, J = 8.5), 8.02 (1H, s). |

TABLE 13-continued

| Ex. No. | MOLSTRUCTURE | MOLWEIGHT | Activity grade | MS | NMR |
|---|---|---|---|---|---|
| 14-31 | | 383.4943 | A | 384 | (DMSO) 3.83 (3H, s), 3.86 (3H, s), 6.93–6.96 (1H, m), 7.08 (1H, d, J = 8.5 Hz), 7.21 (1H, d, J = 3.4 Hz), 7.38 (1H, d, J = 5.2 Hz), 7.70 (1H, s), 7.82–7.90 (3H, m), 8.04 (1H, s). |
| 14-32 | | 393.4708 | A | 394 | (DMSO) 3.44 (2H, t, J = 7.1 Hz), 3.83 (6H, s), 3.96 (2H, t, J = 7.1 Hz), 7.05 (1H, d, J = 8.5 Hz), 7.68 (1H, s), 7.80 (2H, s), 7.85 (1H, dd, J = 2.1 Hz, 8.5 Hz), 7.99 (1H, s), 8.51 (1H, d, J = 2.5 Hz), 8.59–8.61 (1H, m), 8.64 (1H, d, J = 1.4 Hz). |
| 14-33 | | 358.422 | A | 359 | (DMSO) 2.63 (3H, d, J = 4.6 Hz), 3.82 (3H, s), 3.89 (3H, s), 4.23 (2H, s), 7.04 (1H, d, J = 8.4 Hz), 7.71 (1H, s), 7.47 (1H, d, J = 2.1 Hz), 7.79 (1H, dd, J = 2.1 Hz, 8.4 Hz), 7.89 (1H, s), 7.98 (1H, s), 8.23(1H, bq). |

TABLE 13-continued
| Ex. No. | MOLSTRUCTURE | MOLWEIGHT | Activity grade | MS | NMR |
|---|---|---|---|---|---|
| 14-34 | | 478.5268 | A | 479 | |
| 14-35 | | 434.4102 | B | | (CDCl3), 3.94 (3H, s), 3.97 (3H, s), 6.85 (1H, d, J = 2.8 Hz), 6.99 (2H, d, J = 4.7 Hz), 7.49 (1H, s), 7.65 (2H, s), 7.67 (2H, d, J = 4.8 Hz), 7.84 (2H, d, J = 2.8 Hz), 7.99 (1H, s), 8.02 (1H, s) |
| 14-36 | | 405.4167 | C | 406 | |
Example 15
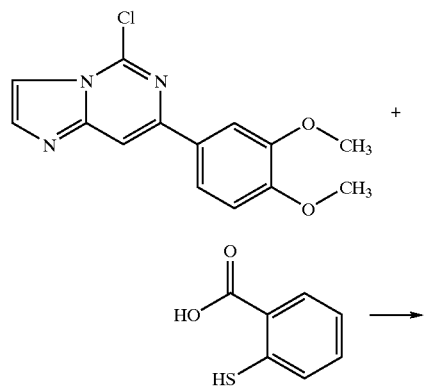
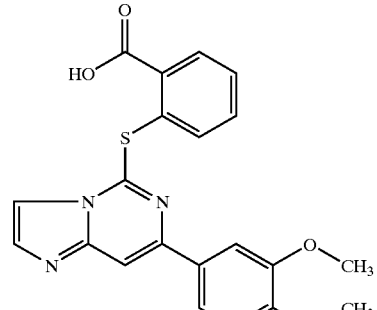
A suspension of 5-Chloro-7-(3,4-dimethoxy-phenyl)-imidazo[1,2-c]pyrimidine (50 mg, 0.17 mmol), 2-Mercaptobenzoicacid (53 mg, 0.35 mmol) and K₂CO₃ (48 mg, 0.35 mmol) in EtOH was stirred at room temperature overnight. Water was added to the reaction mixture. Extraction was carried out with CHCl₃ after neutralization with 1N HCl. The CHCl₃ layer was washed with water and then dried over Na₂SO₄. The organic layer was then concentrated to give the crude product. The resulting 2-(7-Phenyl-imidazo[1,2-c] pyrimidin-5-ylsulfanyl)-benzoic acid was purified by recrystalization from MeOH (40 mg, 57%).

With the use of any of the intermediates I or II and according to the procedure that is similar to that of Example 15, following compounds shown in Table 14 below were prepared.

TABLE 14

| Ex. No. | MOLSTRUCTURE | MOLWEIGH | Activity grade | MS | NMR |
|---|---|---|---|---|---|
| 15-1 | | 432.4274 | A | 433 | |
| 15-2 | | 408.4389 | A | 409 | |
| 15-3 | | 453.5424 | A | 454 | |
| 15-4 | | 352.4399 | B | 353 | (CD3OD) 0.85–2.30 (11H, m), 3.88 (3H, s), 3.92 (3H, s), 7.03 (1H, d, J = 8.4), 7.21 (1H, s), 7.45 (1H, d, J = 1.5), 7.65–7.75 (1H, m), 7.77 (1H, s), 7.84 (1H, s) |

Example 16

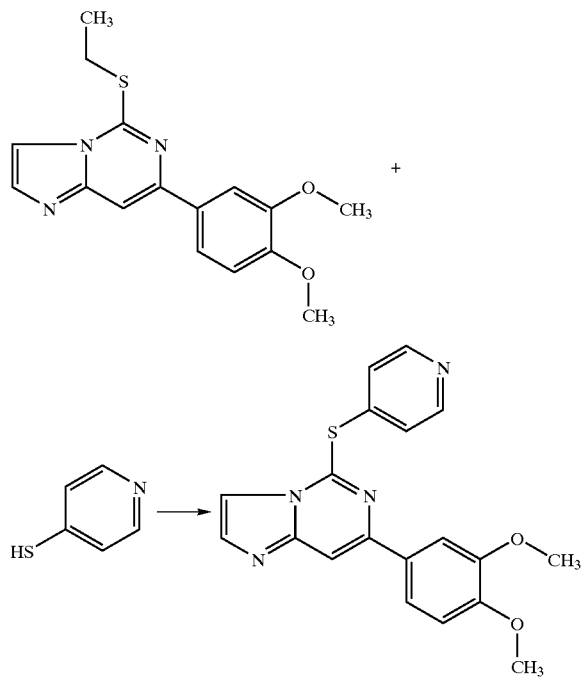

7-(3,4-Dimethoxy-phenyl)-5-ethylsulfanyl-imidazo[1,2-c]pyrimidine (335 mg, 1.06 mmol) was dissolved in trifluoroacetic acid (TFA, 5 ml). After 5 min the TFA was evaporated. The residue was dissolved in 10 ml $CH_2Cl_2$. The solution was cooled to 0° C. and m-CPBA (70%, 524 mg, 2.12 mmol) was added. The reaction mixture was allowed to warm to room temperature and was stirred for 5 h. Diisopropylamine (598 mg, 4.63 mmol) and thiol (254 mg, 2.28 mmol) were added and the mixture was stirred at room temperature overnight. Water was added to the reaction mixture and extraction was carried out with $CHCl_3$. The organic layer was washed with brine, sat. $NaHCO_3$, brine and dried over $Na_2SO_4$. The organic layer was then concentrated to give the crude product of 7-(3,4-Dimethoxy-phenyl)-5-(pyridin-4-ylsulfanyl)-imidazo[1,2-c]pyrimidine which was purified by column chromatography (160 mg, 41%).

Molecular weight: 364.429 Mass spectrometry: 365 Activity grade: A $^1$H-NMR: (DMSO-d6) 3.67 (s, 3H), 3.78 (s, 3H), 6.97 (d, 1H, J=8.52 Hz), 7.38 (d, 1H, J=2.06 Hz), 7.54 (dd, 1H), 7.76 (d, 1H, J=1.45 Hz), 7.80–7.83 (m, 2H), 8.00 (s, 1H), 8.09 (s, 1H), 8.74–8.76 (m, 2H).

With the use of any of the intermediates I or II and according to the procedure that is similar to that of Example 16, following compounds shown in Table 15 below were prepared.

TABLE 15

| Ex. No. | MOLSTRUCTURE | MOLWEIGHT | Activity grade | MS | NMR |
|---|---|---|---|---|---|
| 16-1 | | 369.4077 | A | | (DMSO-d6) 3.75 (s, 3H), 3.79 (s, 3H), 4.16 (s, 3H), 6.98 (d, 1H, J =9.00 Hz), 7.15 (d, 1H, J = 2.00 Hz), 7.38 (dd, 1H), 7.81 (d, 1H, J = 1.45 Hz), 8.18 (s, 1H), 8.18 (d, 1H, J = 0.69 Hz) |
| 16-2 | | 510.6383 | A | | (DMSO-d6) 1.38–1.44 (m, 2H), 1.56–1.65 (m, 4H), 2.95–2.98 (m, 4H), 3.66 (s, 3H), 3.76 (s, 3H), 6.89 (d, 1H, J = 8.55 Hz), 7.36 (d, 1H, J = 1.98 Hz), 7.48 (dd, 1H), 7.77 (d, 1H, J = 1.47 Hz), 7.91 (d, 2H, J = 8.42 Hz), 8.02–8.09 (m, 4H) |

TABLE 15-continued

| Ex. No. | MOLSTRUCTURE | MOLWEIGHT | Activity grade | MS | NMR |
|---|---|---|---|---|---|
| 16-3 | | 387.3862 | | 388 | (DMSO-d6) 7.34 (2H, d, J = 8.2 Hz), 7.57–7.64 (3H, m), 7.78–7.81 (3H, m), 7.94–7.97 (2H, m), 8.04 (1H, s), 8.12 (1H, s) |
| 16-4 | | 402.4008 | | 403 | 5(DMSO-d6) 5.70 (2H, s), 6.73 (2H, d, J = 8.5 Hz), 7.33–7.38 (4H, m), 7.77 (1H, s), 7.97–8.06 (4H, m) |
| 16-5 | | 496.6113 | A | 497 | (DMSO-d6) (m m 3.65 (s, 3H), 3.77 (s, 3H), 6.90 (d, 1H, J = 8.52 Hz), 7.35 (d, 1H, J = 1.88 Hz), 7.49 (dd, 1H,), 7.77 (d, 1H, J = 1.29 Hz), 7.97–8.08 (m, 6H). |
| 16-6 | | 512.6107 | ND | 513 | (DMSO-d6) .95–3.00 (m, 6570 (m 3.69 (s, 3H), 3.75 (s, 3H), 6.92 (d, 1H, J = 8.56 Hz), 7.36 (dd, 1H,), 7.42 (d, 1H, J = 1.95 Hz), 7.77 (d, 1H, J = 1.38 Hz), 7.93 (d, 2H, J = 8.45 Hz), 8.03–8.11 (m, 4H). |

TABLE 15-continued

| Ex. No. | MOLSTRUCTURE | MOLWEIGHT | Activity grade | MS | NMR |
|---|---|---|---|---|---|
| 16-7 | | 379.4437 | A | 380 | (DMSO) 3.64 (s, 3H), 3.77 (s, 3H), 5.94 (br, 2H), 6.94 (d, 1H, J = 8.51 Hz), 7.38–7.40 (m, 2H), 7.52 (dd, 1H), 7.73 (d, 1H, J = 1.42 Hz), 7.82 (d, 1H, J = 4.94 Hz), 7.96 (d, 2H, J = 2.18 Hz), 8.24 (s, 1H). |

Example 17

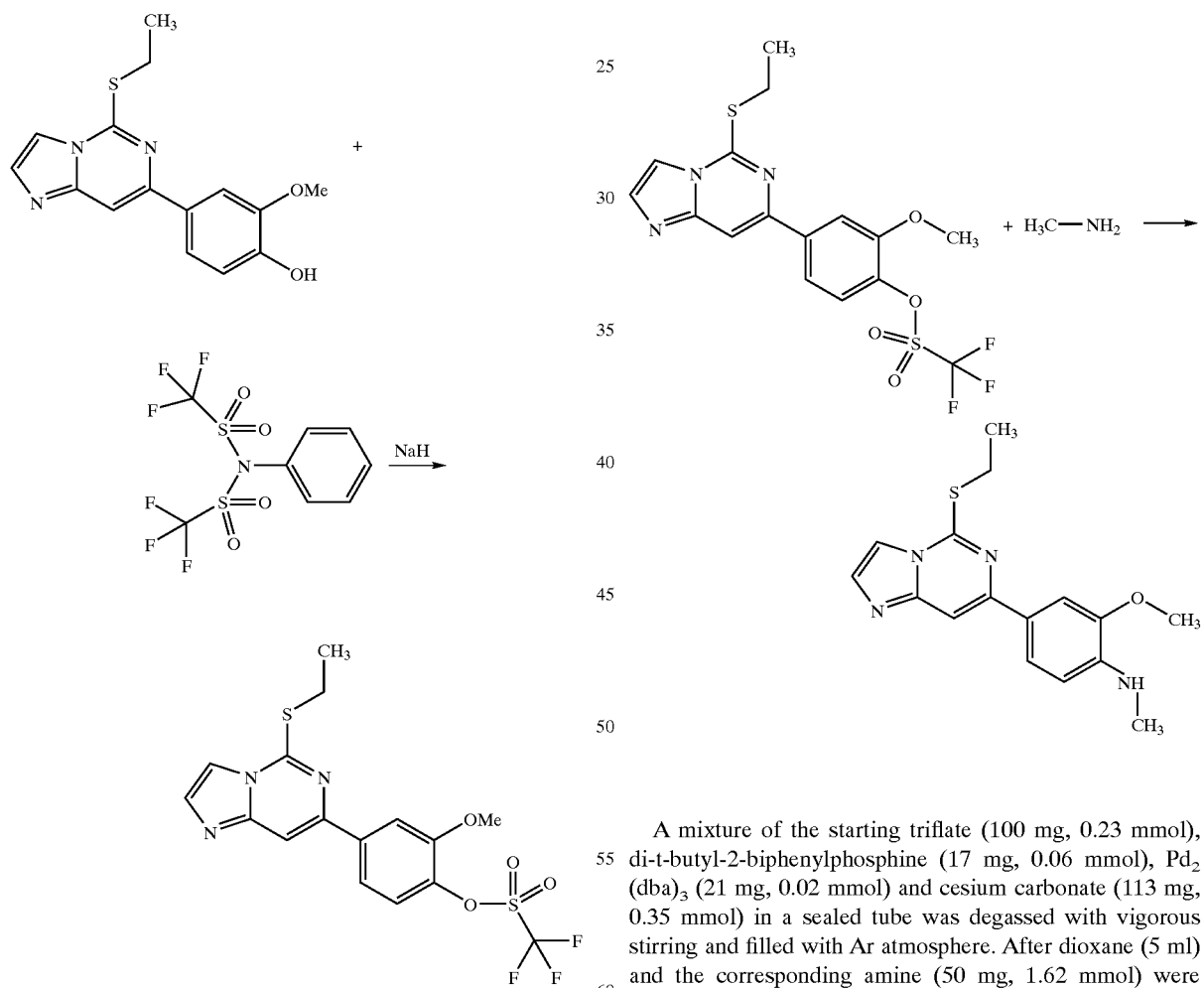

To a solution of 4-(5-ethylsulfanyl-imidazo[1,2-c]pyrimidin-7-yl)-2-methoxy-phenol (7.5 g, 18.1 mmol) in 15 ml of THF was added NaH (2.3 g, 56.6 mmol) at 0° C. After 15 min. at 0° C., N-phenyltrifluromethane sulfonamide (10.2 g, 28.6 mmol) was added. The reaction mixture was stirred at 0° C. for 1 h and then warmed to room temperature. After 1 h, the reaction mixture was concentrated in vacuo. The residue was purified by column chromatography to give the triflate as a light yellow solid (6.3 g, 80%).

A mixture of the starting triflate (100 mg, 0.23 mmol), di-t-butyl-2-biphenylphosphine (17 mg, 0.06 mmol), Pd$_2$(dba)$_3$ (21 mg, 0.02 mmol) and cesium carbonate (113 mg, 0.35 mmol) in a sealed tube was degassed with vigorous stirring and filled with Ar atmosphere. After dioxane (5 ml) and the corresponding amine (50 mg, 1.62 mmol) were added, the mixture was heated at 130–135° C. for 1 d. Cooled to room temperature, the mixture was diluted with 30 ml of CHCl$_3$ and filtered through a Celite pad. The filtrate was concentrated and the residue was purified by preparative thin layer chromatography to give [4-(5-Ethylsulfanyl-imidazo[1,2-c]pyrimidin-7-yl)-2-methoxy-phenyl]-methyl-amine (49 mg, 68%).

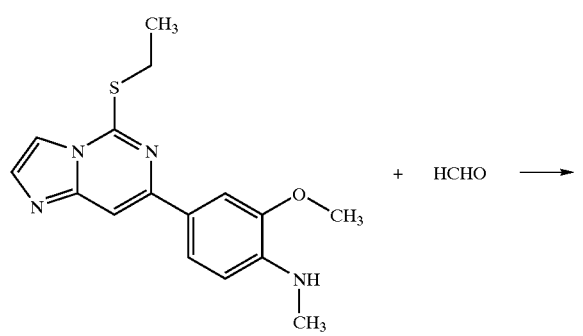 + HCHO → 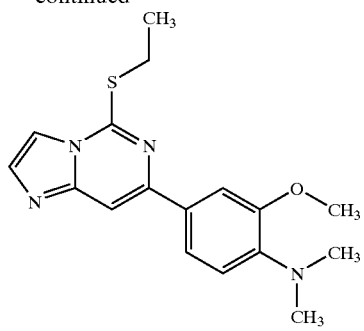

To a solution of the secondary amine (45 mg, 0.14 mmol), formaldehyde (37% in aqueous solution, 30 mg, 1.00 mmol) and NaBH$_3$CN (15 mg, 0.24 mmol) in 5 ml of MeOH was added 0.8 ml of 1N HCl. After stirring at room temperature overnight, the reaction was quenched with 0.5 ml of 1N NaOH. After evaporation, the residue was purified by preparative thin layer chromatography to give tertiary amine (31 mg, 66%).

With the use of any of the intermediates I or II and according to the procedure that is similar to that of Example 17, following compounds shown in Table 16 below were prepared.

TABLE 16

| Ex. No. | MOLSTRUCTURE | MOLWEIGHT | Activity grade | MS | NMR |
|---|---|---|---|---|---|
| 17-1 | | 399.5601 | B | | CDCl3 7.62 (s, 2H), 7.45 (s, 1H), 7.44 (dd, 1H, J = 8.7, 2.3 Hz), 7.30 (d, 1H, J = 2.3 Hz), 6.86 (d, 1H, J = 8.3 Hz), 3.91 (s, 3H), 3.50 (q, 2H J = 7.4 Hz), 3.29 (t, 2H, J = 6.4 Hz), 2.80 (t, 1H, J = 7.3 Hz), 2.62 (s, 6H), 1.82 (m, 4K), 1.57 (t, 3H, J = 7.3 Hz) |
| 17-2 | | 314.4112 | B | | CDCl3 7.66 (s, 1H), 7.62 (s, 1H), 7.46 (s, 1H), 7.43 (dd, 1H, J = 8.3, 2.3 Hz), 7.34 (d, 1H, J = 2.3 Hz), 6.85 (d, 1H, J = 8.3 Hz), 3.91 (s, 3H), 3.51 (q, 2H, J = 7.3 Hz), 2.96 (s, 3H), 1.5 (t, 3H, J = 7.4 Hz) |

TABLE 16-continued

| Ex. No. | MOLSTRUCTURE | MOLWEIGHT | Activity grade | MS | NMR |
|---|---|---|---|---|---|
| 17-3 | | 425.5543 | A | | CDCl3 7.71–7.52 (m, 3H), 7.43 (s, 1H), 7.36 (dd, 1H, J = 3.8 Hz), 6.65 (d, 1H, J = 8.3 Hz), 3.93 (s, 3H), 3.51 (q, 2H, J = 7.4 Hz), 3.41 (m, 4H), 3.25 (t, 2H, J = 6.8 HZ), 2.41 (t, 2H, J = 8.1 HZ), 2.03 (p, 2H, J = 7.7 HZ), 1.88 (p, 2H, J = 7.3 HZ), 1.60 (t, 3H, J = 7.4 HZ) |
| 17-4 | | 440.6128 | A | | CDCl3 7.67 (d, 1H, J = 8.3 Hz), 7.56 (s, 2H), 7.45 (s, 1H), 7.23 (m, 1H), 6.67 (d, 1H, J = 8.3 Hz), 3.97 (s, 3H), 3.52 (q, 2H, J = 7.3 Hz), 3.27 (t, 2H, J = 6.4 Hz), 2.54 (m, 8H), 2.35 (s, 3H), 1.88 (m, 2H), 1.59 (t, 3H, J = 7.4 Hz) |
| 17-5 | | 399.5601 | B | | CDCl3 7.75 (d, 1H, J = 2.3 Hz), 7.71 (dd, 1H, J = 8.3, 2.3 Hz), 7.63 (s, 2H), 7.48 (s, 1H), 6.96 (d, 1H, J = 8.7 Hz), 3.93 (s, 3H), 3.65 (p, 1H, J = 6.8 Hz), 3.51 (q, 2H, J = 7.3 Hz), 3.18 (t, 2H, J = 6.8 Hz), 2.85 (s, 3H), 2.72 (s, 6H), 2.14 (m, 2H), 1.58 (t, 3H, J = 7.3 Hz) |
| 17-6 | | 385.5333 | A | | |

TABLE 16-continued

| Ex. No. | MOLSTRUCTURE | MOLWEIGHT | Activity grade | MS | NMR |
|---|---|---|---|---|---|
| 17-7 | | 371.5065 | B | | CDCl3 7.67 (dd, 1H, J = 8.3, 1.9 Hz), 7.57 (d, 1H, J = 2.6 Hz), 7.55 (s, 2H), 7.44 (s, 1H), 6.67 (d, 1H, J = 8.3 Hz), 3.96 (s, 3H), 3.51 (q, 2H, J = 7.5 Hz), 3.30 (t, 2H, J = 6.4 Hz), 2.64 (t, 2H, J = 6.4 Hz), 2.31 (s, 6H), 1.58 (t, 3H, J = 7.4 Hz) |
| 17-8 | | 371.5065 | B | | CDCl3 7.63 (s, 2H), 7.46 (s, 1H), 7.43 (d, 1H, J = 8.0 Hz), 7.33 (s, 1H), 6.86 (d, 1H, J = 8.3 Hz), 3.91 (s, 3H), 3.51 (q, 2H, J = 7.2 Hz), 3.29 (t, 2H, J = 6.1 Hz), 2.65 (t, 2H, J = 6.3 Hz), 2.29 (s, 6H), 1.58 (t, 3H, J = 7.4 Hz) |
| 17-9 | | 390.5088 | C | | CDCl3 7.56–7.27 (m, 10 Hz), 6.65 (d, 1H, J = 8.3 Hz), 4.46 (br s, 2H), 3.97 (s, 3H), 3.50 (q, 2H, J = 7.4 Hz), 1.57 (t, 3H, J = 7.4 Hz) |
| 17-10 | | 358.4638 | B | | CDCl3 7.65 (d, 1H, J = 8.3 Hz), 7.60 S, 1H), 7.57 (s, 1K), 7.55 (s, 1H), 7.44 (s, 1H), 6.68 (d, 1H, J = 8.3 Hz), 4.76 (br s, 2H), 3.95 (s, 3H), 3.67 (t, 2H, J = 5.3 Hz), 3.51 (q, 2H, J = 7.2 Hz), 3.42 (s, 3H), 3.39 (t, 3H, J = 4.9 Hz), 1.58 (t, 3H, J = 7.1 Hz) |

TABLE 16-continued

| Ex. No. | MOLSTRUCTURE | MOLWEIGHT | Activity grade | MS | NMR |
|---|---|---|---|---|---|
| 17-11 | | 408.5276 | A | | CDCl3 7.63 (s, 2H), 7.46 (s, 1H); 7.43 (d, 1H, J = 8.0 Hz), 7.33 (s, 1H), 6.86 (d, 1H, J = 8.3 Hz), 3.91 (s, 3H), 3.51 (q, 2H, J = 7.2 Hz), 3.29 (t, 2H, J = 6.1 Hz), 2.65 (t, 2H, J = 6.3 Hz), 2.29 (s, 6H), 1.58 (t, 3H, J = 7.4 Hz) |
| 17-12 | | 427.5701 | A | | CDCl3 7.63 (dd, 1H, J = 8.3, 1.9 Hz), 7.59 (s, 1H), 7.56 (s, 2H), 7.44 (s, 1H), 6.66 (d, 1H, J = 8.3 Hz), 5.41 (br s, 1H), 3.97 (s, 3H), 3.78 (m, 4H), 3.50 (q, 2H, J = 7.2 Hz), 3.29 (br s, 2H), 2.52 (m, 4H), 1.87 (p, 2H, J = 6.4 Hz), 1.58 (t, 3H, J = 7.3 Hz) |
| 17-13 | | 385.5333 | A | | CDCl3 7.69 (d, 1H, J = 8.3 Hz), 7.60 (s, 1H), 7.57 (s, 1H), 7.53 (s, 1H), 7.43 (s, 1H), 6.67 (d, 1H, J = 8.3 Hz), 3.94 (s, 3H), 3.51 (q, 2H, J = 7.3 Hz), 3.27 (t, 2H, J = 6.9 Hz), 2.42 (t, 2H, J = 7.0 Hz), 2.27 (s, 6H), 1.85 (p, 2H, J = 6.8 Hz), 1.58 (t, 3H, J = 7.3 Hz) |

TABLE 16-continued

| Ex. No. | MOLSTRUCTURE | MOLWEIGHT | Activity grade | MS | NMR |
|---|---|---|---|---|---|
| 17-14 | | 314.4112 | B | | CDCl3 7.68 (dd, 1H, J = 8.2, 1.9 Hz), 7.59 (d, 1H, J = 1.6 Hz), 7.58 (s, 1H), 7.54 (d, 1H, J = 1.9 Hz), 7.43 (s, 1H), 6.65 (d, 1H, J = 8.2 Hz), 3.94 (s, 3H), 3.50 (q, 2H, J = 7.4 Hz), 2.93 (s, 3H), 1.58 (t, 3H, J = 7.4 Hz) |
| 17-15 | | 328.438 | A | | CDCl3 7.65 (s, 2H), 7.63 (s, 2H), 7.47 (s, 1H), 7.01 (d, 1H, J = 8.6 Hz), 3.99 (s, 3H), 3.51 (q, 2H, J = 7.3 Hz), 2.87 (s, 3H), 1.59 (t, 3H, J = 7.3 Hz) |
| 17-16 | | 415.4945 | A | | CDCl3 7.64 (s, 1H), 7.61 (s, 2H), 7.59 (s, 1H), 7.55 (d, 1H, J = 8.3 Hz), 7.42 (s, 2H), 6.95 (d, 2H, J = 9.1 Hz), 6.75 (d, 1H, J = 8.3 Hz), 3.88 (s, 3H), 3.84 (s, 3H), 3.40 (t, 4H, J = 6.4 Hz), 1.94 (m, 4H) |
| 17-17 | | 441.5969 | A | | CDCl3 7.65 (s, 2H), 7.63 (s, 2H), 7.47 (s, 1H), 7.00 (d, 1H, J = 14.4 Hz), 3.96 (s, 3H), 3.70 (t, 4H, J = 7.9 Hz), 3.51 (q, 2H, J = 12.1 Hz), 3.21 (t, 2H, J = 12.6 Hz), 2.87 (s, 3H), 2.44–2.36 (m, 6H), 1.77 (m, 2H), 1.59 (t, 3H, J = 12.3 Hz) |

TABLE 17

| Ex. No. | MOLSTRUCTURE | MOLWEIGHT | Activity grade | MS | NMR |
|---|---|---|---|---|---|
| 1 | | 331.3802 | B | | (CD3OD) 3.90 (3H, s), 6.92 (1H, d, J = 9.1 Hz), 7.11–7.19 (1H, m), 7.32 (1H, s), 7.39–7.51 (4H, m), 7.54 (1H, s), 7.86 (2H, d, J = 8.7 Hz), 8.06 (1H, s) |
| 2 | | 431.4549 | A | | (d8-DMSO) 2.52–2.62 (2H, m), 2.65–2.76 (2H, m), 3.90 (3H, s), 7.10–7.19 (2H, m), 7.42–7.52 (3H, m), 7.61 (1H, s), 7.79–7.87 (1H, m), 8.01 (2H, d, J = 7.9 Hz), 8.32 (1H, s), 8.91 (1H, s), 9.21 (1H, s), 9.47 (1H, s) |
| 3 | | 373.4179 | A | | (d8-DMSO) 2.14 (3H, s), 3.89 (3H, s), 7.08–7.19 (2H, m), 7.41–7.52 (3H, m), 7.61 (1H, s), 7.78–7.88 (1H, m), 7.95–8.05 (2H, m), 8.31 (1H, s), 8.82 (1H, s), 9.16 (1H, s), 9.47 (1H, s) |

TABLE 17-continued

| Ex. No. | MOLSTRUCTURE | MOLWEIGHT | Activity grade | MS | NMR |
|---|---|---|---|---|---|
| 4 | | 361.4067 | C | 362 | (CDCl3) 3.82 (3H, s), 3.95 (3H, s), 3.99 (3H, s), 6.70–6.77 (2H, m), 6.96–7.02 (2H, m), 7.46 (1H, d, J = 1.1 Hz), 7.60–7.71 (4H, m), 8.32 (1H, d, J = 3.0 Hz) |
| 5 | | 463.4974 | A | 464 | |
| 6 | | 447.498 | A | 448 | |
| 7 | | 447.498 | A | 448 | |

TABLE 17-continued

| Ex. No. | MOLSTRUCTURE | MOLWEIGHT | Activity grade | MS | NMR |
|---|---|---|---|---|---|
| 8 | | 523.5987 | A | 524 | |
| 9 | | 372.3867 | 10000 | 373 | |
| 10 | | 416.4402 | C | | (CDCl3) d 2.24 (3H, s), 2.36 (3H, s), 3.90 (3H, s), 7.07 (1H, d, J = 8.6 Hz), 7.34–7.45 (6H, m), 7.63 (1H, d, J = 1.2 Hz), 7.75 (1H, d, J = 2.2 Hz), 7.81 (1H, s), 7.89 (1H, dd, J = 2.2, 8.6 Hz). |
| 11 | | 404.432 | A | 405 | |

TABLE 17-continued

| Ex. No. | MOLSTRUCTURE | MOLWEIGHT | Activity grade | MS | NMR |
|---|---|---|---|---|---|
| 12 | | 503.6092 | A | 504 | |
| 13 | | 432.4861 | A | 433 | |
| 14 | | 349.352 | 10000 | 350 | |
| 15 | | 417.4715 | C | 418 | |

TABLE 17-continued

| Ex. No. | MOLSTRUCTURE | MOLWEIGHT | Activity grade | MS | NMR |
|---|---|---|---|---|---|
| 16 | | 374.4026 | B | 374 | (CDCl3) d 3.97 (3H, s), 4.02 (3H, s), 7.04 (1H, d, J = 8.4 Hz), 7.17 (1H, d, J = 1 Hz), 7.40 (1H, dd, J = 1 Hz, 8.4 Hz), 7.46–7.60 (5H, m), 8.11 (1H, s), 8.39 (1H, d, J = 8.4 Hz) |
| 17 | | 499.0359 | A | 463 | (CDCl3) 2.68 (2H, t, J = 7.3 Hz), 2.84 (3H, s), 2.91 (2H, t, J = 7.3 Hz), 2.97 (3H, s), 3.62 (3H, s), 3.80 (3H, s), 7.02 (1H, d, J = 8.5 Hz), 7.34 (1H, d, J = 1.9 Hz), 7.52 (2H, d, J = 8.2 Hz), 7.61 (1H, dd, J = 1.9 Hz, 8.5 Hz), 7.72 (2H, d, J = 8.2 Hz), 8.11 (1H, s), 8.17 (1H, d, |
| 18 | | 541.0735 | A | 505 | (CDCl3) 2.70 (2H, t, J = 7.2 Hz), 2.93 (2H, t, J = 7.2 Hz), 3.44 (4H, t, J = 5.1 Hz), 3.53 (4H, t, J = 5.1 Hz), 3.62 (3H, s), 3.79 (3H, s), 6.99 (1H, d, J = 8.6 Hz), 7.34 (1H, d, J = 1.8 Hz), 7.48–7.61 (3H, m), 7.72 (2H, d, J = 8.1 Hz), 8.03 (1H, s), 8.07 (1H, s), 8.22 (1H, s). |

TABLE 17-continued

| Ex. No. | MOLSTRUCTURE | MOLWEIGHT | Activity grade | MS | NMR |
|---|---|---|---|---|---|
| 19 | | 461.5438 | A | 462 | (CDCl3) 1.92–2.04 (1H, m), 2.25–2.31 (1H, m), 2.82–3.02 (3H, m), 3.11 (2H, d, J = 7.8 Hz), 3.75 (3H, s), 3.90 (3H, s), 6.86 (1H, d, J = 8.4 Hz), 7.32 (1H, d, J = 2.1 Hz), 7.38 (1H, dd, J = 2.0 Hz, 8.4 Hz), 7.47–7.52 (2H, m), 7.59(1H, s), 7.64(1H, s), 7.68 (1H, s). |
| 20 | | 434.5208 | A | 435 | (CDCl3) 2.58 (2H, t, J = 7.7 Hz), 3.06 (2H, t, J = 7.7 Hz), 3.75 (3H, s), 3.90 (3H, s), 5.28–5.36 (2H, bs), 6.87 (1H, d, J = 8.5 Hz), 7.31 (1H, d, J = 2.0 Hz), 7.36–7.41 (3H, m), 7.61 (1H, s), 7.65 (1H, d, J = 1.8 Hz), 7.69 (1H, s). |
| 21 | | 448.5479 | A | 449 | (CDCl3) 2.50 (2H, t, J = 7.9 Hz), 2.78 (3H, d, J = 4.8 Hz), 3.05 (2H, t, J = 7.9 Hz), 3.75 (3H, s), 3.90 (3H, s), 5.39–5.40 (1H, bs), 6.87 (1H, d, J = 8.5 Hz), 7.29 (1H, d, J = 2.0 Hz), 7.34–7.39 (3H, m), 7.59–7.67 (5H, m). |

TABLE 17-continued

| Ex. No. | MOLSTRUCTURE | MOLWEIGHT | Activity grade | MS | NMR |
|---|---|---|---|---|---|
| 22 | | 389.4131 | B | | (DMSO-d6) d 3.79 (3H, s), 3.84 (3H, s), 7.13 (1H, d, J = 7.5 Hz), 7.39 (1H, t, J = 7.5 Hz), 7.61–7.90 (1H, m), 8.43 (1H, s), 10.56 (1H, s), 11.74 (1H, s) |
| 23 | | 487.5849 | A | | (DMSO) 2.63 (2H, t, J = 8.4 Hz), 2.93 (2H, t, J = 7.2 Hz), 3.26–3.33 (4H, m), 3.63 (3H, s), 3.77 (3H, s), 6.95 (1H, d, J = 8.7 Hz), 7.35 (1H, d, J = 1.9 Hz), 7.45 (2H, d, J = 8.3 Hz), 7.51 (1H, dd, J = 1.9 Hz, 8.7 Hz), 7.70 (2H, d, J = 8.3 Hz), 7.74 (1H, d, J = 1.5 Hz), 7.96 (1H, d, |
| 24 | | 459.5335 | A | | (DMSO) 3.16 (2H, t, J = 8.8 Hz), 3.27 (2H, t, J = 6.8 Hz), 3.64 (3H, s), 3.78 (3H, s), 6.95 (1H, d, J = 8.3 Hz), 7.36 (1H, d, J = 1.9 Hz), 7.45–7.49 (3H, m), 7.70 (1H, s), 7.73–7.74 (2H, m), 7.96 (1H, s), 7.98 (1H, s). |

TABLE 17-continued

| Ex. No. | MOLSTRUCTURE | MOLWEIGHT | Activity grade | MS | NMR |
| --- | --- | --- | --- | --- | --- |
| 25 | | 444.4357 | A | 331 | (DMSO) 3.40 (2H, bq), 3.76 (2H, t, J = 6.6 Hz), 3.84 (3H, s), 3.90 (3H, s), 7.06 (1H, d, J = 8.4 Hz), 7.72 (1H, d, J = 2.0 Hz), 7.79 (1H, s), 7.83 (1H, dd, J = 2.0 Hz, 8.4 Hz), 7.91 (1H, s), 7.99 (2H, bs), 8.07 (1H, s). |
| 26 | | 345.3796 | C | 346 | (DMSO) 1.59 (3H, s), 3.81 (3H, s), 3.89 (3H, s), 4.00 (2H, s), 7.07 (1H, d, J = 8.9 Hz), 7.65 (1H, d, J = 1.4 Hz), 7.78–7.83 (3H, m), 7.88 (1H, s). |
| 27 | | 330.3666 | A | | (CDCl3) 1.58 (3H, t, J = 7.1 Hz), 3.52 (2H, q, J = 7.1 Hz), 4.04 (3H, s), 7.20 (1H, d, J = 9.0 Hz), 7.52 (1H, s), 7.68 (2H, s), 8.19 (1H, dd, J = 2.3, 9.0 Hz), 8.63 (1H, d, 2.3 Hz) |
| 28 | | 358.4202 | B | | (DMSO d6) 1.52 (3H, t, J = 7.5 Hz), 3.53 (2H, q, J = 7.5 Hz), 3.83 (3H, s), 3.88 (3H, s), 7.10 (1H, d, J = 8.3 Hz), 7.57 (1H), 7.72 (1H), 7.79–7.82 (2H), 7.93 (1H), 8.07 (1H) |

TABLE 17-continued

| Ex. No. | MOLSTRUCTURE | MOLWEIGHT | Activity grade | MS | NMR |
|---|---|---|---|---|---|
| 29 | | 475.5461 | A | | (DMSO) 1.04 (1H, d, J = 6.0 Hz), 1.09 (3H, d, J = 6.3 Hz), 1.17 (3H, d, J = 6.3 Hz), 3.81 (3H, s), 3.86 (3H, s), 4.82–4.87 (1H, m), 7.03 (1H, d, J = 8.5 Hz), 7.26 (2H, d, J = 8.2), 7.39–7.40 (1H, m), 7.61 (2H, d, J = 8.2 Hz), 7.69 (1H, d, J = 8.2 Hz), 7.70 (1H, s), 7.74–7.81 (2H, |
| 30 | | 506.3875 | A | | (DMSO) 2.85–2.90 (1H, m), 3.11–3.15 (1H, m), 3.36–3.78 (3H, m), 3.81 (3H, s), 386 (3H, s), 7.04 (1H, d, J = 8.5 Hz), 7.31 (1H, d, J = 8.2 Hz), 7.60 (1H, s), 7.62 (1H, s), 7.71 (1H, d, J = 8.2 Hz), 7.77 (1H, s), 7.86 (1H, d, J = 8.5 Hz), 8.34 (1H, s). |
| 31 | | 414.4272 | A | | (DMSO) 3.82 (3H, s), 3.87 (3H, s), 7.07 (1H, d, J = 8.2 Hz), 7.39 (1H, t, J = 7.9 Hz), 7.64–7.70 (4H, m), 7.87 (1H, s), 8.17 (1H, d, J = 7.9 Hz), 8.26 (1H, s), 8.69 (1H, d, J = 8.2 Hz), 11.6 (1H, bs). |
| 32 | | 432.4816 | A | | (CDCl3), 3.00 (6H, s), 3.95 (3H, s), 4.01 (3H, s), 6.87 (1H, d, J = 2.8 Hz), 6.98 (1H, d, J = 8.5 Hz), 7.04 (1H, dd, J = 9.1 Hz, J = 2.8 Hz), 7.44 (2H, s), 7.63 (2H, d, J = 4.7 Hz), 7.65 (2H, dd, J = 8.5 Hz, J = 1.9 Hz), 7.71 (2H, d, J = 1.9 Hz) |

TABLE 17-continued

| Ex. No. | MOLSTRUCTURE | MOLWEIGHT | Activity grade | MS | NMR |
|---|---|---|---|---|---|
| 33 | | 404.428 | A | | (CD3OD), 3.89 (3H, s), 3.92 (3H, s), 6.98 (1H, d, J = 2.6 Hz), 7.01 (1H, s), 7.04 (1H, s), 7.15 (2H, d, J = 2.6 Hz), 7.36 (2H, s), 7.56 (2H, d, J = 1.5 Hz), 7.64 (1H, dd, J = 8.8 Hz, J = 2.3 Hz), 7.71 (2H, s), 7.76 (1H, d, J = 2.3 Hz) |
| 34 | | 331.3733 | B | 332 | (MeOD) 3.89 (3H, s), 3.92 (3H, s), 7.07 (1H, d, J = 9.1 Hz), 7.59–7.72 (5H, m), 7.76–7.79 (1H, m), 7.87 (1H, s), 7.91–7.99 (1H, m), 8.00–8.03 (2H, m) |
| 35 | | 345.4001 | C | 346 | (MeOD) 3.85 (3H, s), 3.87 (3H, s), 4.56 (2H, s), 7.03 (1H, d, J = 9.0 Hz), 7.23–7.40 (5H, m), 7.57 (1H, d, J = 1.5 Hz), 7.66–7.70 (2H, m), 7.79–7.81 (2H, m) |
| 36 | | 361.4031 | C | 362 | (MeOD) 3.75 (3H, s), 3.89 (3H, s), 3.92 (3H, s), 6.91 (2H, d, J = 6.6 Hz), 7.07 (1H, d, 8.2 Hz), 7.13 (1H, m), 7.56 (1H, d, J = 1.3 Hz), 7.74–7.77 (2H, m), 7.83 (1H, d, J = 0.63 Hz), 8.37 (2H, d, J = 6.6 Hz) |

TABLE 17-continued

| Ex. No. | MOLSTRUCTURE | MOLWEIGHT | Activity grade | MS | NMR |
|---|---|---|---|---|---|
| 37 | | 390.4012 | A | 391 | (DMSO d-6) 3.86 (3H, s), 3.90 (3H, s), 7.12 (1H, d, J = 8.6 Hz), 7.29 (1H, t, J = 7.4 Hz), 7.690–7.74 (3H, m), 7.91 (1H, s), 8.01 (s, 1H), 8.12 (1H, s), 8.51 (1H, d, J = 7.4 Hz), 8.63 (1H, d, J = 7.4 Hz), 8.96 (1H, brs). |
| 38 | | 445.4849 | A | 446 | DMSO 15.93 (s, 1H), 10.38 (s, 1H), 8.37 (d, 1H, J = 4.2 Hz), 7.72 (s, 1H), 7.58 (s, 1H), 7.41 (d, 1H, J = 1.9 Hz), 7.27 (d, 1H, J = 2.2 Hz), 7.16–7.06 (m, 3H), 4.01 (s, 3H), 3.93 (t, 4H, J = 4.8 Hz), 3.19 (t, 4H, J = 4.4 Hz) |

The compounds shown in the Tables 18 below are synthesized according to any of the procedures described above in combination of known conventional chemical synthesis.

TABLE 18

| No. | R11 |
|---|---|
| 1 | (2-methylbenzamide, H2N-C(=O)-C6H4-) |
| 2 | (2-methylphenol, HO-C6H4-) |
| 3 | (2-methyl-3-hydroxypyridine, HO-pyridine) |

TABLE 18-continued

| No. | R11 |
|---|---|
| 4 | propyl-morpholine |
| 5 | 2,3-dihydroxybutyl |
| 6 | but-3-enyl (CH2CH2CH=CH2) |
| 7 | phenethyl |
| 9 | 5-methylindol-2-yl |
| 10 | N-(6-methylpyridin-3-yl)glycine |
| 11 | 4-methylcyclohexanecarboxylic acid |
| 12 | ethyl butyrate |
| 13 | 2-methyl-6-methoxyphenyl |
| 14 | N,N-dimethyl-2-methylbenzamide |

TABLE 18-continued

| No. | R11 |
|---|---|
| 15 | (E)-3-(4-methylphenyl)acrylic acid |

Preparation Example 1

A mixture of the compound synthesized in Example 1 (10.0 mg) and magnesium stearate (3.0 mg) is granulated with the use of an aqueous solution of soluble starch (7.0 mg/0.07 ml). The granules are dried and blended with 70.0 mg of lactose and 50.0 mg of corn starch. The blend is compressed into a tablet.

Preparation Example 2

The compound synthesized in Example 1 (5.0 mg) and sodium chloride (20.0 mg) are dissolved in distilled water to obtain a total volume of 2.0 ml. The resulting solution was filtered and filled into a 2 ml-ampule under a sterile condition. The ampule is sterilized and sealed to give and injection solution.

(Anaphylactic Bronchoconstriction in Rats)

6 Weeks old male Wistar rats are sensitized intravenously (i.v.) with 10 μg mouse anti-DNP IgE, SPE-7, and 1 days later, the rats are challenged intravenously with 0.3 ml of saline containing 1.5 mg DNP-BSA (30) under anesthesia with urethan (1000 mg/kg, i.p.) and gallamine (50 mg/kg, i.v.). The trachea is cannulated for artifical respiration (2 ml/stroke, 70 strokes/min). Pulmonary inflation pressure (PIP) is recorded through a side-arm of cannula connected to pressure transducer. Change in PIP reflect change of both resistance and compliance of the lungs. To evaluate the drugs prepared in Preparation Example 2, the drug (3 mg/kg) is given i.v. 5 min before challenge. The drug of the present invention shows strong activity in vivo assays.

What is claimed is:

1. A compound of the formula:

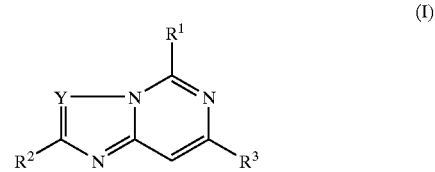

(I)

wherein $R^1$ represents $-OR^{11}$, $-SR^{11}$, $-SOR^{11}$, $-SO_2R^{11}$, $-NHR^{11}$, or $-NR^{12}R^{13}$, $R^{11}$ represents H, phenyl carbonyl, thienyl optionally substituted by $COOR^{111}$ ($R^{111}$ is H or $C_1$–$C_6$ alkyl), pyrimidyl, $C_2$–$C_6$ alkenyl, imidazolyl optionally substituted by $C_1$–$C_6$ alkyl, triazolyl optionally substituted by $C_1$–$C_6$ alkyl, tetrazolyl optionally substituted by $C_1$–$C_6$ alkyl, thiadiazolyl optionally substituted by $C_1$–$C_6$ alkyl, pyrrolidinyl optionally substituted by $C_1$–$C_6$ alkyl, cyclohexenyl, $C_1$–$C_{10}$ straight- or branched-alkyl optionally substituted by $R^{112}$, $R^{113}$ and/or $R^{114}$, $C_3$–$C_{10}$ cyclo-alkyl optionally substituted by $R^{112}$, $R^{113}$ and/or $R^{114}$, phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 hetero atoms selected from the group consisting of N, O and S and optionally substituted by $R^{118}$, $R^{112}$ represents halogen, amino, —COOR$^{112a}$ ($R^{112a}$ represents H or $C_1$–$C_6$ alkyl) —CO—NH—CH$_3$, —CO—NH—(CH$_2$)$_p$CN (p=0, 1, 2, 3, 4, 5, or 6), —NH—COOR$^{112a}$, pyrazinyl, tetrazolyl, dihydrothiophenyl, morpholino, piperidino, di($C_1$–$C_6$ alkyl)amino, indolyl, pyridinyl, thiophenyl, or phenyl optionally substituted by one to three substituents selected from the group consisting of halogen, $C_1$–$C_6$ alkyl, hydroxy, $C_1$–$C_6$ alkoxy, and trihalogen substituted $C_1$–$C_6$ alkyl, $R^{113}$ represents halogen, hydroxy, or $C_1$–$C_6$ alkoxycarbonyl, $R^{114}$ represents halogen, $R^{115}$ represents H, halogen, amino, hydroxy, nitro, cyano, $C_1$–$C_6$ alkoxy, carboxy, $C_1$–$C_6$ alkoxy carbonyl, $C_1$–$C_6$ alkyl carbonyl, morpholino-$C_1$–$C_6$ alkyl-oxy, caroboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, $C_3$–$C_{10}$ cycloalkyl optionally substituted by $R^{115a}$, tetrazolyl, amidino, —CON($R^{115b}$)$R^{115c}$, —SO$_2$N($R^{115b}$)$R^{115c}$, —N($R^{115b}$)$R^{115c}$, —SO$_2$$R^{115d}$, —SOR$^{115d}$, —SR$^{115d}$, or $C_2$–$C_6$ alkenyl optionally substituted by COOR$^{115e}$ $R^{115a}$ represents one or two selected from the group consisting of carboxy, morpholino, morpholino-carbonyl, amino, hydroxy, cyano, $C_1$–$C_6$ alkoxy carbonyl, carbamoyl optionally substituted by cyano-$C_1$–$C_6$ alkyl, methylamino-carbonyl, dimethylamino-carbonyl, —NH—SO$_2$—CH$_3$, tetrazolyl, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, $C_1$–$C_6$ alkylamino, di($C_1$–$C_6$ alkyl)amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atom other than the adjacent N and optionally substituted by $C_1$–$C_6$ alkyl, $R^{115d}$ represents hydroxy, hydroxy $C_1$–$C_6$ alkyl, $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents one to three substituents selected from the group consisting of $C_1$–$C_6$ alkyl, amino, $C_1$–$C_6$ alkoxy, —COOR$^{118a}$ ($R^{118a}$ is H or $C_1$–$C_6$ alkyl), and =O, $R^{12}$ represents $C_1$–$C_6$ alkyl, —(CH$_2$)$_q$—OH, —(CH$_2$)$_q$—CN (q=0, 1, 2, 3, 4, 5, or 6), —CO—$C_1$–$C_6$ alkyl), or —$C_2$–$C_6$ alkenyl, $R^{13}$ is identical to $R^{11}$, or $R^{12}$ and $R^{13}$ together with the adjacent N atom form 4–6 membered saturated heterocyclic ring which may or may not contain 1 heteroatom other than the adjacent N atom selected from the group consisting of O, N, and S the 4–6 membered heterocyclic ring optionally form spiro with dioxacyclopentane, or is optionally fused with benzene, and/or is optionally substituted by one or two substituents selected from the group consisting of $C_1$–$C_6$ alkyl carbonyl, $C_1$–$C_6$ alkyl, hydroxy, hydroxy $C_1$–$C_6$ alkyl, carboxyl, $C_1$–$C_6$ alkoxy carbonyl, carbamoyl, phenyl, halogen substituted phenyl, $C_1$–$C_6$ alkoxy substituted phenyl, $C_1$–$C_6$ alkyl substituted phenyl, nitro phenyl, hydroxy phenyl, $C_1$–$C_6$ alkyl carbonyl phenyl, $C_1$–$C_6$ alkoxy carbonyl phenyl, pyridyl optionally substituted by CF$_3$, pyrimidyl, $C_{3-7}$ cycloalkyl, dioxolanyl, piperidino, halogen substituted phenyl carbonyl, furyl carbonyl, cyano, dimethylamino, benzyl, oxo residue, piperonyl methyl, halogen substituted diphenyl methyl, and trifluorocarbonyl amino, Y is CH or N;

$R^2$ is H, $C_1$–$C_6$ alkyl, carbamoyl, or —COOR$^{21}$, wherein $R^{21}$ is H or $C_1$–$C_6$ alkyl;

$R^3$ is thienyl, pyridyl optionally substituted by halogen or $C_1$–$C_6$ alkoxy, naphthyl optionally substituted by $C_1$–$C_6$ alkoxy, dioxane fused phenyl, dioxacyclopentane fused phenyl, or phenyl optionally substituted by one to three substituents selected from the group consisting of halogen, $C_1$–$C_6$ alkyl, nitro, amino, hydroxy, $C_1$–$C_6$ alkylthio, —OR$^{31}$, —OR$^{32}$, —NR$^{33}$R$^{34}$, and —SO$_2$R$^{35}$, wherein $R^{31}$ and $R^{32}$ are identical or different and represent $C_1$–$C_6$ alkyl carbonyl, $C_1$–$C_6$ alkoxy carbonyl, $C_2$–$C_6$ alkenyl, di($C_1$–$C_6$ alkyl) amino carbonyl, $C_1$–$C_6$ alkyl amino carbonyl, —SO$_2$-R$^{311}$, straight- or branched-$C_1$–$C_6$ alkyl optionally substituted by $R^{312}$, or cyclo-$C_3$–$C_7$ alkyl optionally substituted by $R^{312}$, $R^{311}$ represents $C_1$–$C_6$ alkyl, amino, di($C_1$–$C_6$ alkyl) amino $C_1$–$C_6$ alkyl amino, $C_1$–$C_6$ alkoxy carbonyl $C_1$–$C_6$ alkyl amino, or 5–6 membered saturated hetero ring containing up to 2 heteroatoms of N, S, and/or O and optionally substituted by $C_1$–$C_6$ alkyl or carboxy, $R^{312}$ represents $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by one or three substituents selected from the group consisting of $C_1$–$C_6$ alkyl, carbamoyl, and di($C_1$–$C_6$ alkyl)amino, $R^{33}$ represents H or $C_1$–$C_6$ alkyl, $R^{34}$ represents carboxy $C_1$–$C_6$ alkyl carbonyl, $C_1$–$C_6$ alkyl carbonyl, or $C_1$–$C_6$ alkyl optionally substituted by $R^{341}$, wherein $R^{341}$ represents dimethylamino, $C_1$–$C_6$ alkoxyl, morpholino, phenyl, $C_1$–$C_6$ alkyl substituted piperazino, oxopyrrolidino, or imidazolyl, or —N $R^{33}R^{34}$ forms 5–6-membered saturated hetero cyclic ring optionally containing one more hetero atom selected from the group consisting of N, S, and O and optionally substituted by $C_1$–$C_6$ alkyl, $R^{35}$ represents amino, di($C_1$–$C_6$ alkyl)amino $C_1$–$C_6$ alkyl amino, piperazino optionally substituted by hydroxy $C_1$–$C_6$ alkyl or $C_1$–$C_6$ alkyl, $C_1$–$C_6$ alkoxy carbonyl $C_1$–$C_6$ alkyl amino, morpholino, piperidino optionally substituted by carboxy or $C_1$–$C_6$ alkyl, or hydroxy $C_1$–$C_6$ alkyl amino, or its tautomeric or stereoisomeric form, or its physiologically acceptable salt.

2. The compound as claimed in claim 1, wherein $R^1$ represents —$OR^{11}$, —$SR^{11}$, —$NHR^{11}$, or —$NR^{12}R^{13}$ $R^{11}$ represents H, phenyl carbonyl, thienyl optionally substituted by $COOR^{111}$ ($R^{111}$ is H or $C_1$–$C_6$ alkyl), pyrimidyl, $C_2$–$C_6$ alkenyl, imidazolyl optionally substituted by $C_1$–$C_6$ alkyl, triazolyl optionally substituted by $C_1$–$C_6$ alkyl, tetrazolyl optionally substituted by $C_1$–$C_6$ alkyl, thiadiazolyl optionally substituted by $C_1$–$C_6$ alkyl, pyrrolidinyl optionally substituted by $C_1$–$C_6$ alkyl, cyclohexenyl, $C_1$–$C_{10}$ straight- or branched-alkyl optionally substituted by $R^{112}$, $R^{113}$ and/or $R^{114}$, $C_3$–$C_{10}$ cyclo-alkyl optionally substituted by $R^{112}$, $R^{113}$ and/or $R^{114}$, phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 hetero atoms selected from the group consisting of N and S and optionally substituted by $R^{118}$, $R^{112}$ represents halogen, amino, —$COOR^{112a}$ ($R^{112a}$ represents H or $C_1$–$C_6$ alkyl), —CO—NH—$CH_3$, —CO—NH—$(CH_2)_p$ CN, —NH—$COOR^{112a}$, pyrazinyl, tetrazolyl, dihydrothiophenyl, morpholino, piperidino, di($C_1$–$C_6$ alkyl)amino, indolyl, pyridinyl, thiophenyl, or phenyl optionally substituted by one substituent selected from the group consisiting of halogen, hydroxy, $C_1$–$C_6$ alkoxy, and trihalogen substituted methyl, $R^{113}$ represents halogen, hydroxy, or $C_1$–$C_6$ alkoxycarbonyl, $R^{114}$ represents halogen, $R^{115}$ represents H, halogen, amino, hydroxy, nitro, cyano, carboxy, $C_1$–$C_6$ alkoxycarbonyl, $C_1$–$C_6$ alkoxy, $C_1$–$C_6$ alkyl carbonyl, morpholino-$C_1$–$C_6$ alkyl-oxy, carboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, $C_3$–$C_{10}$ cyclo-alkyl optionally substituted by $R^{115a}$, tetrazolyl, amidino, —$CON(R^{115b})R^{115c}$, —$SO_2N(R^{115b})R^{115c}$, —$N(R^{115b})R^{115c}$, —$SO_2R^{115d}$, —$SOR^{115d}$, —$SR^{115d}$, or $C_2$–$C_6$ alkenyl optionally substituted by $COOR^{115e}$, $R^{115a}$ represents one or two selected from the group consisting of carboxy, morpholino, morpholino-carbonyl, amino, hydroxy, cyano, $C_1$–$C_6$ alkoxy carbonyl, carbamoyl optionally substituted by cyano-$C_1$–$C_6$ alkyl, methylamino-carbonyl, dimethylamino-carbonyl, —NH—$SO_2$—$CH_3$, tetrazolyl, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, $C_1$–$C_6$ alkyl amino, di($C_1$–$C_6$ alkyl)amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero ring optionally having one N or O atoms other than the adjacent N and optionally substituted by $C_1$–$C_6$ alkyl, $R^{115d}$ represents hydroxy, hydroxy $C_1$–$C_6$ alkyl, $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents one to three substituents selected from the group consisting of $C_1$–$C_6$ alkyl, amino, $C_1$–$C_6$ alkoxy, $COOR^{118a}$ (H or $C_1$–$C_6$ alkyl), and =O $R^{12}$ represents $C_1$–$C_6$ alkyl, —$(CH_2)_q$—OH, —$(CH_2)_q$—CN (q=0, 1, 2, 3, 4, 5, or 6), —CO—$C_1$–$C_6$ alkyl), or —$C_2$–$C_6$ alkenyl (—$CH_2$—CH=$CH_2$), $R^{13}$ is identical to $R^{11}$, or $R^{12}$ and $R^{13}$ together with the adjacent N atom form 4–6 membered saturated heterocyclic ring which may or may not contain 1 heteroatom other than the adjacent N atom selected from the group consisting of O, N, and S, the 4–6 membered heterocyclic ring optionally form spiro with dioxacyclopentane, or is optionally fused with benzene, and/or is optionally substituted by one or two substituents selected from the group consisting of $C_1$–$C_6$ alkyl, $C_1$–$C_6$ alkyl carbonyl, hydroxy, hydroxy $C_1$–$C_6$ alkyl, carboxyl, $C_1$–$C_6$ alkoxy carbonyl, carbamoyl, phenyl, halogen substituted phenyl, $C_1$–$C_6$ alkoxy substituted phenyl, $C_1$–$C_6$ alkyl substituted phenyl, nitro phenyl, hydroxy phenyl, $C_1$–$C_6$ alkyl carbonyl phenyl, $C_1$–$C_6$ alkoxy carbonyl phenyl, pyridyl optionally substituted by $CF_3$, pyrimidyl, $C_{3-7}$ cycloalkyl, dioxolanyl, piperidino, halogen substituted phenyl carbonyl, furyl carbonyl, cyano, dimethylamino, benzyl, oxo residue, piperonyl methyl, halogen substituted diphenyl methyl, and trifluorocarbonyl amino, Y is CH or N;

$R^2$ is H $C_1$–$C_6$ alkyl, or carbamoyl;

$R^3$ is thienyl, pyridyl optionally substituted by halogen or $C_1$–$C_6$ alkoxy, dioxane fused phenyl, dioxacyclopentane fused phenyl, or phenyl optionally substituted by one to three substituents selected from the group consisting of halogen, $C_1$–$C_6$ alkyl, nitro, amino, hydroxy, $C_1$–$C_6$ alkylthio, —$OR^{31}$, —$OR^{32}$, —$NR^{33}R^{34}$, and —$SO_2R^{35}$, wherein $R^{31}$ and $R^{32}$ are identical or different and represent nitro, $C_1$–$C_6$ alkyl carbonyl, $C_1$–$C_6$ alkoxy carbonyl, $C_2$–$C_6$alkenyl, di($C_1$–$C_6$ alkyl) amino carbonyl, $C_1$–$C_6$ alkyl amino carbonyl, —$SO_2$—$R^{311}$, straight- or branched-$C_1$–$C_6$ alkyl optionally substituted by $R^{312}$, or cyclo-$C_3$–$C_7$ alkyl optionally substituted by $R^{312}$, $R^{311}$ represents $C_1$–$C_6$ alkyl, amino, di($C_1$–$C_6$ alkyl) amino $C_1$–$C_6$ alkyl amino, $C_1$–$C_6$ alkoxy carbonyl $C_1$–$C_6$ alkyl amino, 5–6 membered saturated hetero ring containing up to 2 heteroatoms of N, S, and/or O and optionally substituted by $C_1$–$C_6$ alkyl or carboxy, $R^{312}$ represents one selected from the group consisting of $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by $C_1$–$C_6$ alkyl, carbamoyl, or di($C_1$–$C_6$ alkyl)amino, $R^{33}$ represents H or $C_1$–$C_6$ alkyl, $R^{34}$ represents carboxy $C_1$–$C_6$ alkyl carbonyl, $C_1$–$C_6$ alkyl carbonyl, or $C_1$–$C_6$ alkyl optionally substituted by $R^{341}$, wherein $R^{341}$ represents dimethylamino, $C_1$–$C_6$ alkoxyl, morpholino, phenyl, $C_1$–$C_6$ alkyl substituted piperazino, oxopyrrolidino, or imidazolyl, or —N $R^{33}R^{34}$ form morpholino optionally substituted by $C_1$–$C_6$ alkyl, thiazinano optionally substituted by $C_1$–$C_6$ alkyl, piperidino optionally substituted by $C_1$–$C_6$ alkyl, or pyrrolidino optionally substituted by $C_1$–$C_6$ alkyl, $R^{35}$ represents amino, di($C_1$–$C_6$ alkyl)amino $C_1$–$C_6$ alkyl amino, hydroxy $C_1$–$C_6$ alkyl amino, $C_1$–$C_6$ alkoxy carbonyl $C_1$–$C_6$ alkyl amino, morpholino, piperazino optionally substituted by hydroxy $C_1$–$C_6$ alkyl or $C_1$–$C_6$ alkyl, or piperidino optionally substituted by carboxy, or its tautomeric or stereoisomeric form, or its physiologically acceptable salt.

3. The compound as claimed in claim 1, wherein $R^1$ represents —$OR^{11}$, —$SR^{11}$, or —$NHR^{11}$ $R^{11}$ represents phenyl optionally substituted by $R^{115}$, $R^{116}$, and/or $R^{117}$, pyridyl optionally substituted by $R^{115}$, $R^{116}$, and/or $R^{117}$, or 9–10-membered unsaturated condensed ring which optionally contains up to 3 N atoms and optionally substituted by $R^{118}$ $R^{115}$ represents H, halogen, amino, hydroxy, nitro, cyano, carboxy, $C_1$–$C_6$ alkoxycarbonyl, $C_1$–$C_6$ alkoxy, $C_1$–$C_6$ alkyl carbonyl, morpholino-$C_1$–$C_6$ alkyl-oxy, carboxy-$C_1$–$C_6$ alkyl-oxy, trihalogen substituted methyl, trihalogen substituted methoxy, $C_1$–$C_{10}$ straight- or branched-alkyl optionally substituted by $R^{115a}$, $C_3$–$C_{10}$ cyclo-alkyl optionally substituted by $R^{115a}$, tetrazolyl, amidino, —CON($R^{115b}$)$R^{115c}$, —$SO_2N(R^{115b})R^{115c}$, —N($R^{115b}$)$R^{115c}$, —$SO_2R^{115d}$, —$SOR^{115d}$, —$SR^{115d}$, or $C_2$–$C_6$ alkenyl optionally substituted by $COOR^{115e}$, $R^{115a}$ represents one or two selected from the group consisting of morpholino, morpholino-carbonyl, amino, hydroxy, cyano, $C_1$–$C_6$ alkoxy carbonyl, carbamoyl, methylamino-carbonyl, dimethylamino-carbonyl, —NH—$SO_2$—$CH_3$, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atoms other than the adjacent N and optionally substituted by $C_1$–$C_6$ alkyl, $R^{115d}$ represents $C_1$–$C_6$alkyl, hydroxy, hydroxy $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy $R^{118}$ represents $C_1$–$C_6$ alkyl, amino, $C_1$–$C_6$ alkoxy, $COOR^{118a}$ ($R^{118a}$ is H or $C_1$–$C_6$ alkyl), or =O (mono or di), Y is CH or N;

$R^2$ is H;

$R^3$ is phenyl optionally substituted by two substituents selected from the group consisting of —$OR^{31}$, —$OR^{32}$, and —$NR^{33}R^{34}$, wherein $R^{31}$ and $R^{32}$ are identical or different and represent straight- or branched-$C_1$–$C_6$ alkyl optionally substituted by $R^{312}$, cyclo-$C_3$–$C_7$ alkyl optionally substituted by $R^{312}$, $R^{312}$ represents one selected from the group consisting of $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by $C_1$–$C_6$ alkyl, carbamoyl, or di($C_1$–$C_6$ alkyl)amino, $R^{33}$ represents H, or $C_1$–$C_6$ alkyl, $R^{34}$ represents $C_1$–$C_6$ alkyl optionally substituted by $C_1$–$C_6$ alkoxyl, or —N $R^{33}R^{34}$ forms morpholino optionally substituted by $C_1$–$C_6$ alkyl, or its tautomeric or stereoisomeric form, or its physiologically acceptable salt.

4. The compound as claimed in claim 1 selected from the group consisting of the following compounds:

[7-(3,4-Dimethoxy-phenyl)-imidazo[1,2-c]pyrimidin-5-yl]-(1H-indazol-6-yl)-amine;

2-[7-(3,4-Dimethoxy-phenyl)-imidazo[1,2-c]pyrimidin-5-ylamino]-benzamide;

2-[7-(3,4-Dimethoxy-phenyl)-imidazo[1,2-c]pyrimidin-5-ylamino]-5-methoxy-benzamide;

2-[7-(3,4-Dimethoxy-phenyl)-imidazo[1,2-c]pyrimidin-5-ylamino]-benzenesulfonamide;

[7-(3,4-Dimethoxy-phenyl)-[1,2,4]triazolo[1,5-c]pyrimidin-5-yl]-(1H-indazol-6-yl)-amide;

4-Amino-2-[7-(3,4-dimethoxy-phenyl)-imidazo[1,2-c]pyrimidin-5-ylamino]-benzamide;

(7-(3-methoxy-4-[(2-methoxy-ethyl)-methyl-amino]-phenyl)-imidazo[1,2-c]pyrimidin-5-yl)-(4-methoxy-phenyl)-amine;

[7-(3-Methoxy-4-morpholin-4-yl-phenyl)-imidazo[1,2-c]pyrimidin-5-yl]-p-tolyl-amine;

(2-Methanesulfonyl-phenyl)-(7-(3-methoxy-4-[(2-methoxy-ethyl)-methyl-amino]-phenyl)-imidazo[1,2-c]pyrimidin-5-yl)-amine;

2-[7-(3-Methoxy-4-morpholin-4-yl-phenyl)-imidazo[1,2-c]pyrimidin-5-ylamino]-nicotinamide;

2-[7-(3-Methoxy-4-morpholin-4-yl-phenyl)-imidazo[1,2-c]pyrimidin-5-ylamino]-benzamide;

2-Methanesulfonyl-phenyl)-[7-(3-methoxy-4-morpholin-4-yl-phenyl)-imidazo[1,2-c]pyrimidin-5-yl]-amine;

4-[7-(3-Methoxy-4-morpholin-4-yl-phenyl)-imidazo[1,2-c]pyrimidin-5-ylamino]-phenol;

[7-(3-Methoxy-4-morpholin-4-yl-phenyl)-imidazo[1,2-c]pyrimidin-5-yl]-(4-methoxy-phenyl)-amine; and 2-[7-(3,4-Dimethoxy-phenyl)-imidazo[1,2-c]pyrimidin-5-ylamino]-nicotinamide or its tautomeric or stereoisomeric form, or its physiologically acceptable salt.

5. A medical composition comprising the compound as claimed in claim 1 or its tautomeric or stereoisomeric form or its physiologically acceptable salt together with one or more pharmaceutically acceptable excipients.

6. A method of treating asthma, which comprises administering to a patient an effective amount of a compound as claimed in claim 1 or its tautomeric or stereoisomeric form or its physiologically acceptable salt.

7. A process for the preparation of the compounds according to claims 1, comprising that a compound of the formula (II)

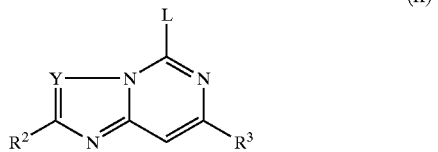

(II)

in which

Y is CH or N;

$R^2$ is H, $C_1$–$C_6$ alkyl, carbamoyl, or —COOR$^{21}$ wherein $R^{21}$ is H or $C_1$–$C_6$ alkyl;

$R^3$ is thienyl, pyridyl optionally substituted by halogen or $C_1$–$C_6$ alkoxy, naphthyl optionally substituted by $C_1$–$C_6$ alkoxy, dioxane fused phenyl, dioxacyclopentane fused phenyl, or phenyl optionally substituted by one to three substituents selected from the group consisting of halogen, $C_1$–$C_6$ alkyl, nitro, amino, hydroxy, $C_1$–$C_6$ alkylthio, —OR$^{31}$, —OR$^{32}$, —NR$^{33}$R$^{34}$, and —SO$_2$R$^{35}$, wherein $R^{31}$ and $R^{32}$ are identical or different and represent $C_1$–$C_6$ alkyl carbonyl, $C_1$–$C_6$ alkoxy carbonyl, $C_2$–$C_6$ alkenyl, di ($C_1$–$C_6$ alkyl) amino carbonyl, $C_1$–$C_6$ alkyl amino carbonyl, —SO$_2$—R$^{311}$, straight- or branched-$C_1$–$C_6$ alkyl optionally substituted by R$^{312}$, or cyclo-$C_3$–$C_7$ alkyl optionally substituted by R$^{312}$, $R^{311}$ represents $C_1$–$C_6$ alkyl, amino, di($C_1$–$C_6$ alkyl) amino $C_1$–$C_6$ alkyl amino, $C_1$–$C_6$ alkoxy carbonyl $C_1$–$C_6$ alkyl amino, 5–6 membered saturated hetero cyclic ring containing up to 2 heteroatoms of N, S, and/or O and optionally substituted by $C_1$–$C_6$ alkyl or carboxy, $R^{312}$ represents $C_1$–$C_6$ alkoxy, halogen, phenyl optionally substituted by $C_1$–$C_6$ alkoxy, di($C_1$–$C_6$ alkyl) amino, $C_1$–$C_6$ alkyl and hydroxy $C_1$–$C_6$ alkyl substituted amino, or 5–6 membered saturated hetero cyclic ring containing up to 2 heteroatoms of N, S, and/or O and optionally substituted by one or three substituents selected from the group consisting of $C_1$–$C_6$ alkyl, carbamoyl, and di($C_1$–$C_6$ alkyl)amino, $R^{33}$ represents H or $C_1$–$C_6$ alkyl, $R^{34}$ represents carboxy $C_1$–$C_6$ alkyl carbonyl, $C_1$–$C_6$ alkyl carbonyl, $C_1$–$C_6$ alkyl optionally substituted by $R^{341}$, wherein $R^{341}$ represents dimethylamino, $C_1$–$C_6$ alkoxyl, morpholino, phenyl, $C_1$–$C_6$ alkyl substituted piperazino, oxopyrrolidino, or imidazolyl, or —N R$^{33}$R$^{34}$ forms 5–6-membered saturated hetero cyclic ring optionally containing one more hetero atom selected from the group consisting of N, S, and O and optionally substituted by $C_1$–$C_6$ alkyl, $R^{35}$ represents amino, di($C_1$–$C_6$ alkyl)amino $C_1$–$C_6$ alkyl amino, piperazino optionally substituted by hydroxy $C_1$–$C_6$ alkyl or $C_1$–$C_6$ alkyl, $C_1$–$C_6$ alkoxy carbonyl $C_1$–$C_6$ alkyl amino, morpholino, piperidino optionally substituted by carboxy or $C_1$–$C_6$ alkyl, or hydroxy $C_1$–$C_6$ alkyl amino; and L represent a leaving group is reacted with a compound of the formula (III)

HR$^1$   (III)

in which $R^1$ represents —OR$^{11}$, —SR$^{11}$, —SOR$^{11}$, —SO$_2$R$^{11}$, —NHR$^{11}$, or —NR$^{12}$R$^{13}$, $R^{11}$ represents H, phenyl carbonyl, thienyl optionally substituted by COOR$^{111}$(R$^{111}$ is H or $C_1$–$C_6$ alkyl), pyrimidyl, $C_2$–$C_6$ alkenyl, imidazolyl optionally substituted by $C_1$–$C_6$ alkyl, triazolyl optionally substituted by $C_1$–$C_6$ alkyl, tetrazolyl optionally substituted by $C_1$–$C_6$ alkyl, thiadiazolyl optionally substituted by $C_1$–$C_6$ alkyl, pyrrolidinyl optionally substituted by $C_1$–$C_6$ alkyl, cyclohexenyl, $C_1$–$C_{10}$ straight- or branched- or cyclo-alkyl optionally substituted by R$^{112}$, R$^{113}$ and/or R$^{114}$, phenyl optionally substituted by R$^{115}$, R$^{116}$, and/or R$^{117}$, pyridyl optionally substituted by R$^{115}$, R$^{116}$, and/or R$^{117}$, or 9–10-membered unsaturated condensed ring which optionally contains up to 3 hetero atoms selected from the group consisting of N, O and S and optionally substituted by R$^{118}$ $R^{112}$ represents halogen, amino, —COOR$^{112a}$ (R$^{112a}$ represents H or $C_1$–$C_6$ alkyl) —CO—NH—CH$_3$, —CO—NH—(CH$_2$)$_p$CN (p=0, 1, 2, 3, 4, 5, or 6), —NH—COOR$^{112a}$, pyrazinyl, tetrazolyl, dihydrothiophenyl, morpholino, piperidino, di($C_1$–$C_6$ alkyl)amino, indolyl, pyridinyl, thiophenyl, or phenyl optionally substituted by one to three substituents selected from the group consisting of halogen, $C_1$–$C_6$ alkyl, hydroxy, $C_1$–$C_6$ alkoxy, and trihalogen substituted $C_1$–$C_6$ alkyl, $R^{113}$ represents halogen, hydroxy, or $C_1$–$C_6$ alkoxy-carbonyl, $R^{114}$ represents halogen, $R^{115}$ represents H, halogen, amino, hydroxy, nitro, cyano, $C_1$–$C_6$alkoxy, carboxy, $C_1$–$C_6$ alkoxy carbonyl, $C_1$–$C_6$ alkyl carbonyl, morpholino-$C_1$–$C_6$ alkyl-oxy, caroboxy-$C_1$–$C_6$ alkyl-oxy, trihalogen substituted methyl, trihalogen substituted methoxy, $C_1$–$C_{10}$ straight- or branched-alkyl optionally substituted by R$^{115a}$, $C_3$–$C_{10}$ cycloalkyl optionally substituted by $R^{115a}$, tetrazolyl, amidino, —$CON(R^{115b})R^{115c}$, —$SO_2N(R^{115b})R^{115c}$, —$N(R^{115b})R^{115c}$, —$SO_2R^{115d}$, —$SOR^{115d}$, —$SR^{115d}$, or $C_2$–$C_6$ alkenyl optionally substituted by $COOR^{115e}$ $R^{115a}$ represents one or two selected from the group consisting of carboxy, morpholino, morpholino-carbonyl, amino, hydroxy, cyano, $C_1$–$C_6$ alkoxy carbonyl, carbamoyl optionally substituted by cyano-$C_1$–$C_6$ alkyl, methylamino-carbonyl, dimethylamino-carbonyl, —NH—$SO_2$—$CH_3$, tetrazolyl, dihydrooxazolyl optionally substituted by $C_1$–$C_6$ alkyl, and 9–10 membered unsaturated condensed ring containing one N atom optionally substituted by =O, $R^{115b}$ represents H or $C_1$–$C_6$ alkyl, $R^{115c}$ represents H, amino, $C_1$–$C_6$ alkylamino, di($C_1$–$C_6$ alkyl)amino, amidino, morpholino-$C_1$–$C_6$ alkyl carbonyl, carboxy-$C_1$–$C_6$ alkyl carbonyl, or straight- or branched $C_1$–$C_6$ alkyl optionally substituted by one or two selected from the group consisting of hydroxy, phenyl, morpholino, di($C_1$–$C_6$ alkyl) amino, $C_1$–$C_6$ alkyl and hydroxy $C_1$–$C_6$ alkyl substituted amino, $C_1$–$C_6$ alkoxy-carbonyl, and carboxy, or $R^{115b}$ and $R^{115c}$ together with the adjacent N form 5 or 6 membered saturated hetero cyclic ring optionally having one N or O atoms other than the adjacent N and optionally substituted by $C_1$–$C_6$ alkyl, $R^{115d}$ represents hydroxy, hydroxy $C_1$–$C_6$ alkyl, $C_1$–$C_6$ alkyl, hydroxy-carbonyl-$C_1$–$C_6$ alkyl, or $C_1$–$C_6$ alkoxy carbonyl $C_1$–$C_6$ alkyl, $R^{115e}$ represents hydrogen or $C_1$–$C_6$ alkyl, $R^{116}$ represents H, $C_1$–$C_6$ alkoxy, $C_1$–$C_6$ alkyl, halogen, or carbamoyl, $R^{117}$ represents H, halogen, or $C_1$–$C_6$ alkoxy, $R^{118}$ represents one to three substituents selected from the group consisting of $C_1$–$C_6$ alkyl, amino, $C_1$–$C_6$ alkoxy, —$COOR^{118a}$ ($R^{118a}$ is H or $C_1$–$C_6$ alkyl), and =O, $R^{12}$ represents $C_1$–$C_6$ alkyl, —$(CH_2)_q$—OH, —$(CH_2)_q$—CN (q=0, 1, 2, 3, 4, 5, or 6), —CO—$C_1$–$C_6$ alkyl, or —$C_2$–$C_6$ alkenyl, $R^{13}$ is identical to $R^{11}$, or $R^{12}$ and $R^{13}$ together with the adjacent N atom form 4–6 membered saturated heterocyclic ring which may or may not contain 1 heteroatom other than the adjacent N atom selected from the group consisting of O, N, and S, the 4–6 membered heterocyclic ring optionally forms spiro with dioxacyclopentane, or is optionally fused with benzene, and/or is optionally substituted by one or two substituents selected from the group consisting of $C_1$–$C_6$ alkyl carbonyl, $C_1$–$C_6$ alkyl, hydroxy, hydroxy $C_1$–$C_6$ alkyl, carboxyl, $C_1$–$C_6$ alkoxy carbonyl, carbamoyl, phenyl, halogen substituted phenyl, $C_1$–$C_6$ alkoxy substituted phenyl, $C_1$–$C_6$ alkyl substituted phenyl, nitro phenyl, hydroxy phenyl, $C_1$–$C_6$ alkyl carbonyl phenyl, $C_1$–$C_6$ alkoxy carbonyl phenyl, pyridyl optionally substituted by $CF_3$, pyrimidyl, $C_{3-7}$ cycloalkyl, dioxolanyl, piperidino, halogen substituted phenyl carbonyl, furyl carbonyl, cyano, dimethylamino, benzyl, oxo residue, piperonyl methyl, halogen substituted diphenyl methyl, and trifluorocarbonyl amino, in inert solvent, if appropriate in the presence of a base and/or in the presence of auxiliary.

\* \* \* \* \*